(12) United States Patent
Baker et al.

(10) Patent No.: US 11,957,707 B2
(45) Date of Patent: Apr. 16, 2024

(54) COMPOSITIONS AND METHODS OF USE THEREOF

(71) Applicant: SYNEDGEN, INC., Claremont, CA (US)

(72) Inventors: Shenda M. Baker, Upland, CA (US); William P. Wiesmann, Chevy Chase, MD (US); Stacy Marie Townsend, Rancho Cucamonga, CA (US)

(73) Assignee: SYNEDGEN, INC., Claremont, CA (US)

( * ) Notice: Subject to any disclaimer, the term of this patent is extended or adjusted under 35 U.S.C. 154(b) by 0 days.

(21) Appl. No.: 16/573,559

(22) Filed: Sep. 17, 2019

(65) Prior Publication Data

US 2020/0009183 A1 Jan. 9, 2020

Related U.S. Application Data

(63) Continuation of application No. 15/510,478, filed as application No. PCT/US2015/049835 on Sep. 11, 2015, now abandoned.

(60) Provisional application No. 62/049,082, filed on Sep. 11, 2014.

(51) Int. Cl.
| | | |
|---|---|---|
| A61K 31/726 | (2006.01) | |
| A61K 9/00 | (2006.01) | |
| A61K 9/08 | (2006.01) | |
| A61K 9/14 | (2006.01) | |
| A61K 9/48 | (2006.01) | |
| A61K 45/06 | (2006.01) | |
| A61K 47/10 | (2017.01) | |

(52) U.S. Cl.
CPC .......... *A61K 31/726* (2013.01); *A61K 9/0078* (2013.01); *A61K 9/08* (2013.01); *A61K 9/14* (2013.01); *A61K 9/48* (2013.01); *A61K 45/06* (2013.01); *A61K 47/10* (2013.01)

(58) Field of Classification Search
CPC .......................... A61K 31/726; A61K 31/7036
See application file for complete search history.

(56) References Cited

U.S. PATENT DOCUMENTS

| | | |
|---|---|---|
| 8,119,780 B2 | 2/2012 | Baker et al. |
| 8,399,635 B2 | 3/2013 | Baker et al. |
| 8,658,775 B2 | 2/2014 | Baker et al. |
| 8,916,542 B2 | 12/2014 | Baker et al. |
| 9,012,429 B2 | 4/2015 | Baker et al. |
| 9,029,351 B2 | 5/2015 | Baker et al. |
| 9,234,050 B2 | 1/2016 | Baker et al. |
| 9,439,925 B2 | 9/2016 | Baker et al. |
| 9,732,164 B2 | 8/2017 | Baker et al. |
| 2003/0087414 A1 | 5/2003 | Aerts et al. |
| 2003/0181416 A1 | 9/2003 | Comper |
| 2004/0242626 A1 | 12/2004 | Achari et al. |
| 2006/0140911 A1 | 6/2006 | Sharp et al. |
| 2007/0117783 A1 | 5/2007 | Brueck-Scheffler |
| 2007/0281904 A1 | 12/2007 | Baker et al. |
| 2009/0304664 A1* | 12/2009 | Lindquist ........... C12N 15/1086 435/375 |
| 2010/0056474 A1 | 3/2010 | Baker et al. |
| 2012/0295355 A1 | 11/2012 | Baker et al. |
| 2012/0301408 A1 | 11/2012 | Baker et al. |
| 2012/0329751 A1 | 12/2012 | Baker et al. |
| 2013/0019860 A1* | 1/2013 | Depla .................... A61K 47/26 128/200.14 |
| 2013/0210761 A1* | 8/2013 | Baker .................... A61P 29/00 514/54 |
| 2014/0080785 A1 | 3/2014 | Baker et al. |
| 2014/0221308 A1 | 8/2014 | Baker et al. |
| 2014/0234310 A1 | 8/2014 | Shapiro |
| 2015/0031610 A1 | 1/2015 | Baker et al. |
| 2015/0224044 A1 | 8/2015 | Baker et al. |
| 2016/0022564 A1 | 1/2016 | Townsend et al. |
| 2016/0022730 A1 | 1/2016 | Baker et al. |
| 2016/0060362 A1 | 3/2016 | Baker et al. |
| 2017/0119810 A1 | 5/2017 | Baker et al. |
| 2017/0136056 A1 | 5/2017 | Baker et al. |
| 2017/0304355 A1 | 10/2017 | Baker et al. |
| 2020/0009182 A1 | 1/2020 | Baker et al. |
| 2020/0009183 A1 | 1/2020 | Baker et al. |

FOREIGN PATENT DOCUMENTS

| | | | |
|---|---|---|---|
| JP | 2009522328 A | 6/2009 | |
| JP | 201507617 A | 1/2015 | |
| WO | WO-0036915 A1 * | 6/2000 | ............ A61K 31/00 |
| WO | WO-07/077164 A1 | 7/2007 | |
| WO | WO-2007/142704 A3 | 5/2008 | |
| WO | WO-2008/072230 A1 | 6/2008 | |

(Continued)

OTHER PUBLICATIONS

Johnson et al. "Nontuberculous mycobacterial pulmonary infections", Journal of Thoracic Disease, vol. 6, No. 3 Mar. 2014 (Year: 2014).*
Henckle "Nontuberculous Mycobacteria Infections in Immunosuppressed Hosts", Clin Chest Med. Mar. 2015 ; 36(1): 91-99 (Year: 2015).*
International Search Report and Written Opinion for International Application No. PCT/US2010/047758, dated Nov. 1, 2010.
Singh, P. K. et al., Nature, "Quorum-sensing signals indicate that cystic fibrosis lungs are infected with bacterial biofilms", Oct. 2000, vol. 407, pp. 762-764.
Supplementary European Search Report dated Apr. 10, 2013 for EP 10 81 4536.

(Continued)

*Primary Examiner* — James W Rogers
(74) *Attorney, Agent, or Firm* — GOODWIN PROCTER LLP

(57) ABSTRACT

Described herein are methods for treating or preventing a disease or disorder of the pulmonary system (e.g., cystic fibrosis), respiratory or digestive system in a subject, the methods comprising administering compounds or compositions comprising water soluble polyglucosamine and derivatized polyglucosamine.

19 Claims, 45 Drawing Sheets

(56) References Cited

FOREIGN PATENT DOCUMENTS

| WO | WO-08049842 A3 | 9/2008 |
| WO | WO-2010056927 A1 | 5/2010 |
| WO | WO-2011/028967 A1 | 3/2011 |
| WO | WO-2011028968 A1 | 3/2011 |
| WO | WO-2011028968 A8 | 4/2011 |
| WO | WO-2013134129 A3 | 6/2015 |
| WO | WO-2016/040899 A1 | 3/2016 |
| WO | WO-2016/172595 A1 | 10/2016 |
| WO | WO-2021/221656 A1 | 11/2021 |
| WO | WO-2021/222727 A1 | 11/2021 |

OTHER PUBLICATIONS

Tin San, et al., "Activity of Chitosans in combination with antibiotics in Pseudomonas aeruginosa" International Journal of Biological Sciences, vol. 5., No. 2, Mar. 1, 2009.

Tre-Hardy, et al., "In vitro activity of antiboitic combinations against Pseudomonas aeruginosa biofilm and planktonic cultures", International Journal of Antimicrobial Agents, Elsevier Science, Amsterdam, NL., vol. 31, No. 4; Feb. 14, 2008.

Extended European Search Report for EP application No. 17182792.6, dated Mar. 2, 2018.

Full Examination Report for Australian Patent Application No. 2015314755, dated Jan. 29, 2019.

International Search Report and Written Opinion for PCT/US2015/049835, dated Dec. 31, 2015.

Supplementary European Search Report dated Mar. 22, 2018 for EP 15840207.

European Search Opinion dated Mar. 22, 2018 for EP15840207.

Deneuville et al. "Revisited Physicochemical and Transport Properties of Respiratory Mucus in Genotyped Cystic Fibrosis Patients" American Journal of Respiratory Critical Care Medicine. 1997, vol. 156 pp. 166-172.

Actor et al. "Lactoferrin as a Natural Immune Modulator" Curr Pharm Des. 2009, vol. 15, pp. 1956-1973.

Sharma et al. "Antibioctics versus biofilm: an emerging battleground in microbial communities", Antimicrobial Resistance and Infection Control (2019) 8:76.

Flemming, et al. "The EPS Matrix: The House of Biofilm Cells", Journal of Bacteriology, Nov. 2007, p. 7945-7947.

Herrero R, et al. "New insights into the mechanisms of pulmonary edema in acute lung injury." Ann Transl Med 2018;6(2):32. doi: 10.21037/atm.2017.12.18.

Jiang et al. "Regulation of lung injury and repair by Toll-like receptors and hyaluronan" Nature, (2005) pp. 1173-1179.

Pechos RD "With Friends Like These: The Complex Role of Neutrophils in the Progression of Severe Pneumonia", Front. Cell. Infect. Microbiol. 7:160.

Yang S-C et al., "Understanding the role of neutrophils in acute respitory distress syndrome." Biomedical Journal, http://doi.org/10/1016/j.bj.2020.09.001.

Maria Cristina Bonferoni et.al. (2009) Chitosan and its salts for mucosal and transmucosal delivery, Expert Opinion on Drug Delivery, 6:9, 923-939, DOI: 10.1517/17425240903114142.

Khalil, H. et al., Antimicrobial Agents and Chemotherapy, "Synergy between Polyethylenimine and Different Families of Antibiotics against a Resistant Clinical Isolate of Pseudomonas aeruginosa", 2008, vol. 52, No. 5, pp. 1635-1641 (Year: 2008).

Narayanswamy et al., (2018) "Novel Glycopolymer Eradicates Antibiotic- and CCCP- Induced Persister Cells in Pseudomonas aeruginosa," Front. Micbrobiol, 9:1724.

Robert C. Read et al. "Effective nasal influenza vaccine delivery using chitosan". Vaccine 23 (2005) 4367-4374.

International Seach Report and Written Opinion issued for PCT/US20/30702, dated Jul. 27, 2020 (8 pages).

International Search Report and Written Opinion issued for PCT/US21/30132, dated Sep. 9, 2021.

U.S. Appl. No. 16/572,053 US 20200009182, Methods and Compositions for Disrupting Biofilm Utilizing Chitosan-Derivative Compunds, filed Sep. 16, 2019.

Garcia et al., "Poly (acetyl, arginyl) glucosamine disrupts Pseudomonas aeruginosa biofilms and enhances bacterial clearance in a rat lung infection model", Microbilogy 2022; 168:001121, 12 pages.

Narayanaswamy et al., "In Vitro Activity of a Novel Glycopolymer against Biofilms of *Burkholderia cepacia* Complex Cystic Fibrosis Clinical Isolate," 2019, 63(6), e00498-19.

Narayanaswamy et al., "In Vitro Activity of a Novel Glycopolymer against Biofilms of *Burkholderia cepacia* Complex Cystic Fibrosis Clinical Isolates," *Antimicrobial Agents and Chemotherapy*, 2019; 63(6); 1-11.

Fang et al., "Characterization of *Burkholderia cepacia* complex from cystic fibrosis patients in China and their chitosan susceptibility," *World Journal of Microbiology and Biotechnology*; 2010; 27, 443-450.

Fisher et al., "Persistent bacterial infections and persister cells," Nat. Rev. Microbiol., 2017, 15, pp. 453-464.

\* cited by examiner

FIG. 20
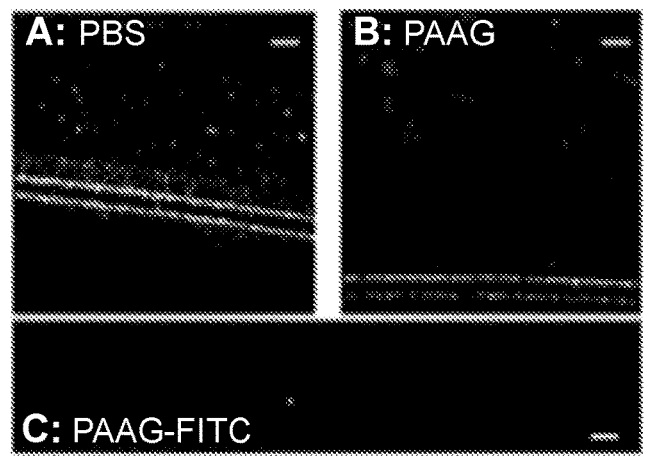
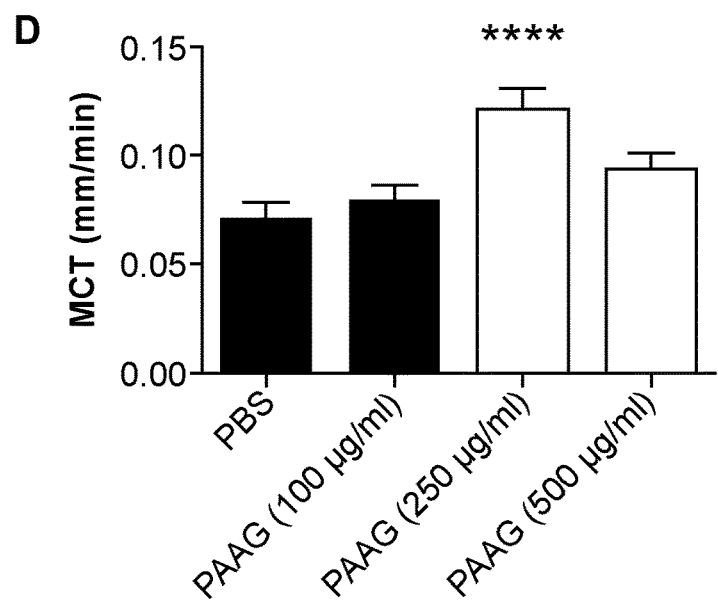
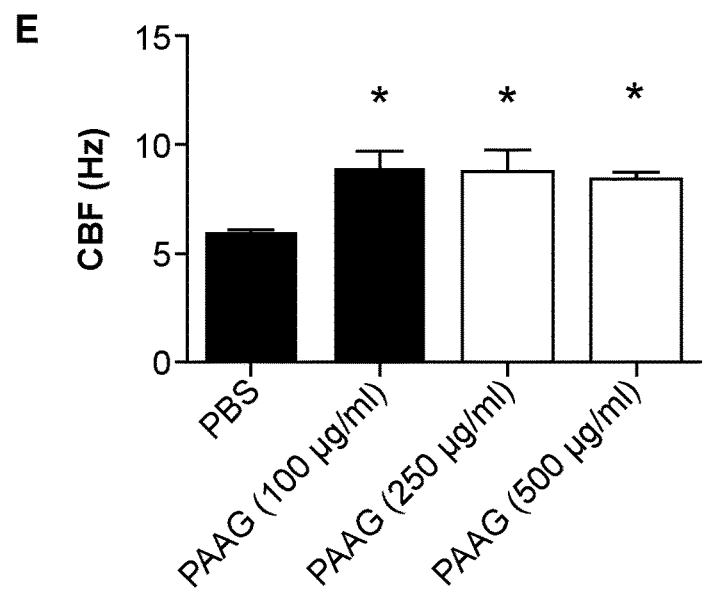

Fig. 22

COMPOSITIONS AND METHODS OF USE THEREOF

CLAIMS OF PRIORITY

This present application is a continuation application of U.S. application Ser. No. 15/510,478 filed Mar. 5, 2018, which is a national phase application under 35 U.S.C. § 371 of International Application No. PCT/US2015/049835 filed Sep. 11, 2015, which claims the benefit of U.S. Ser. No. 62/049,082, filed Sep. 11, 2014, the entire contents of each are incorporated herein by reference.

FIELD OF THE INVENTION

The invention relates to methods for treating a disease or disorder in the pulmonary or digestive system of a subject comprising administering compounds or compositions of water soluble polyglucosamine or derivatized polyglucosamine.

BACKGROUND OF INVENTION

Pulmonary diseases comprise some of the most common and intractable medical conditions in the world. Smoking, infections, and genetics are some factors responsible for most lung diseases. For example, cystic fibrosis (CF) is a genetic disease that causes thick, adherent mucus to build up in the lungs, sinuses, digestive tract and pancreas. This mucus abnormality clogs airways and can cause life-threatening lung infections. Bacteria that do not adhere to normal mucus or tissues are removed by normal airway clearance mechanisms; however, the viscous mucus in CF patients limits mucociliary clearance and facilitates biofilm formation, initiating a cascade that includes dysregulated inflammation and ultimately end organ dysfunction. Current therapies intended to augment mucociliary clearance address components in the mucus [Balsamo, 2010], such as dornase alpha (Pulmozyme®), which is a DNAse [Shak, 1990; Fuchs, 1994] and osmotic therapies that draw fluid from the lungs to dilute mucus and enhance its transport. [Donaldson, 2006; Elkins, 2006; Bilton, 2011] While these standards provided do modestly improve lung function, they do not target the mucus directly, but rather indirectly through the DNA component or simply by adding more water.

Because of the reduced mucociliary clearance of CF patients, their lungs often succumb to bacterial infections. Drugs that target the mucus abnormality do not affect recalcitrant biofilms, the exopolysaccharide material produced by bacteria when they have colonized. Topical, inhaled and systemic antibiotics are used to treat CF patient infections, but these drugs have difficulty penetrating dense biofilms and mucus, and rarely eradicate organisms in the majority with established disease.

Polycationic functionalized polyglucosamines represent a novel treatment to both reduce the viscosity of mucus and the cohesion of biofilms in the lungs, enhancing airway clearance, and potentially augmenting the activity of standard therapeutic agents (e.g., antibiotics) to provide substantial clinical benefit. Development of polycationic functionalized poly glucosamines provide the basis for treatment of CF and other lung diseases with abnormal mucus or delayed mucociliary clearance.

SUMMARY OF INVENTION

Described herein are methods of treating diseases or disorders in a subject wherein the subject would benefit from an increase in mucociliary clearance or reduction in infection or inflammation. Exemplary diseases and disorders include diseases and disorders of the pulmonary system or the digestive system, such as cystic fibrosis and related disorders. Mucosal surfaces are found in the pulmonary tree, including the sinuses, and the gastrointestinal tract. Mucosal surfaces are characterized by epithelial cells with glycocalyx and various forms of mucins, forming a layer on the surface of the mucosa. In some embodiments, the disorder is a chronic disorder. In some embodiments, the disorder is an acute disorder. The present disclosure provides, in one aspect, a method for treating a subject suffering from a mucosal disease or disorder, comprising administering an effective amount of a poly (acetyl, arginyl) glucosamine (PAAG) comprising the following formula (I):

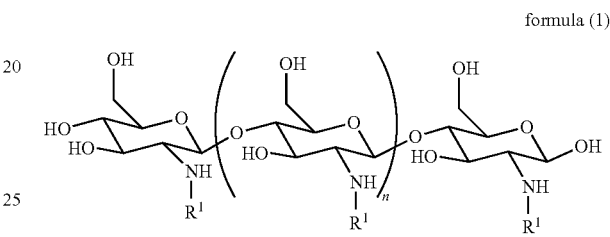

formula (1)

wherein: n is an integer between 20 and 6000; and each $R^1$ is independently selected for each occurrence from hydrogen, acetyl,

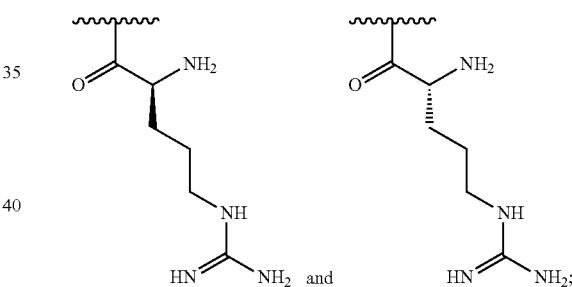

wherein at least 25% of $R^1$ substituents are H, at least 1% of $R^1$ substituents are acetyl, and at least 2% of $R^1$ substituents are

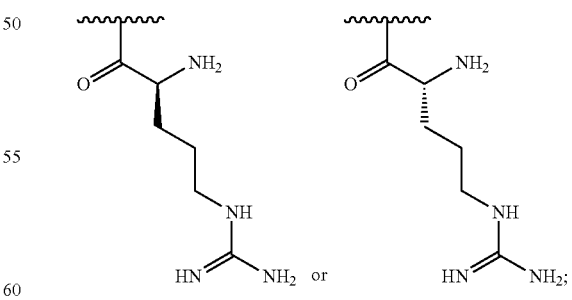

wherein the method improves (e.g., enhances, increases) mucociliary transport or clearance, thereby treating a mucosal disease or disorder.

In some embodiments, the method reduces the viscosity of mucus. In some embodiments, the method reduces the elasticity of mucus.

In some embodiments, the method reduces the adhesion of mucus to epithelia (e.g., gastrointestinal or pulmonary epithelia). In some embodiments, the method reduces the adhesion of bacteria and biofilms to epithelia (e.g., gastrointestinal or pulmonary epithelia).

In some embodiments, the administering delivers a composition comprising the compounds described herein, e.g., a PAAG of formula (I). In some embodiments, the composition is a dry powder composition. In some embodiments, the composition comprises a vacuum-dried, freeze-dried or spray-dried powder of PAAG. In some embodiments, the composition is substantially free of impurities. In some embodiments, the composition is a solution composition (e.g., an aqueous solution composition as described herein, e.g., an aqueous solution composition of neutral osmol). In some embodiments, the composition is a nebulized composition. In some embodiments, the nebulized composition comprises PAAG for pulmonary delivery. In some embodiments, the nebulized composition comprises particles of 1-5 microns in mean particle size diameter.

In some embodiments, the method reduces infection (e.g., bacterial infection). In some embodiments, the infection is from a bacterial infection (e.g., from a bacteria described herein). In some embodiments, the bacterial infection is caused by *Pseudomonas aeruginosa*. In some embodiments, the bacterial infection is caused by *Staphylococcus aureus* or methicillin resistant *Staphylococcus aureus*. In some embodiments, the bacterial infection is caused by *Burkholderia cepacia*.

In some embodiments, the composition is configured for oral delivery. In some embodiments, the composition is a capsule or gel-capsule. In some embodiments the composition is a solution configured for oral administration or delivery.

In some embodiments, the method reduces infection (e.g., bacterial infection). In some embodiments, the method prevents *Burkholderia cepacia* uptake into macrophages.

In some embodiments, the method reduces inflammatory cytokines from pathogenic or damage initiated sources. In some embodiments, the method reduces inflammation (e.g., pulmonary inflammation). In some embodiments, the method reduces LPS stimulated TNF-α secretion. In some embodiments, the method reduces LPS stimulated IL-10 secretion. In some embodiments, the method reduces LPS stimulated IL-8 secretion. In some embodiments, the method reduces DNA stimulated IL-8 secretion. In some embodiments, the method reduces bacterial stimulated IL-8 secretion. In some embodiments, the method reduces inflammatory cytokine secretion compared to a subject treated with lactoferrin.

In some embodiments, the PAAG is present in the composition at between 0.1-2 mg/ml (i.e., 0.01 to 0.2% w/v). In some embodiments, the PAAG is present in the composition at between 0.2-1 mg/ml (i.e., 0.02 to 0.1% w/v). In some embodiments, the PAAG is present in the composition at between 0.2-0.5 mg/ml (i.e., 0.02 to 0.05% w/v).

In some embodiments the method is administered orally. In some embodiments, the method comprises administering a composition (e.g., a solution composition) configured for oral administration. In some embodiments, the composition is a capsule or gel-capsule.

In some embodiments, the method comprises administering a nebulizer solution composition configured for inhaled administration (e.g., a composition as described herein, e.g., a composition comprising PAAG), further comprising a neutral osmol agent (i.e., an agent for achieving neutral osmotic balance).

In some embodiments, the composition is administered at about 1 mL to about 3 mL. For example, in some embodiments, about 1 mL to about 3 mL of the composition described herein (e.g., the solution composition, nebulized solution composition, composition comprising PAAG) is administered to the subject described herein (e.g., once daily, every other day, twice a week, or once a week).

In some embodiments, the composition is administered in an amount (e.g., a volume, e.g., nebulized solution volume) sufficient to provide about 0.1 mg to about 6 mg to the subject. In some embodiments, the composition is administered in an amount sufficient to provide about 0.2 mg to about 3 mg to the subject. In some embodiments, the composition is administered in an amount sufficient to provide about 0.2 mg to about 1.5 mg to the subject. e.g., subject as described herein (e.g., once daily, every other day, twice a week, or once a week).

In some embodiments, the composition is administered in an amount (e.g. a volume, e.g., nebulized solution volume) sufficient to provide at least 0.01 mg, 0.02 mg, 0.05 mg, 0.1 mg, 0.2 mg, 0.3 mg, 0.4 mg, 0.5 mg, 0.6 mg, 0.7 mg, 0.8 mg, 0.9 mg, 1 mg, 1.2 mg, 1.5 mg, 1.7 mg, or 2 mg to the subject, e.g., subject as described herein (e.g., once daily, every other day, twice a week, or once a week).

In some embodiments, the composition is administered once daily. In some embodiments, the composition is administered every other day. In some embodiments, the composition is administered twice a week. In some embodiments, the composition is administered once a week.

In some embodiments, the method further comprises administration of an antibiotic.

In some embodiments, the composition (e.g., a composition as described herein, e.g., a composition comprising PAAG) is administered prior to administration of the antibiotic.

In some embodiments, the composition (e.g., a composition as described herein, e.g., a composition comprising PAAG) is administered concurrently with administration of the antibiotic.

In some embodiments, the average molecular weight of the PAAG is from 20 to 150 kDa. In some embodiments, the average molecular weight of the PAAG is from 20 to 120 kDa. In some embodiments, the average molecular weight of the PAAG is from 40 to 100 kDa In some embodiments, the average molecular weight of the PAAG is from 70-120 kDa In some embodiments, the average molecular weight of the PAAG is from 50-90 kDa In some embodiments, the polydispersity index of the PAAG is from 1.0 to 2.5. In some embodiments, the polydispersity index of the PAAG is from 1.0 to 1.8.

In some embodiments, the pH is about 7 to about 8.

In some embodiments, the PAAG is arginine-functionalized at least 18%. In some embodiments, the PAAG is arginine-functionalized at between 18% and 300/u. In some embodiments, the PAAG is arginine-functionalized at between 20%-30%. In some embodiments, the PAAG is greater than 18% arginine-functionalized.

In some embodiments, the neutral osmol agent is a non-fermentable sugar. In some embodiments, the neutral osmol agent is glycerol, sorbitol, mannitol, xylitol, erythritol or another non-fermentable sugar.

In some embodiments, the non fermentable sugar is glycerol. In some embodiments, the glycerol is present in the composition at between 1.2-2.0% v/v. In some embodiments, the glycerol is present in the composition at between 1.2-1.8% v/v. In some embodiments, the glycerol is present in the composition at between 1.2-1.6% v/v. In some embodiments, the glycerol is present in the composition at between 1.2-1.4% v/v. In some embodiments, the glycerol is present in the composition at between 1.3-1.4% v/v. In some embodiments, the glycerol is around 1.38% v/v.

In some embodiments, the PAAG is present in the composition at between 0.1-2 mg/ml (i.e., 0.01 to 0.2% w/v). In some embodiments, the PAAG is present in the composition at between 0.2-1 mg/ml (i.e., 0.02 to 0.1% w/v). In some embodiments, the PAAG is present in the composition at between 0.2-0.5 mg/ml (i.e., 0.02 to 0.05% w/v).

In some embodiments, the composition comprises a mean particle size diameter of between 1 and 5 microns.

In some embodiments, the osmolality is between 150-550 mOsmol/kg.

In one aspect, described herein is a method for treating a subject suffering from a gastrointestinal disease or disorder, comprising administering an effective amount of a poly (acetyl, arginyl) glucosamine (PAAG) comprising the following formula (I):

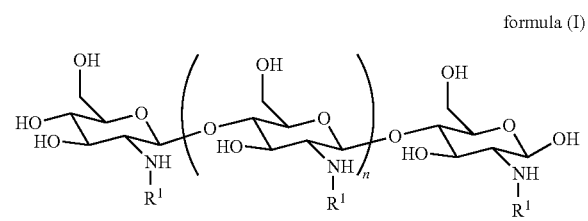

formula (I)

wherein: n is an integer between 20 and 6000; and each $R^1$ is independently selected for each occurrence from hydrogen, acetyl,

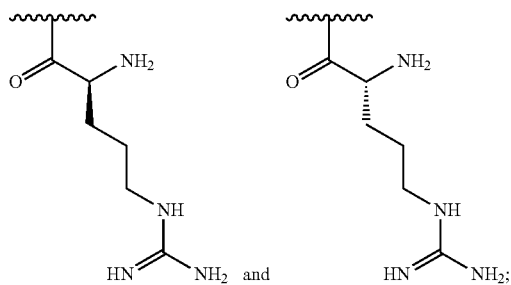 [SMILES: *C(=O)[C@@H](N)CCCNC(=N)N ; "and" ; *C(=O)[C@H](N)CCCNC(=N)N]

wherein at least 25% of $R^1$ substituents are H, at least 1% of $R^1$ substituents are acetyl, and at least 2% of $R^1$ substituents are

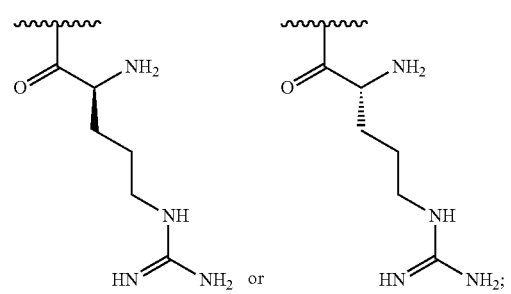 [SMILES: *C(=O)[C@@H](N)CCCNC(=N)N ; "or" ; *C(=O)[C@H](N)CCCNC(=N)N]

wherein the method improves (e.g., enhances, increases) mucociliary transport or clearance, thereby treating the gastrointestinal disease or disorder.

In some embodiments, the gastrointestinal disease is meconium ileus.

In some embodiments, the gastrointestinal disease is DIOS.

In some embodiments, the administering delivers a composition comprising the compounds described herein, e.g., a PAAG of formula (I). In some embodiments, the composition is a dry powder composition. In some embodiments, the composition comprises a vacuum-dried, freeze-dried or spray-dried powder of PAAG. In some embodiments, the composition is substantially free of impurities. In some embodiments, the composition is a solution composition (e.g., an aqueous solution composition as described herein, e.g., an aqueous solution composition of neutral osmol). In some embodiments, the composition is a nebulized composition. In some embodiments, the nebulized composition comprises PAAG for pulmonary delivery. In some embodiments, the nebulized composition comprises particles of 1-5 microns in mean particle size diameter.

In some embodiments, the method reduces infection (e.g., bacterial infection). In some embodiments, the infection is from a bacterial infection (e.g., from a bacteria described herein). In some embodiments, the bacterial infection is caused by *Pseudomonas aeruginosa*. In some embodiments, the bacterial infection is caused by *Staphylococcus aureus* or methicillin resistant *Staphylococcus aureus*. In some embodiments, the bacterial infection is caused by *Burkholderia cepacia*.

In some embodiments, the composition is configured for oral delivery. In some embodiments, the composition is a capsule or gel-capsule. In some embodiments the composition is a solution configured for oral administration or delivery.

In some embodiments, the method reduces infection (e.g., bacterial infection). In some embodiments, the method prevents *Burkholderia cepacia* uptake into macrophages.

In some embodiments, the method reduces inflammatory cytokines from pathogenic or damage initiated sources. In some embodiments, the method reduces inflammation (e.g., pulmonary inflammation). In some embodiments, the method reduces LPS stimulated TNF-α; secretion. In some embodiments, the method reduces LPS stimulated IL-10 secretion. In some embodiments, the method reduces LPS stimulated IL-8 secretion. In some embodiments, the method reduces DNA stimulated IL-8 secretion. In some embodiments, the method reduces bacterial stimulated IL-8 secretion. In some embodiments, the method reduces inflammatory cytokine secretion compared to a subject treated with lactoferrin.

In some embodiments, the PAAG is present in the composition at between 0.1-2 mg/ml (i.e., 0.01 to 0.2% w/v). In some embodiments, the PAAG is present in the composition at between 0.2-1 mg/ml (i.e., 0.02 to 0.1% w/v). In some embodiments, the PAAG is present in the composition at between 0.2-0.5 mg/ml (i.e., 0.02 to 0.05% w/v).

In some embodiments the method is administered orally. In some embodiments, the method comprises administering a composition (e.g., a solution composition) configured for oral administration. In some embodiments, the composition is a capsule or gel-capsule.

In some embodiments, the method comprises administering a nebulizer solution composition configured for inhaled administration (e.g., a composition as described herein, e.g., a composition comprising PAAG), further comprising a neutral osmol agent (i.e., an agent for achieving neutral osmotic balance).

In some embodiments, the composition is administered at about 1 mL to about 3 mL. For example, in some embodiments, about 1 mL to about 3 mL of the composition described herein (e.g., the solution composition, nebulized solution composition, composition comprising PAAG) is administered to the subject described herein (e.g., once daily, every other day, twice a week, or once a week).

In some embodiments, the composition is administered in an amount (e.g., a volume, e.g., nebulized solution volume) sufficient to provide about 0.1 mg to about 6 mg to the subject. In some embodiments, the composition is administered in an amount sufficient to provide about 0.2 mg to about 3 mg to the subject. In some embodiments, the composition is administered in an amount sufficient to provide about 0.2 mg to about 1.5 mg to the subject, e.g., subject as described herein (e.g., once daily, every other day, twice a week, or once a week).

In some embodiments, the composition is administered in an amount (e.g., a volume, e.g., nebulized solution volume) sufficient to provide at least 0.01 mg, 0.02 mg, 0.05 mg, 0.1 mg, 0.2 mg, 0.3 mg, 0.4 mg, 0.5 mg, 0.6 mg, 0.7 mg, 0.8 mg, 0.9 mg, 1 mg, 1.2 mg, 1.5 mg, 1.7 mg, or 2 mg to the subject, e.g., subject as described herein (e.g., once daily, every other day, twice a week, or once a week).

In some embodiments, the composition is administered once daily. In some embodiments, the composition is administered every other day. In some embodiments, the composition is administered twice a week. In some embodiments, the composition is administered once a week.

In some embodiments, the method further comprises administration of an antibiotic.

In some embodiments, the composition (e.g., a composition as described herein. e.g., a composition comprising PAAG) is administered prior to administration of the antibiotic.

In some embodiments, the composition (e.g., a composition as described herein. e.g., a composition comprising PAAG) is administered concurrently with administration of the antibiotic.

In some embodiments, the average molecular weight of the PAAG is from 20 to 150 kDa. In some embodiments, the average molecular weight of the PAAG is from 20 to 120 kDa. In some embodiments, the average molecular weight of the PAAG is from 40 to 100 kDa In some embodiments, the average molecular weight of the PAAG is from 70-120 kDa In some embodiments, the average molecular weight of the PAAG is from 50-90 kDa In some embodiments, the polydispersity index of the PAAG is from 1.0 to 2.5. In some embodiments, the polydispersity index of the PAAG is from 1.0 to 1.8.

In some embodiments, the pH is about 7 to about 8.

In some embodiments, the PAAG is arginine-functionalized at least 18%. In some embodiments, the PAAG is arginine-functionalized at between 18% and 30%. In some embodiments, the PAAG is arginine-functionalized at between 20%-30%. In some embodiments, the PAAG is greater than 18% arginine-functionalized.

In some embodiments, the neutral osmol agent is a non-fermentable sugar. In some embodiments, the neutral osmol agent is glycerol, sorbitol, mannitol xylitol, erythritol or another non-fermentable sugar.

In some embodiments, the non fermentable sugar is glycerol. In some embodiments, the glycerol is present in the composition at between 1.2-2.0% v/v. In some embodiments, the glycerol is present in the composition at between 1.2-1.8% v/v. In some embodiments, the glycerol is present in the composition at between 1.2-1.6% v/v. In some embodiments, the glycerol is present in the composition at between 1.2-1.4% v/v. In some embodiments, the glycerol is present in the composition at between 1.3-1.4% v/v. In some embodiments, the glycerol is around 1.38% v/v.

In some embodiments, the PAAG is present in the composition at between 0.1-2 mg/ml (i.e., 0.01 to 0.2% w/v). In some embodiments, the PAAG is present in the composition at between 0.2-1 mg/ml (i.e., 0.02 to 0.1% w/v). In some embodiments, the PAAG is present in the composition at between 0.2-0.5 mg/ml (i.e., 0.02 to 0.05% w/v).

In some embodiments, the composition comprises a mean particle size diameter of between 1 and 5 microns.

In some embodiments, the osmolality is between 150-550 mOsmol/kg.

In an aspect, described herein is a method for treating a subject suffering from a disease or disorder described herein, such as a pulmonary disease or disorder (e.g., improving lung function (e.g., improving the forced expiratory volume in 1 second (FEVi))), comprising administering to a subject an effective amount of a soluble polyglucosamine or a polyglucosamine derivative. An exemplary soluble polyglucosamine or a polyglucosamine derivative includes, a poly (acetyl, arginyl) glucosamine (PAAG) comprising the following formula (I):

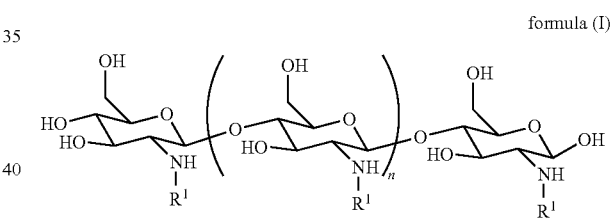

formula (I)

wherein: n is an integer between 20 and 6000; and each $R^1$ is independently selected for each occurrence from hydrogen, acetyl,

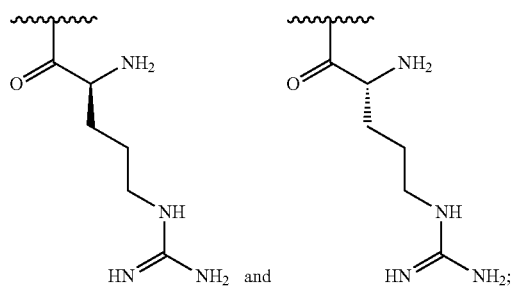 [SMILES: *C(=O)[C@@H](N)CCCNC(=N)N ; "and" ; *C(=O)[C@H](N)CCCNC(=N)N]

wherein at least 25% of $R^1$ substituents are H, at least 1% of $R^1$ substituents are acetyl, and at least 2% of $R^1$ substituents are

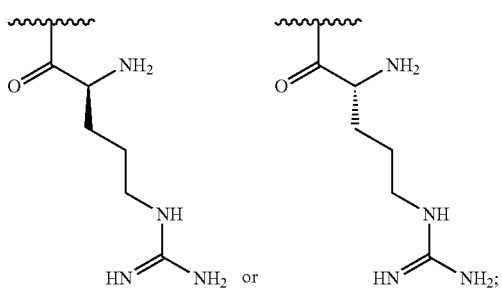

wherein the method improves (e.g., enhances, increases) mucociliary transport or clearance, thereby treating the pulmonary disease or disorder.

In some embodiments, the compound, when administered to a subject results in removal or reduction of a biofilm in the subject. In some embodiments, the method reduces the viscosity of sputum. In some embodiments, the method reduces the elasticity of sputum. In some embodiments, the method improves (e.g., enhances, increases) the mobility of sputum. In some embodiments, the method increases airway surface liquid thickness, increasing fluidity. In some embodiments, the method improves (e.g., enhances, increases) ciliary beat frequency. In some embodiments, the method improves resolution of pulmonary exacerbations.

In some embodiments, the method is mucolytic (e.g., removes mucus).

In some embodiments, the PAAG is mucoadhesive. In some embodiments, the PAAG protects cells (e.g., epithelial cells) from bacterial attachment. In some embodiments, the PAAG reduces mucus adhesion to the cell surface. In some embodiments the PAAG reduces biofilm adhesion to the cell surface.

In some embodiments, the method reduces bacterial colonization and bacterial or biofilm cohesion (e.g., wherein the method reduces biofilm adhesion to the epithelial cell surface). In some embodiments, the method reduces the adhesion CF-specific biofilms to cell surfaces and cohesion of CF specific biofilms. In some embodiments, the method reduces mucus adhesion (e.g., to epithelial cell surfaces). In some embodiments, the method reduces mucosal obstruction.

In some embodiments, the method improves lung function as compared to a subject that has not been treated with the PAAG of formula (I). In some embodiments, the method improves the forced expiratory volume in 1 second (FEVi). In some embodiments, the subject has a complication of cystic fibrosis (e.g., lung infection or respiratory congestion) or a symptom thereof. In some embodiments, the complication of cystic fibrosis is pulmonary exacerbations. In some embodiments, the complication of cystic fibrosis is a gastrointestinal disease or disorder. In some embodiments, the gastrointestinal disease is Distal Intestinal Obstructive Syndrome (DIOS). In some embodiments, the gastrointestinal disease is meconium ileus.

In some embodiments, the pulmonary disease or disorder is a chronic disease or disorder. In some embodiments, the chronic disease is chronic obstructive pulmonary disease (COPD), emphysema, allergic damage, or pulmonary fibrosis.

In some embodiments, the disease is an acute disease. In some embodiments, the acute disease is inhalation damage e.g., from smoke, chemicals, or toxins), acute respiratory distress syndrome, or trauma induced respiratory failure.

In some embodiments, the method further comprises administering an effective amount of an antibacterial agent (e.g., standard of care antibacterial agents to treat infections in CF patients). In some embodiments, the antibacterial agent is tobramycin, vancomycin, or aztreonam (or aztreonam-lysine). In some embodiments, the method potentiates the efficacy of the antibacterial agent (e.g., antibiotics, e.g., pulmonary antibiotics).

In some embodiments, the administering delivers a composition comprising the compounds described herein. e.g., a PAAG of formula (I). In some embodiments, the composition is a dry powder composition. In some embodiments, the composition comprises a vacuum-dried, freeze-dried or spray-dried powder of PAAG. In some embodiments, the composition is substantially free of impurities. In some embodiments, the composition is a solution composition (e.g., an aqueous solution composition as described herein. e.g., an aqueous solution composition of neutral osmol). In some embodiments, the composition is a nebulized composition. In some embodiments, the nebulized composition comprises PAAG for pulmonary delivery. In some embodiments, the nebulized composition comprises particles of 1-5 microns in mean particle size diameter.

In some embodiments, the method reduces infection (e.g., bacterial infection). In some embodiments, the infection is from a bacterial infection (e.g., from a bacteria described herein). In some embodiments, the bacterial infection is caused by *Pseudomonas aeruginosa*. In some embodiments, the bacterial infection is caused by *Staphylococcus aureus* or methicillin resistant *Staphylococcus aureus*. In some embodiments, the bacterial infection is caused by *Burkholderia cepacia*.

In some embodiments, the composition is configured for oral delivery. In some embodiments, the composition is a capsule or gel-capsule. In some embodiments the composition is a solution configured for oral administration or delivery.

In some embodiments, the method reduces infection (e.g., bacterial infection). In some embodiments, the method prevents *Burkholderia cepacia* uptake into macrophages.

In some embodiments, the method reduces inflammatory cytokines from pathogenic or damage initiated sources. In some embodiments, the method reduces inflammation (e.g., pulmonary inflammation). In some embodiments, the method reduces LPS stimulated TNF-α secretion. In some embodiments, the method reduces LPS stimulated IL-10 secretion. In some embodiments, the method reduces LPS stimulated IL-8 secretion. In some embodiments, the method reduces DNA stimulated IL-8 secretion. In some embodiments, the method reduces bacterial stimulated IL-8 secretion. In some embodiments, the method reduces inflammatory cytokine secretion compared to a subject treated with lactoferrin.

In some embodiments, the method reduces pulmonary fibrosis.

In some embodiments, the method increases the accessibility of other therapeutic agents (e.g., anti-bacterials) to bacteria in biofilms. In some embodiments, the method potentiates the effectiveness of other therapeutic agents (e.g., anti-bacterials) for improving lung function. In some embodiments, the anti-bacterial agent and PAAG are present at a concentration, or administered at a dose or doses, which result in a bactericidal activity at least 2 logs more effective than the most effective activity in the absence of the PAAG or anti-bacterial agent.

In some embodiments the method is administered orally. In some embodiments, the method comprises administering a composition (e.g., a solution composition) configured for oral administration. In some embodiments, the composition is a capsule or gel-capsule.

In some embodiments, the method comprises administering a nebulizer solution composition configured for inhaled administration (e.g., a composition as described herein. e.g., a composition comprising PAAG), further comprising a neutral osmol agent (i.e., an agent for achieving neutral osmotic balance).

In some embodiments, the subject is suffering from cystic fibrosis.

In some embodiments, the method provides mucosal clearance in the absence of infection (e.g., relative to a subject that is not treated with the method).

In some embodiments, the PAAG is present in the composition at between 0.1-2 mg/ml (i.e., 0.01 to 0.2% w/v). In some embodiments, the PAAG is present in the composition at between 0.2-1 mg/ml (i.e., 0.02 to 0.1% w/v). In some embodiments, the PAAG is present in the composition at between 0.2-0.5 mg/ml (i.e., 0.02 to 0.05% w/v).

In some embodiments, the composition is administered at about 1 mL to about 3 mL. For example, in some embodiments, about 1 mL to about 3 mL of the composition described herein (e.g., the solution composition, nebulized solution composition, composition comprising PAAG) is administered to the subject described herein (e.g., once daily, every other day, twice a week, or once a week).

In some embodiments, the composition is administered in an amount (e.g. a volume, e.g. nebulized solution volume) sufficient to provide about 0.1 mg to about 6 mg to the subject. In some embodiments, the composition is administered in an amount sufficient to provide about 0.2 mg to about 3 mg to the subject. In some embodiments, the composition is administered in an amount sufficient to provide about 0.2 mg to about 1.5 mg to the subject. e.g., subject as described herein (e.g., once daily, every other day, twice a week, or once a week).

In some embodiments, the composition is administered in an amount (e.g. a volume, e.g., nebulized solution volume) sufficient to provide at least 0.01 mg, 0.02 mg, 0.05 mg, 0.1 mg, 0.2 mg, 0.3 mg, 0.4 mg, 0.5 mg, 0.6 mg, 0.7 mg, 0.8 mg, 0.9 mg, 1 mg, 1.2 mg, 1.5 mg, 1.7 mg, or 2 mg to the subject, e.g., subject as described herein (e.g., once daily, every other day, twice a week, or once a week).

In some embodiments, the composition is administered once daily. In some embodiments, the composition is administered every other day. In some embodiments, the composition is administered twice a week. In some embodiments, the composition is administered once a week.

In some embodiments, the method further comprises administration of an antibiotic.

In some embodiments, the composition (e.g., a composition as described herein, e.g., a composition comprising PAAG) is administered prior to administration of the antibiotic.

In some embodiments, the composition (e.g., a composition as described herein, e.g., a composition comprising PAAG) is administered concurrently with administration of the antibiotic.

In some embodiments, the average molecular weight of the PAAG is from 20 to 150 kDa. In some embodiments, the average molecular weight of the PAAG is from 20 to 120 kDa. In some embodiments, the average molecular weight of the PAAG is from 40 to 100 kDa In some embodiments, the average molecular weight of the PAAG is from 70-120 kDa In some embodiments, the average molecular weight of the PAAG is from 50-90 kDa In some embodiments, the polydispersity index of the PAAG is from 1.0 to 2.5. In some embodiments, the polydispersity index of the PAAG is from 1.0 to 1.8.

In some embodiments, the pH is about 7 to about 8.

In some embodiments, the PAAG is arginine-functionalized at least 18%. In some embodiments, the PAAG is arginine-functionalized at between 18% and 300/u. In some embodiments, the PAAG is arginine-functionalized at between 20%-30%. In some embodiments, the PAAG is greater than 18% arginine-functionalized.

In some embodiments, the neutral osmol agent is a non-fermentable sugar. In some embodiments, the neutral osmol agent is glycerol, sorbitol, mannitol, xylitol, erythritol or another non-fermentable sugar.

In some embodiments, the non fermentable sugar is glycerol. In some embodiments, the glycerol is present in the composition at between 1.2-2.0% v/v. In some embodiments, the glycerol is present in the composition at between 1.2-1.8% v/v. In some embodiments, the glycerol is present in the composition at between 1.2-1.6% v/v. In some embodiments, the glycerol is present in the composition at between 1.2-1.4% v/v. In some embodiments, the glycerol is present in the composition at between 1.3-1.4% v/v. In some embodiments, the glycerol is around 1.38% v/v.

In some embodiments, the PAAG is present in the composition at between 0.1-2 mg/ml (i.e., 0.01 to 0.2% w/v). In some embodiments, the PAAG is present in the composition at between 0.2-1 mg/ml (i.e., 0.02 to 0.1% w/v). In some embodiments, the PAAG is present in the composition at between 0.2-0.5 mg/ml (i.e., 0.02 to 0.05% w/v).

In some embodiments, the composition comprises a mean particle size diameter of between 1 and 5 microns.

In some embodiments, the osmolality is between 150-550 mOsmol/kg.

In an aspect, described herein is a dosage form configured for oral administration, comprising: a PAAG comprising the following formula (I):

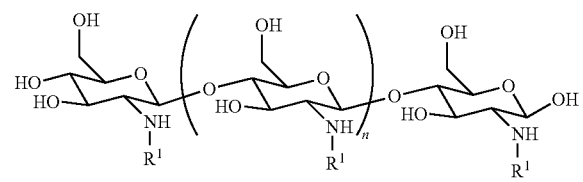

formula (I)

wherein: n is an integer between 20 and 6000; and each $R^1$ is independently selected for each occurrence from hydrogen, acetyl,

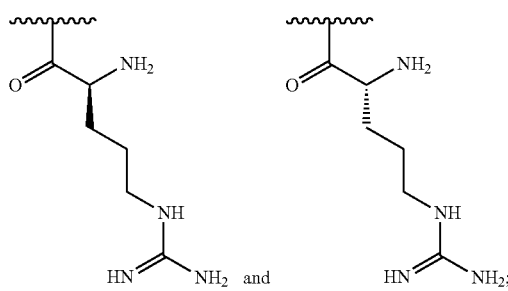 [SMILES: *C(=O)[C@@H](N)CCCNC(=N)N ; "and" ; *C(=O)[C@H](N)CCCNC(=N)N]

wherein at least 25% of $R^1$ substituents are H, at least 1% of $R^1$ substituents are acetyl, and at least 2% of $R^1$ substituents are

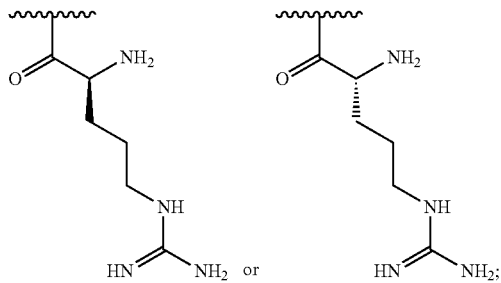

further comprising a neutral osmol agent (i.e., an agent for achieving neutral osmotic balance).

In some embodiments, the dosage form is a capsule or gel-capsule.

In one aspect, the present disclosure provides a nebulizer solution composition configured for inhaled administration, comprising: a PAAG comprising the following formula (I):

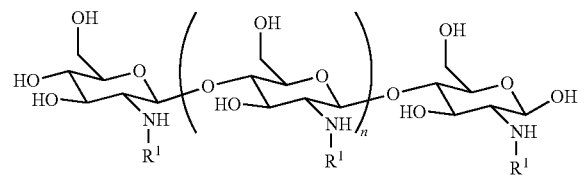

formula (I)

wherein: n is an integer between 20 and 6000; and each $R^1$ is independently selected for each occurrence from hydrogen, acetyl,

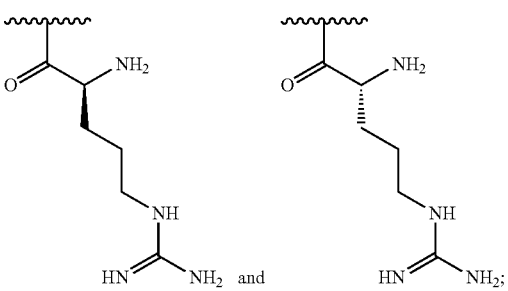 [SMILES: *C(=O)[C@@H](N)CCCNC(=N)N ; "and" ; *C(=O)[C@H](N)CCCNC(=N)N]

wherein at least 25% of $R^1$ substituents are H, at least 1% of $R^1$ substituents are acetyl, and at least 2% of $R^1$ substituents are

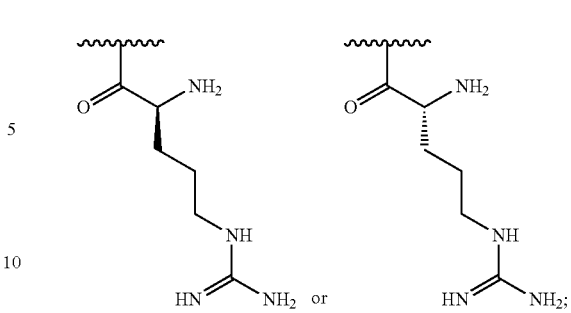

further comprising a neutral osmol agent (i.e., an agent for achieving neutral osmotic balance).

In some embodiments, the molecular weight of the PAAG is from 20 to 150 kDa. In some embodiments, the molecular weight of the PAAG is from 20 to 120 kDa. In some embodiments, the molecular weight of the PAAG is from 40 to 100 kDa.

In some embodiments, the polydispersity index of the PAAG is from 1.0 to 2.5.

In some embodiments, the pH is about 7 to about 8.

In some embodiments, the PAAG is arginine-functionalized at least 18%. In some embodiments, the PAAG is arginine-functionalized at between 18% and 30%. In some embodiments, the PAAG is greater than 18% arginine-functionalized.

In some embodiments, the neutral osmol agent is glycerol, sorbitol, mannitol, xylitol, erythritol or another non-fermentable sugar.

In some embodiments, the neutral osmol agent is a non-fermentable sugar. In some embodiments, the neutral osmol agent is glycerol, sorbitol, mannitol, xylitol, erythritol or another non-fermentable sugar.

In some embodiments, the non fermentable sugar is glycerol. In some embodiments, the glycerol is present in the composition at between 1.2-2.0% v/v. In some embodiments, the glycerol is present in the composition at between 1.2-1.8% v/v. In some embodiments, the glycerol is present in the composition at between 1.2-1.6% v/v. In some embodiments, the glycerol is present in the composition at between 1.2-1.4% v/v. In some embodiments, the glycerol is present in the composition at between 1.3-1.4% v/v. In some embodiments, the glycerol is around 1.38% v/v.

In some embodiments, the PAAG is present in the composition at between 0.1-2 mg/ml (i.e., 0.01 to 0.2% w/v). In some embodiments, the PAAG is present in the composition at between 0.2-1 mg/ml (i.e., 0.02 to 0.1% w/v). In some embodiments, the PAAG is present in the composition at between 0.2-0.5 mg/ml (i.e., 0.02 to 0.05% w/v).

In some embodiments, the composition comprises a mean particle size diameter of between 1 and 5 microns.

In some embodiments, the osmolality is between 150-550 mOsmol/kg.

BRIEF DESCRIPTION OF THE FIGURES

FIG. 20. Measurement of the effect of PAAG on airway surface liquid (ASL) thickness, ciliary beat frequency (CBF) and mucociliary transport (MCT) derived from pt T images of respiratory epithelia.

Figure 22:
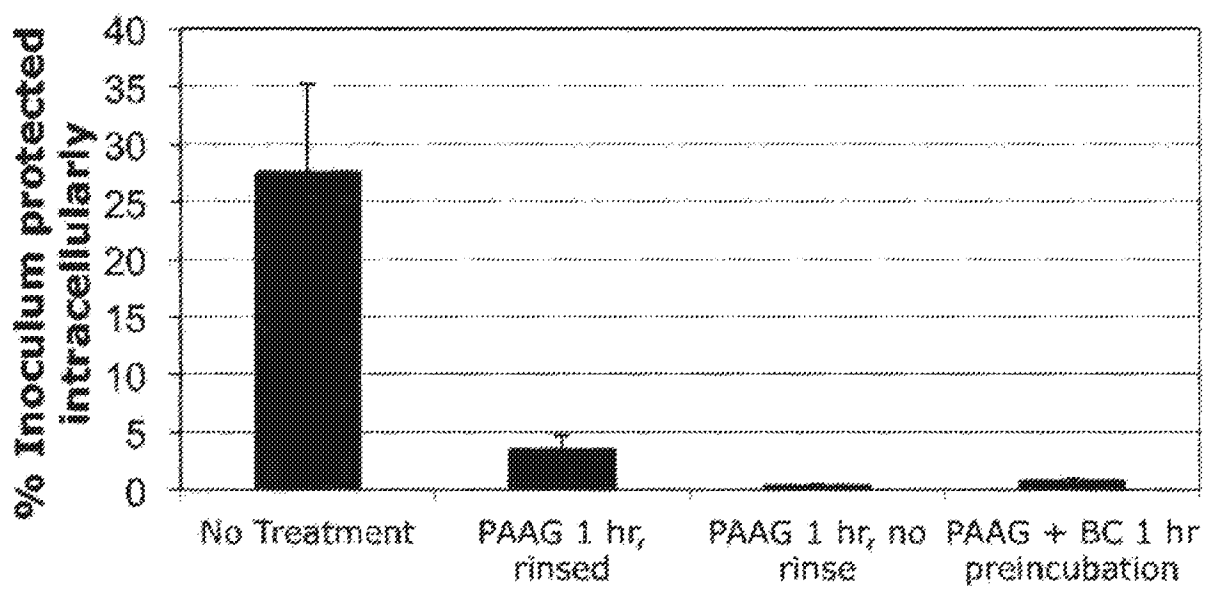

FIG. 22. The gentamicin protection assay shows 1 hour pretreatment of bacteria or macrophages with PAAG at 200 µg/mL final concentration reduces intracellular uptake of Burkholderia cepacia strain Cenocepacia in U937 human macrophages.

DETAILED DESCRIPTION OF THE INVENTION

Entropically Driven Systems

Figure 1:
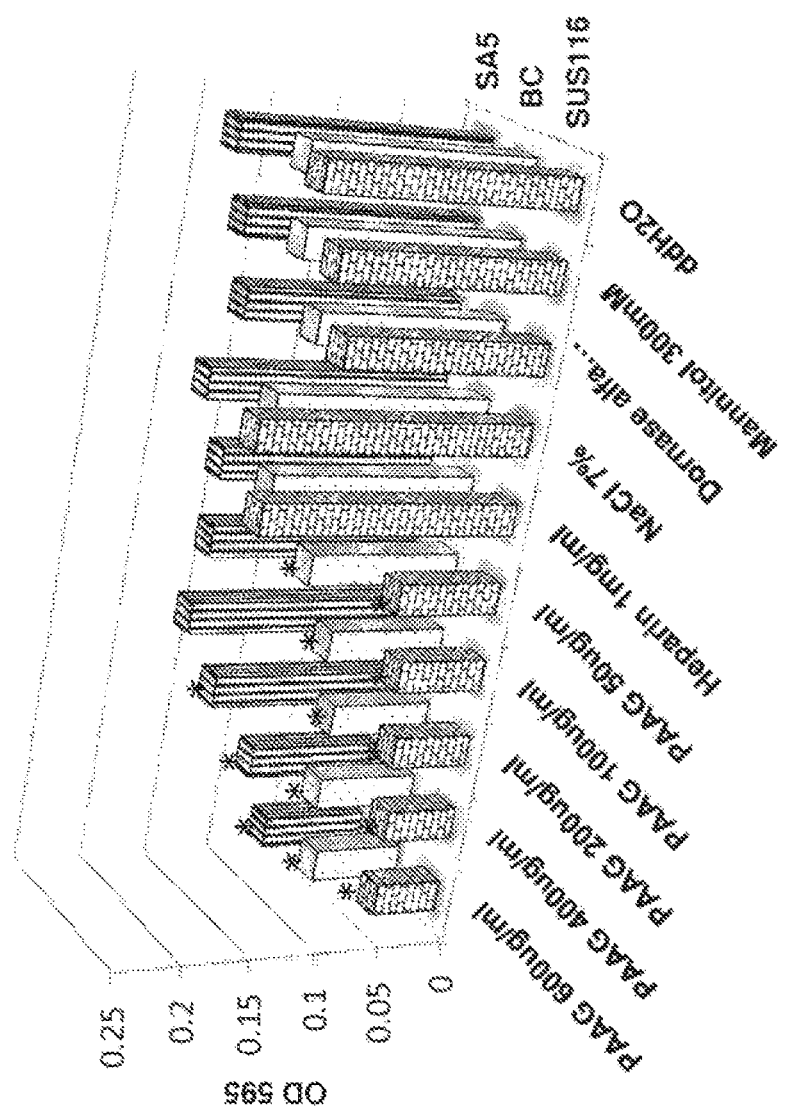
FIG. 1. PAAG at 50-600 µg/mL final concentrations reduce biofilms of MRSA (clinical strain SA5), *P. aeruginosa* (clinical strain SUS116), and *B. cepacia* (ATCC 25416) compared to relevant mucolytics.
Figure 2:
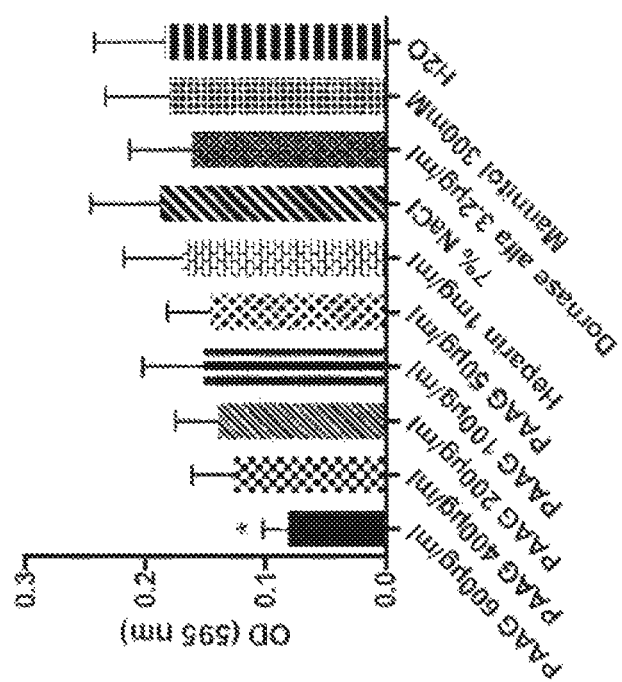
FIG. 2. PAAG at 50-600 µg/mL final concentrations reduce biofilms of MRSA (clinical strain SA4) compared to relevant mucolytics.
Figure 3:
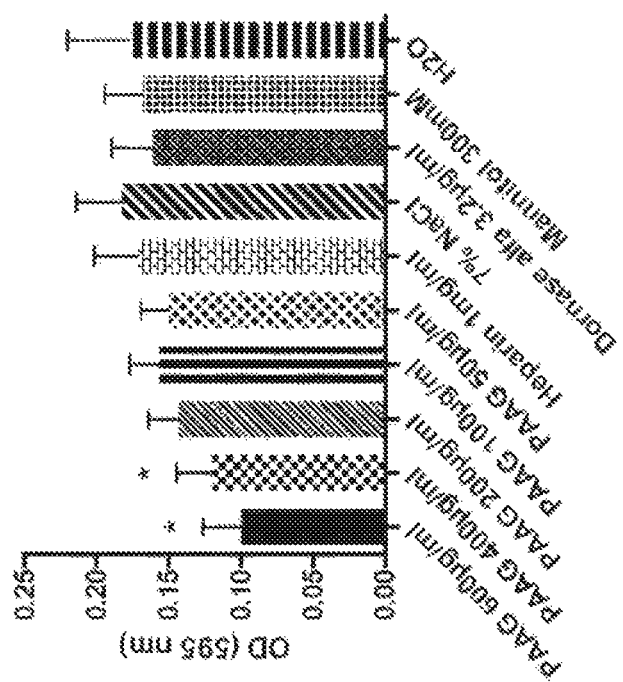
FIG. 3. PAAG at 50-600 µg/mL final concentrations reduce biofilms of MRSA (clinical strain SA6) compared to relevant mucolytics.
Figure 4:
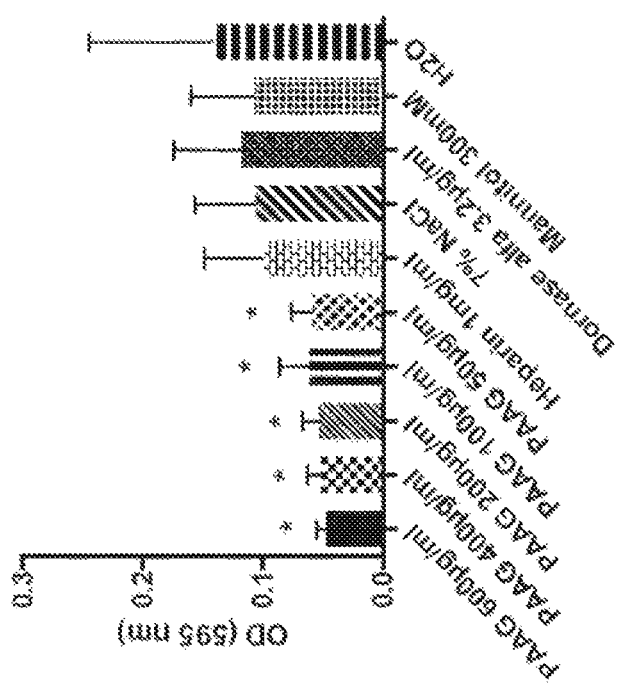
FIG. 4. PAAG at 50-600 µg/mL final concentrations reduce biofilms of P. aeruginosa (clinical strain MR29) compared to relevant mucolytics.

The use of biocompatible polymers to treat biofilms/mucus mechanically rather than through enzymatic or small molecule action is an innovative approach to human pharmaceutical therapy, drawn from decades of materials science research. Polyionic polymers can drive changes in viscosity and adhesion through adjustment of cohesive agents and counterions within a polyelectrolyte (biofilm, polymer, mucin) or viscous mixture. [Kizilay, 2011] Polycationic polymers are used to displace divalent or multivalent cations in many biological systems, such as at membrane interfaces. [Vaara, 1992] In particular, polycationic polymers, the functionalized polyglucosamines, interacting with negatively charged polymers including those in biofilms (such as alginates), the nucleic acids (such as DNA and RNA) and mucus and mucins (such as those found in the pulmonary tree and gastrointestinal tract). Entropically constrained polycationic polymers replace smaller cations, monovalent or divalent, that are counterions for the negative polymer. Given similar enthalpic charge-charge interactions of the small cations or the polycations, the binding/complexation process is driven by the entropic favorability of freeing multiple small molecules at the moderate expense of binding a large, already entropically limited polymer, [de Kruif, 2004]

Negatively charged polymers (polyanions) are commonly found as structural components in nature. Bronchial mucins are key components of mucus (sputum) and are highly glycosylated proteins with neutral sugars and negative sugars modified primarily with negatively charged sialic and neuraminic acids and sulfates. [Holmen, 2004] Negatively charged DNA from neutrophils and other sources are also found in the lung and increase the viscosity of CF mucus. These components are found in all CF patients.

Biofilms, and particularly those of *Pseudomonas* aeruginosa, are comprised primarily of negatively charged polysaccharides such as alginate. Biofilms occur in patients who are infected with bacteria and are enhanced in the airways of CF patients where the mucociliary clearance is reduced or nonexistent.

A class of highly polycationic and nontoxic polysaccharides, functionalized polyglucosamines, (e.g., compounds as described herein), increases the pourability of sputum, reduces cohesion and viscosity of biofilms and sputum (primarily mucins with various amounts of addition DNA or biofilm). The interaction of the functionalized polyglucosamines with these negatively charged polymers is primarily entropically driven and does not depend on the nature of the negatively charged polymers. Binding of DNA by polycationic polymers is shown to be primarily entropic in origin, causing the release of cations from the nucleic acid upon polycationic polymer complexation. [Mascotti, 1997] Functionalized polyglucosamines tightly bind DNA, in a similar fashion to the polycationic synthetic polymer PEI (polyethylenimine). [Utsuno, 2010] Tuning the chemical interactions of polycation polyglucosamines with biological systems, utilizes the design of these molecules molecular weight (MW) and % cationic functionalization to reduce cohesion and viscosity in biofilms and mucins.

This physical, entropically driven interaction is also expressed by mucoadhesivity of polycationic polyglucosamines, including poly (acetyl, arginyl) glucosamine ("PAAG"), to epithelial surfaces through the glycocalyx and mucosal surfaces via the mucin layers/glycocalyx surface. The glycocalyx is the complex array of glycosaminoglycans that cover the cell surface, held by glycosylated proteins and phospholipids. These sugars in the glycocalyx are neutral or negatively charged, with mono or divalent cations as counterions. Surface displacement of mono- and divalent cations, such as $Na^+$, $Ca^{2+}$ and $Mg^{2+}$, by polymeric cations is also common polyelectrolyte entropically driven surface modification [Jia, 2014; Ou, 2006] The described polycationic polyglucosamines are mucoadhesive due to their ability to displace these cations modify the charge exchange characteristics of the glycocalyx to reduce mucin and biofilm adhesion. Tuning the chemical interactions of polycation polyglucosamines with biological systems, utilizes the design of these molecules' MW and % functionalization to adhere to and modulate biological surfaces.

In some embodiments, the compounds described herein are mucoadhesive. In some embodiments, the compounds described herein modify the charge exchange of the glycocalyx. In some embodiments, the compounds described herein can be used to displace (e.g., release) cations (e.g., monovalent, cations, divalent cations, or polycations). In some embodiments, the compounds described herein are used to reduce the cohesion of biofilms. In some embodiments, the compounds described herein are used to reduce the viscosity of biofilms. In some embodiments, the compounds described herein are used to reduce the adhesion of biofilms. In some embodiments, the compounds described herein are used to reduce the adhesion of mucus. In some embodiments, the compounds described herein are used to reduce mucin or mucus build-up. In some embodiments, the chemical interactions of the compounds described herein with biological systems vary with changes in the molecular weight or percent functionalization of the compounds described herein. In some embodiments, the chemical interactions of the compounds described herein with biological systems can be tuned by changing the molecular weight or percent functionalization of the compounds described herein.

Barrier to Inflammation Activation

Modulation of inflammation by polycationic functionalized polyglucosamines has been observed in the oral cavity after radiation induced inflammation and damage, in the GI tract after radiation, chemical or bacterial induced damage and inflammation and in dermal burns, in eyes after chemical injury. [Baker, 2014] Polycationic functionalized polyglucosamines associate with the glycocalyx (dermis and ophthalmologic) and mucosal interfaces (GI and oral) to modulate the activity of early inflammatory activators at the cell surface to mitigate continued inflammation activated at cell surfaces by damage associated molecular patterns (DAMP's) and pathogen associated molecular patterns (PAMP's). These DAMP's and PAMP's activate similar molecular pathways, primarily through Toll-like receptors (TLR's) of the innate immune system [Sonis, 2010; Piccinini, 2010] and in the lung. [Greene, 2005, Jiang, 2005] DNA in the pulmonary tree also contributes to inflammation through DAMPS. [Jounai, 2013] This pattern recognition by TLR's leads to downstream activation of chemokines, that produce additional inflammation through activation of neutrophils and production of reactive oxygen species. [Jounai, 2013; Bianchi, 2006]. Polycationic functionalized polyglucosamines are pluripotent like many cationic defensins [Chaly, 2000], in their roles at the cell surface, as its mechanism of action (MOA) appears to be moderation of TLR activation of both DAMPs and PAMPs at the cell surface, including IL-8 which is important in CF neutrophil activated inflammation [Devaney, 2003] and the reduction of bacterial ability to adhere to cellular surface sites. Because CF causes a mucosal immunodeficiency syndrome [Cohen, 2012], these effects observed by polycationic functionalized polyglucosamines in the lung are also applicable to the sinonasal passages [Gysin, 2000] and the GI tract [Kreda, 2014].

In some embodiments, the compounds described herein can be used to dampen dysregulated inflammation (e.g., in cystic fibrosis). In some embodiments, the compounds described herein can be used to disrupt mucus structure. In some embodiments, the compounds described herein can be used to provide airway clearance.

Diseases and Disorders

Exemplary diseases and disorders that can be treated using the methods described herein include those where the subject would benefit from an increase in mucociliary clearance.

Lung Diseases

The methods described herein can be used to treat or prevent lung diseases or disorders. Lung diseases refer to any problem in the lungs or pulmonary system, or that prevents the lungs or pulmonary system, from working properly. Lung diseases can affect the airways, air sacs (i.e., alveoli), or interstitium. Lung diseases can affect the airway, the lung tissue (e.g., the structure of the lung tissue), or the blood vessels (e.g., lung circulation diseases). Lung diseases include, but are not limited to. Acute Bronchitis. Acute Respiratory Distress Syndrome (ARDS), Asbestosis, Asthma, Bronchiectasis, Bronchiolitis, Bronchiolitis Obliterans Organizing Pneumonia (BOOP), Bronchopulmonary Dysplasia, Byssinosis, Chronic Bronchitis, Coccidioidomycosis (Cocci), COPD, Cryptogenic Organizing Pneumonia (COP), Cystic Fibrosis, Emphysema. Hantavirus Pulmonary Syndrome. Histoplasmosis, Human Metapneumovirus, Hypersensitivity Pneumonitis, Influenza, Lymphangiomatosis, Mesothelioma, Nontuberculosis *Mycobacterium*, Pertussis, Pneumoconiosis (Black Lung Disease). Pneumonia. Primary Ciliary Dyskinesia, Pulmonary Fibrosis, Pulmonary Vascular Disease, Respiratory Syncytial Virus, Sarcoidosis, Severe Acute Respiratory Syndrome. Silicosis, and Tuberculosis.

Lung diseases affecting the airways affect the tubes that carry oxygen and other gases into and out of the lungs. Diseases affecting the airways can affect a narrowing or blockage of the airways. Diseases affecting the airways include, but are not limited to, asthma, COPD, chronic bronchitis, emphysema, bronchiectasis, acute bronchitis, and cystic fibrosis. In asthma, the airways are persistently inflamed, and may occasionally spasm, causing wheezing and shortness of breath. Allergies, infections, or pollution can trigger the symptoms of asthma. Lung conditions such as COPD can affect an inability to exhale normally and cause difficulty breathing. A form of COPD, chronic bronchitis, is characterized by chronic productive cough. A form of COPD caused by lung damage allowing air to be trapped in the lungs is emphysema. Cystic fibrosis is also a lung disease affecting the airways.

Lung diseases affecting the air sacs include, but are not limited to, pneumonia, tuberculosis, emphysema, pulmonary edema, lung cancer, acute respiratory distress syndrome (ARDS), and pneumoconiosis. Pneumonia is an infection (e.g., bacterial infection) affecting the alveoli. A slowly progressing pneumonia caused by *Mycobacterium tuberculosis* is known as tuberculosis. Emphysema can limit airflow and affect airways, and typically results from damage to the fragile connections between alveoli. Pulmonary edema refers to fluid leakage from the small blood vessels of the lung and into the air sacs and the surrounding area. ARS refers to a severe, sudden injury to the lungs typically caused by a serious illness. Pneumoconiosis refers to a category of conditions caused by the inhalation of a substance that injures the lungs. Exemplary pneumoconiosis includes black lung disease from inhaled coal dust and asbestosis (from inhaled asbestos dust).

Lung diseases affecting the interstitium include interstitial lung disease (ILD) and pneumonias and pulmonary edema. ILD includes, but are not limited to, sarcoidosis, idiopathic pulmonary fibrosis, and autoimmune disease.

Improved lung function is provided by the methods described herein. Measurements typically used to assess lung function include:

Forced expiratory volume in 1 second (FEVi) refers to the volume exhaled during the first second of a forced expiratory maneuver started from the level of total lung capacity.

Forced inspiratory volume in 1 second (FIVi) refers to the volume that can be forcefully inhaled during the first second of a forced inspiratory maneuver started from residual volume.

Total lung capacity (TLC) refers to the volume of gas contained in the lung after a full inhalation. TLC is determined by factors including normal mental function; intact neuromuscular apparatus; normal shape, mobility, and elasticity of the thorax; normal elastic properties of the lung: and normal thoracic content.

In one embodiment, the methods described herein, e.g., methods comprising administering a soluble polyglucosamine or derivatized polyglucosamine (e.g., a soluble polyglucosamine or derivatized polyglucosamine described herein) is used to treat or prevent lung disease or disorders, e.g., a lung disease or disorder described herein. In some embodiments, the methods described herein can be used to treat or prevent bacterial infection, e.g., by the pulmonary or gastro bacteria listed in Tables 1 and 2.

TABLE 1

Exemplary pulmonary bacteria strains

| Strain (Pulmonary) | Characteristics |
|---|---|
| *Staphylococcus aureus* | Broadly infective, wounds, body fluids, tissue, pulmonary, highly multi-drug resistant strains including MRSA and mupirocin resistant MRSA |
| *Pseudomonas aeruginosa* | Causes pneumonia, primary pathogen in patients with cystic fibrosis, many MDR strains, forms thick biofilms |
| *Burkholdaria cepacia* genomvar cenocepatia | Virulent pathogen in lungs of patients with cystic fibrosis |
| *Acinetobacter baumannii* | Slow-growing, colonization, causes penumonia |
| *Streptococcus pneumoniae* | Aquatic bacterium, colonizes breathing and feeding tubes |
| *Stenotrophomonas maltophilia* | Similar to *pseudomonas*, pulmonary infections |
| *Burkholdaria cepacia* genomvar dolsa | Virulent pathogen in lungs of patients with cystic fibrosis |
| *Klebsiella pneumoniae* | Causes pneumonia and wound infections, many MDR strains |
| *Burkholdaria cepacia* complex | Virulent pathogen in lungs of patients with cystic fibrosis |

TABLE 2

Exemplary gastro bacteria strains

| Strain (gastro) | Description |
| --- | --- |
| Escherichia coli | Shiga-like toxin producer, such as O157:117 |
| Shigella flexneri | Shiga toxin producer |
| Salmonella typhimurium | Causes gastroenteritis, food poisoning |
| Clostridium difficile | Causes food poisoning, forms spores |
| Enterococcus faecalis | Vancomycin resistant, gastrointestinal |
| Helicobacter pylori | Gastrointestinal ulcers |
| Bacillus subtilis | Spore former |
| Listeria monocytogenes | Intracellular pathogen |
| Campylobacter jejuni | Causes food poisoning, non-spore former |
| Staphylococcus aureus | Gastroenteritis |
| Klebsiella pneumoniae | Causes pneumonia, may drug resistant strains |

Cystic Fibrosis

The methods described herein can be used to treat or prevent complications of cystic fibrosis in a subject. For example, liquid or solid particulate compositions comprising soluble polyglucosamines or derivatized polyglucosamines described herein can be used to treat or prevent complications of cystic fibrosis, e.g., lung infections or respiratory tract congestion, in a subject. Treatment or prevention includes administration of soluble polyglucosamines or derivatized polyglucosamines alone or in combination with drugs or treatments described below.

Cystic Fibrosis (also known as CF, mucovoidosis, or mucoviscidosis) is a hereditary disease affecting the exocrine (mucous) glands of the lungs, liver, pancreas, and intestines, causing progressive disability due to multisystem failure. CF is caused by a mutation in the gene cystic fibrosis transmembrane conductance regulator (CFTR). The product of this gene is a chloride ion channel important in creating sweat, digestive juices and mucus. CF is considered an autosomal recessive disease.

Symptomatic diseases and complications associated with CF include. e.g., lung and sinus diseases; gastrointestinal, liver and pancreatic diseases; endocrine diseases; and infertility. For example, lung disease results from clogging the airways due to mucosa buildup and resulting inflammation. Some of these symptoms occur when bacteria that normally inhabit the thick mucus grow out of control and cause pneumonia. In later stages of CF, changes in the architecture of the lung further exacerbate chronic difficulties in breathing. Other symptoms include coughing up blood (hemoptysis), changes in the major airways in the lungs (bronchiectasis), high blood pressure in the lung (pulmonary hypertension), heart failure, difficulties getting enough oxygen to the body (hypoxia), respiratory failure requiring support with breathing masks such as bilevel positive airway pressure machines or ventilators, allergic bronchopulmonary aspergillosis, and infection with *Mycobacterium avium* complex (MAC). Mucus in the paranasal sinuses is equally thick and may also cause blockage of the sinus passages, leading to infection. This may cause facial pain, fever, nasal drainage, and headaches. Individuals with CF may develop overgrowth of the nasal tissue (nasal polyps) due to inflammation from chronic sinus infections. These polyps can block the nasal passages and increase breathing difficulties.

Cystic fibrosis causes thick, adherent mucus to build up in the lungs, sinuses, digestive tract and pancreas. This mucus abnormality clogs airways and can cause life-threatening lung infections. People with CF are often chronically or recurrently infected with bacteria in their lungs, which in the absence of mucocilairy clearance are a fertile breeding ground for many types of bacteria, in particular *Pseudomonas aeruginosa*. Bacteria that do not adhere to normal mucus or tissues are removed by normal airway clearance mechanisms; however, the viscous mucus in CF patients limits mucociliary clearance and facilitates biofilm formation, initiating a cascade that includes dysregulated inflammation and ultimately end organ dysfunction. While many efforts target the genetic defect (the cystic fibrosis transmembrane conductance regulator (CFTR) protein) that causes absent chloride and bicarbonate transport, treatments for the wide range of genetic defects identified in CF patients will take time, and may not address individuals with severe established disease who exhibit significant mucus impaction. Moreover, despite therapeutic advances, the median age of death is 37 years and is associated with considerable morbidity.

Current therapies intended to augment mucociliary clearance address components in the mucus, such as dornase alpha (Pulmozyme®), which is a DNAse and osmotic therapies that draw fluid from the lungs to dilute mucus and enhance its transport. While these standards provide do modestly improve lung function, they do not directly target the mucus for their mechanism of action. They are also limited in the magnitude of their activity and by the presence of recalcitrant biofilms, which may block their access to the components in the mucus they target or to the airway surfaces. Topical, inhaled and systemic antibiotics are used to treat the bacterial infection, but have difficulty penetrating dense biofilms and mucus, and rarely eradicate organisms in the majority with established disease. Polycationic functionalized polyglucosamines represent a novel treatment to directly target the components of mucus and the components of biofilms, to reduce the viscosity of mucus and the cohesion of biofilms in the lungs, enhancing airway clearance, and potentially augmenting the activity of standard therapeutic antibiotics to provide substantial clinical benefit. Polycationic functionalized polyglucosamines also target the surface glycocalyx reducing the adhesion of bacteria, of biofilms and of mucus to the pulmonary surface, also enabling enhancement of mucociliary clearance. Successful development of polycationic functionalized polyglucosamines for CF patients could provide the basis for treatment of other lung diseases with abnormal mucus or delayed mucociliary clearance.

Complications of CF, e.g., lung diseases, can be treated or prevented using soluble polyglucosamines or derivatized polyglucosamines described herein, in combination with (e.g., in series with, before, or after) one or more of agents or therapeutics. Exemplary agents to treat complications of CF, e.g., lung diseases include antibiotics such as xylitol, vancomycin, tobramycin, meropenem, ciprofloxacin, or piperacillin, administered e.g., intravenously. Inhaled therapy with antibiotics such as tobramycin, colistin or aztreonam can also be given to improve lung function by impeding the growth of colonized bacteria. Oral antibiotics such as ciprofloxacin or azithromycin can be given to help prevent infection or to control ongoing infection. Other methods to treat lung disease include, e.g., chest physiotherapy (CPT), Biphasic Cuirass Ventilation, or aerosolized medications (e.g., DNase (e.g., dornase (Pulmozyme®)), hypertonic saline, N-acetylcysteine, albuterol, or ipratropium). In some embodiments, the administrations of a combination of agents and therapeutics are spaced sufficiently close together such that the activity e.g., the efficacy, effectiveness) of one or both agents is potentiated. In some embodiments, the administrations of a combination of agents and therapeutics are spaced sufficiently close together such that a synergistic effect is achieved.

In one embodiment, the methods described herein. e.g., methods comprising administering a soluble polyglucosamine or derivatized polyglucosamine (e.g., a soluble polyglucosamine or derivatized polyglucosamine described herein) is used to treat cystic fibrosis or a symptom of cystic fibrosis.

Respiratory Tract Infections

The methods described herein can be used to treat or prevent respiratory tract infections in a subject. For example, liquid or solid particulate compositions comprising soluble polyglucosamines or derivatized polyglucosamines described herein can be used to treat or prevent respiratory tract infections, e.g., respiratory tract bacterial infections, in a subject. Treatment or prevention includes administration of soluble polyglucosamines or derivatized polyglucosamines alone or in combination with drugs or treatments described below.

Respiratory tract infections can be caused by e.g., bacteria, viruses, parasites or fungi. Exemplary respiratory tract bacterial infections include upper respiratory tract infections such as sinusitis, pharyngitis, epiglottis, laryngitis, tracheitis, and rhinitis; and lower respiratory tract infections such as bronchitis and pneumonia.

Symptoms of respiratory tract infections include, e.g., pain, inflammation, fever, fatigue, lack of breath, nausea, diarrhea, cough, and death.

Respiratory tract infections can be treated or prevented using soluble polyglucosamines or derivatized polyglucosamines described herein, in combination with one or more of agents or therapeutics. Exemplary agents and therapeutics to treat respiratory tract infections includes systemic antibiotics, inhaled antibiotics, anti-inflammatory agents and steroids, mucolytic agents, and supplemental oxygen. In some embodiments, the administrations of a combination of agents and therapeutics are spaced sufficiently close together such that the activity (e.g., the efficacy, effectiveness) of one or both agents is potentiated. In some embodiments, the administrations of a combination of agents and therapeutics are spaced sufficiently close together such that a synergistic effect is achieved.

In one embodiment, the methods described herein, e.g., methods comprising administering a soluble polyglucosamine or derivatized poly glucosamine (e.g., a soluble polyglucosamine or derivatized polyglucosamine described herein) is used to treat or prevent a respiratory tract infection or symptom of a respiratory tract infection.

Gastrointestinal Tract Infections

The methods described herein can be used to treat or prevent gastrointestinal tract infections in a subject. For example, liquid or solid particulate compositions comprising soluble polyglucosamines or derivatized polyglucosamines described herein can be used to treat or prevent gastrointestinal tract infections, e.g., gastrointestinal tract bacterial infections, in a subject. Treatment or prevention includes administration of soluble polyglucosamines or derivatized polyglucosamines alone or in combination with drugs or treatments described below.

Gastrointestinal tract infections can be caused by e.g., bacteria (e.g., enteric bacteria), viruses, parasites or fungi. Exemplary gastrointestinal tract bacterial infections include noninflammatory gastroenteritis caused by e.g., *Staphylococcus aureus, Bacillus cereus, Clostridium perfringens, Clostridium difficile* or *Clostridium botulinum*; inflammatory gastroenteritis caused by e.g., *Vibrio cholerae.* Enterotoxigenic (ETEC) *Escherichia* coi. Enteropathogenic (EPEC) *Escherichia coli*, Enteroaggregative (EAggEC) *Escherichia coli, Clostridium difficile, Vibrio parahemolyticus*, or *Bacillus anthracis*: or invasive gastroenteritis caused by e.g., *Shigella* sp., *Salmonella* sp., *Campylobacter jejuni*, Enteroinvasive (EIEC) *Escherichia coli*, Enterohemorrhagic (EHEC) *Escherichia coli, Vibrion vulnificus, Yersinia* sp., *Francisella tularensis*, or *Helicobacter pylori.*

Symptoms of gastrointestinal tract infections include, e.g., diarrhea, vomiting, abdominal pain, cramps, fecal leukocytes, fever, dysentery, and/or blood in stool.

Gastrointestinal tract infections can be treated or prevented using soluble polyglucosamines or derivatized polyglucosamines described herein, in combination with one or more of agents or therapeutics. Exemplary agents and therapeutics to treat gastrointestinal tract infections includes rehydration, dietary therapy, probiotics, zinc, pharmacologic therapy (e.g., antibiotics (e.g., fluoroquinolone, metronidazole or vancomycin), antidiarrheal agents (e.g., loperamide or bismuth subsalicylate (BSS)), or antiemetic drugs (e.g., ondansetron or metoclopramide)). In some embodiments, the administrations of a combination of agents and therapeutics are spaced sufficiently close together such that the activity (e.g., the efficacy, effectiveness) of one or both agents is potentiated. In some embodiments, the administrations of a combination of agents and therapeutics are spaced sufficiently close together such that a synergistic effect is achieved.

In one embodiment, the methods described herein, e.g., methods comprising administering a soluble polyglucosamine or derivatized polyglucosamine (e.g., a soluble polyglucosamine or derivatized polyglucosamine described herein) is used to treat or prevent a gastrointestinal tract infection or symptom of a gastrointestinal tract infection.

Necrotizing Entercolitis (NEC)

Necrotizing Entercolitis (NEC) is inflammation and death of intestinal tissue typically involving the lining of the intestine or the entire thickness of the intestine. In severe cases, the intestine may perforate and a hole develops in the intestinal wall. In cases when a hole develops in the intestinal wall, bacteria found in the intestine can leak into the abdomen and cause widespread infection. NEC is most common in premature infants, typically developing within two weeks of birth. However. NEC may occur up to three months after birth. Symptoms of NEC includes bloody stool, diarrhea, constipation, chills or fever, poor feeding, and vomiting. Current treatment options include intravenous feeding, antibiotics, and a tube that goes in the nose to the stomach to remove extra fluids and gas from the intestine.

In one embodiment, the methods described herein, e.g., methods comprising administering a soluble polyglucosamine or derivatized polyglucosamine (e.g., a soluble polyglucosamine or derivatized polyglucosamine described herein) is used to treat or prevent necrotizing entercolitis or a symptom of necrotizing entercolitis.

Short Bowel Syndrome (SBS)

Short Bowel Syndrome (SBS) is a malabsorption disorder caused by the surgical removal of the small intestine or due in rare cases to complete dysfunction of a large segment of the bowel. SBS is typically acquired, but some children are born with a congenital short bowel. SBS generally does not develop unless more than two thirds of the small intestine has been removed. SBS is usually caused by surgery for Crohn's disease, volvulus, tumors of the small intestine, injury or trauma to the small intestine, necrotizing enterocolitis, bypass surgery to treat obesity, or other surgeries to remove diseases or damaged portions of the small intestine.

In one embodiment, the methods described herein, e.g., methods comprising administering a soluble polyglucosamine or derivatized polyglucosamine (e.g., a soluble polyglucosamine or derivatized polyglucosamine described herein) is used to treat or prevent short bowel syndrome or a symptom of short bowel syndrome.

Distal Intestinal Obstructive Syndrome (DIOS)

Distal intestinal obstruction syndrome (DIOS) often occurs in individuals with cystic fibrosis and involves the blockage of intestines by thickened stool. In individuals with cystic fibrosis, mucus builds up along the intestinal tract and slows the emptying of food. The resultant build-up of stool behind the mucus-filled area causes blockage. DIOS is similar to constipation (e.g., there is a back-up of stool in the digestive tract), but the back-up of stool is higher up in the intestines. DIOS in newborn infants is also referred to as meconium ileus equivalent. Symptoms of DIOS include abdominal pain, vomiting, and palpable mass in the abdomen. DIOS treatment typically requires surgery to relieve the obstruction, especially when there is sign of bowel rupture. More conservative approaches may be attempted to treat DIOS, including restricting oral intake, placement of a nasogastric tube for decompression of the stomach and proximal intestines, and laxative and enema administration. Individuals suffering from DIOS tend to have repeat episodes, often requiring maintenance therapy with pancreatic enzyme replacement and stool softeners.

In one embodiment, the methods described herein, e.g., methods comprising administering a soluble polyglucosamine or derivatized polyglucosamine (e.g., a soluble polyglucosamine or derivatized polyglucosamine described herein) is used to treat or prevent distal intestinal obstruction syndrome or a symptom of distal intestinal obstruction syndrome.

Meconium Ileus

Meconium ileus is a condition where a baby's first stool (i.e., meconium) is blocking the last part of the small intestine. Meconium ileus can happen when the meconium is thicker and more sticky than normal. The small intestine can become enlarged, loops of small intestine may distend, or push out, the abdomen. Below the blockage, the large intestine is narrow. It may be empty, or may hold small pellets of dried meconium or plugs of mucus from the lining of the intestine. Almost all babies with meconium ileus have cystic fibrosis (CF). CF makes certain fluids and mucus in the body thicker than normal.

In one embodiment, the methods described herein, e.g., methods comprising administering a soluble polyglucosamine or derivatized polyglucosamine (e.g., a soluble polyglucosamine or derivatized polyglucosamine described herein) is used to treat or prevent meconium ileus or a symptom of meconium ileus.

Compounds and Compositions

Soluble Polyglucosamines and Polyglucosamines Derivatives

Compounds and compositions containing a soluble polyglucosamine or a polyglucosamine derivative can be used in the methods described herein. For example, a compound described herein can be used to treat a subject described herein. In some embodiments, a subject is suffering from a condition described herein. Exemplary conditions include those where the subject would benefit from an increase in mucociliary clearance. The compounds and compositions can be administered as described herein. For example, a compound can be administered to a biofilm in a subject, for example in the lung or pulmonary system, or digestive system of the subject.

Polyglucosamines can be derived from chitin or chitosan. Chitosan is an insoluble polymer derived from the deacetylation of chitin, which is a polymer of N-acetylglueosarnine, that is the main component of the exoskeletons of crustaceans (e.g., shrimp, crab, lobster). Chitosan is generally a $\beta(1\rightarrow4)$ polyglucosamme that is less than 50% acetylated while chitin is generally considered to be more than 50% acetylated. Polyglucosamines are also found in various fungi and arthropods. Synthetic sources and alternate sources of $\beta(1\rightarrow4)$ polyglucosamines may serve as the starting material for polyglucosamine derivatives. Polyglucosamines, as opposed to polyacetylglucosamines, are defined herein to be less than 50% acetylated, if greater than 50% of the amino groups are acetylated, the polymer is considered a polyacetylglucosamine. As referred to herein and unless specified otherwise, the "molecular weight" of a soluble polyglucosamine or a polyglucosamine derivative will be understood by one of skill in the art to refer to the average molecular weight of a soluble polyglucosamine or a polyglucosamine derivative.

A soluble polyglucosamine described herein refers to a neutral pH, water soluble polyglucosamine or polyglucosamine that is not derivatized on the hydroxyl or amine moieties other than with acetyl groups. A soluble polyglucosamine is comprised of glucosamine and acetylglucosamine monomers. Generally, a water soluble polyglucosamine (at neutral pH) has a molecular weight of less than or equal to about 5,000 kDa and a degree of deacetylation equal to or greater than 80%.

A polyglucosamine derivative described herein is generated by functionalizing the free hydroxyl or amine groups with positively charged or neutral moieties. The percent of functionalization is defined as the total percent of monomers on the polyglucosamine backbone that have been functionalized with a positively charged or neutral moiety. The degrees of deacetylation and functionalization impart a specific charge density to the functionalized polyglucosamine derivative. The resulting charge density affects solubility and effectiveness of treatment. Thus, in accordance with the present invention, the degree of deacetylation, the functionalization and the molecular weight must be optimized for optimal efficacy. The polyglucosamine derivatives described herein have a number of properties which are advantageous, including solubility at physiologic (neutral) pH. As used herein, polycationic functionalized polyglucosamines refers to a polyglucosamine derivative functionalized with positively charged moieties. In some embodiments, the polycationic functionalized polyglucosamines is poly (acetyl, arginyl) glucosamine (PAAG).

In some embodiments, the polyglucosamine derivative is soluble up to a pH of 10. In some embodiments, the average molecular weight of the polyglucosamine derivative is between 5 and 1,000 kDa. In some embodiments, the average molecular weight of the polyglucosamine derivative is between 15 and 1.000 kDa. In some embodiments, the average molecular weight of the polyglucosamine derivative is between 20 and 350 kDa. In some embodiments, the average molecular weight of the polyglucosamine derivative is between 20 and 150 kDa. In some embodiments, the average molecular weight of the polyglucosamine derivative is between 20 and 120 kDa. In some embodiments, the average molecular weight of the polyglucosamine derivative is between 30 and 120 kDa. In some embodiments, the average molecular weight of the polyglucosamine derivative is between 50 and 100 kDa. In some embodiments, the average molecular weight of the polyglucosamine derivative is between 70-120 kDa. In some embodiments, the average molecular weight of the polyglucosamine derivative is between 50-90 kDa. The polyglucosamine derivative described herein is soluble at pH 2 to pH 11.

In some embodiments, the polyglucosamine derivative described herein is solubilized in aqueous solution comprising glycerol between 1-2% v/v. In some embodiments, the polyglucosamine derivative described herein is solubilized in aqueous solution comprising glycerol between 1.2-1.8% v/v. In some embodiments, the polyglucosamine derivative described herein is solubilized in aqueous solution comprising glycerol between 1.2-1.6% v/v. In some embodiments, the polyglucosamine derivative described herein is solubilized in aqueous solution comprising glycerol between 1.2-1.6% v/v. In some embodiments the polyglucosamine derivative described herein is solubilized in aqueous solution comprising glycerol between 1.2-1.4% v/v, in some embodiments, the polyglucosamine derivative described herein is solubilized in aqueous solution comprising glycerol between 1.3-1.4% v/v. In some embodiments, the polyglucosamine derivative described herein is solubilized in aqueous solution comprising glycerol around 1.38% v/v.

In some embodiments, the polyglucosamine derivative described herein is solubilized in aqueous solution comprising glycerol. In some embodiments, the solution comprises particles of 1-5 microns in mean particle size diameter. In some embodiments, the solution can be nebulized.

Polyglucosamines with any degree of deacetylation (DDA) greater than 50% are used in the present invention, with functionalization between 2% and 50% of the total monomers on the polyglucosamine backbone. The degree of deacetylation determines the relative content of free amino groups to total monomers in the polyglucosamine polymer. Methods that can be used for determination of the degree of deacetylation of polyglucosamine include, e.g., ninhydrin test, linear potentiometric titration, near-infrared spectroscopy, nuclear magnetic resonance spectroscopy, hydrogen bromide titrimetry, infrared spectroscopy, and first derivative UV-spectrophotometiy. Preferably, the degree of deacetylation of a soluble polyglucosamine or a derivatized polyglucosamine described herein is determined by quantitative infrared spectroscopy.

Percent functionalization by active derivitization of the amines is determined relative to the total number of monomers on the polyglucosamine polymer. Preferably, the percent functionalization of a derivatized polyglucosamine described herein is determined by H-NMR or quantitative elemental analysis. The degrees of deacetylation and functionalization impart a specific charge density to the functionalized polyglucosamine derivative. The resulting charge density affects solubility, and strength of interaction with tissue, biofilm components and bacterial membranes. The molecular weight is also an important factor in a derivatized polyglucosamine's mucoadhesivity and biofilm disrupting capability. Thus, in accordance with the present invention, these properties must be optimized for optimal efficacy. Exemplary polyglucosamine derivatives are described in U.S. Pat. No. 8,119,780, which is incorporated herein by reference in its entirety.

The polyglucosamine derivatives described herein have a range of polydispersity index (PDI) between about 1.0 to about 2.5. As used herein, the polydispersity index (PDI), is a measure of the distribution of molecular weights in a given polymer sample. The PDI calculated is the weight averaged molecular weight divided by the number averaged molecular weight. This calculation indicates the distribution of individual molecular weights in a batch of polymers. The PDI has a value always greater than 1, but as the polymer chains approach uniform chain length, the PDI approaches unity (1). The PDI of a polymer derived from a natural source depends on the natural source (e.g. chitin or chitosan from crab vs. shrimp vs. fungi) and can be affected by a variety of reaction, production, processing, handling, storage and purifying conditions. Methods to determine the polydispersity include, e.g., gel permeation chromatography (also known as size exclusion chromatography); light scattering measurements; and direct calculation from MALDI or from electrospray mass spectrometry. Preferably, the PDI of a soluble polyglucosamine or a derivatized polyglucosamine described herein is determined by HPLC and multi angle light scattering methods.

The polyglucosamine derivatives (i.e., derivatized polyglucosamines) described herein have a variety of selected average molecular weights that are soluble at neutral and physiological pH, and include for the purposes of this invention average molecular weights ranging from 5-1,000 kDa. Derivatized polyglucosamines are soluble at pH up to about 10. Embodiments described herein are feature medium range average molecular weight of derivatized polyglucosamines (20-150 kDa, e.g., from about 20 to about 150 kDa). In some embodiments, the average molecular weight of the derivatized polyglucosamine is between 15 and 1,000 kDa. In some embodiments, the average molecular weight of the derivatized polyglucosamine is between 20 and 150 kDa. In some embodiments, the average molecular weight of the derivatized polyglucosamine is between 20 and 120 Da. In some embodiments, the average molecular weight of the polyglucosamine derivative is between 30 and 120 kDa. In some embodiments, the average molecular weight of the polyglucosamine derivative is between 50 and 100 kDa. In some embodiments, the average molecular weight of the functionalized polyglucosamine is between 20 and 80 kDa.

The functionalized polyglucosamine derivatives described herein include the following:

(A) Polyglucosamine-arginine compounds;

(B) Polyglucosamine-natural amino acid derivative compounds;

(C) Polyglucosamine-unnatural amino acid compounds;

(D) Polyglucosamine-acid amine compounds.

(E) Polyglucosamine-guanidine compounds; and (F) Neutral polyglucosamine derivative compounds.

(A) Polyglucosamine-Arginine Compounds

In some embodiments, the present invention is directed to polyglucosamine-arginine compounds, where the arginine is bound through a peptide (amide) bond via its carbonyl to the primary amine on the glucosamines of polyglucosamine:

wherein each $R^1$ is independently selected from hydrogen, acetyl, and a group of the following formula:

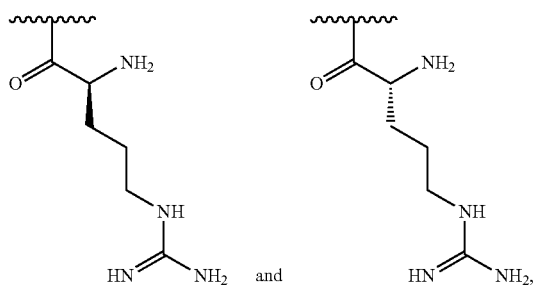 [SMILES: *C(=O)[C@@H](N)CCCNC(=N)N ; *C(=O)[C@H](N)CCCNC(=N)N]

or a racemic mixture thereof,
wherein at least 25% of $R^1$ substituents are H, at least 1% are acetyl, and at least 2% are a group of the formula shown above.

In some embodiments, a polyglucosamine-arginine compound is of the following formula

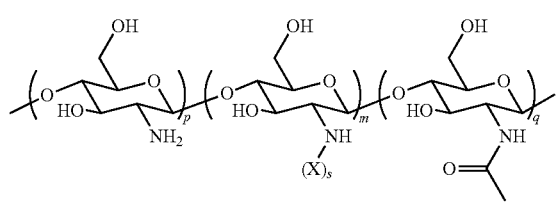

where m is 0.02-0.50; q is 0.50-0.01; s is 1; p+q+m=1; the percent degree of functionalization is m·100%; and X is selected from the group consisting of:

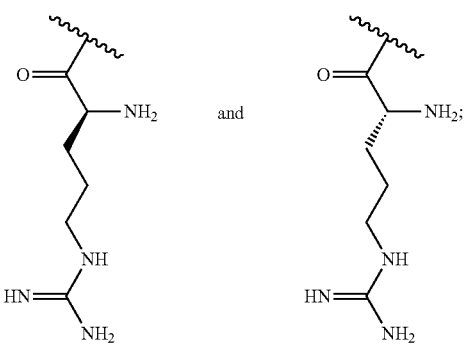 [SMILES: *C(=O)[C@@H](N)CCCNC(=N)N ; *C(=O)[C@H](N)CCCNC(=N)N]

wherein the preparation is substantially free of compounds having a molecular weight of less than 5 kDa. In some embodiments, polyglucosamine-arginine compound is poly (acetyl, arginyl) glucosamine (PAAG).

(B) Polyglucosamine-Natural Amino Acid Derivative Compounds

In some embodiments, the present invention is directed to polyglucosamine-natural amino acid derivative compounds, wherein the natural amino acid may be histidine or lysine. The amino is bound through a peptide (amide) bond via its carbonyl to the primary amine on the glucosamines of polyglucosamine;

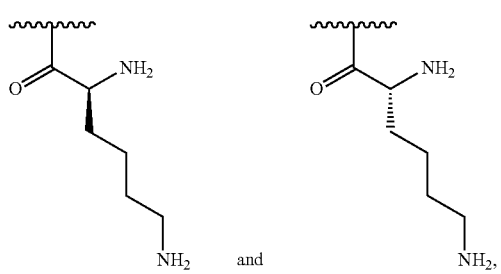

wherein each $R^1$ is independently selected from hydrogen, acetyl, and a group of the following formula:

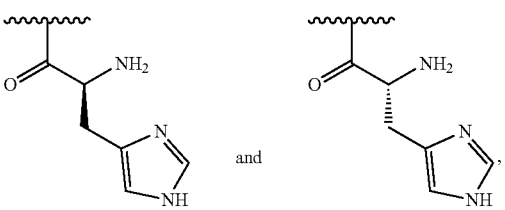 [SMILES: *C(=O)[C@@H](N)Cc1c[nH]cn1 ; *C(=O)[C@H](N)Cc1c[nH]cn1]

or a racemic mixture thereof, wherein at least 25% of $R^1$ substituents are H, at least 1% are acetyl, and at least 2% are a group of the formula shown above; or a group of the following formula:

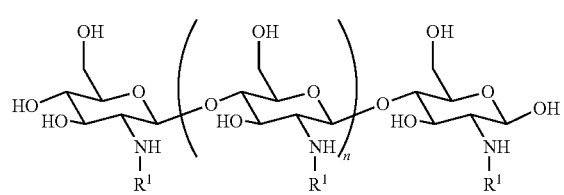

or a racemic mixture thereof, wherein at least 25% of $R^1$ substituents are H, at least 1% are acetyl, and at least 2% are a group of the formula shown above.

(C) Polyglucosamine-Unnatural Amino Acid Compounds

In some embodiments, the present invention is directed to polyglucosamine-unnatural amino acid compounds, where the unnatural amino acid is bound through a peptide (amide) bond via its carbonyl to the primary amine on the glucosamines of poly glucosamine:

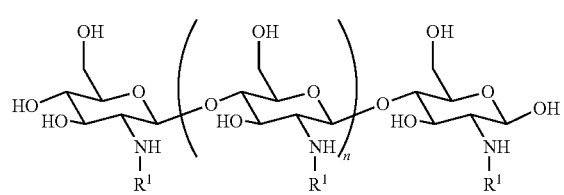

wherein each $R^1$ is independently selected from hydrogen, acetyl, and a group of the following formula:

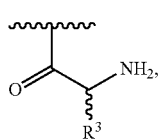

wherein R³ is an unnatural amino acid side chain, and wherein at least 25% of R¹ substituents are H, at least 1% are acetyl, and at least 2% are a group of the formula shown above.

Unnatural amino acids are those with side chains not normally found in biological systems, such as ornithine (2,5-diaminopentanoic acid). Any unnatural amino acid may be used in accordance with the invention. In some embodiments, the unnatural amino acids coupled to polyglucosamine have the following formulae:

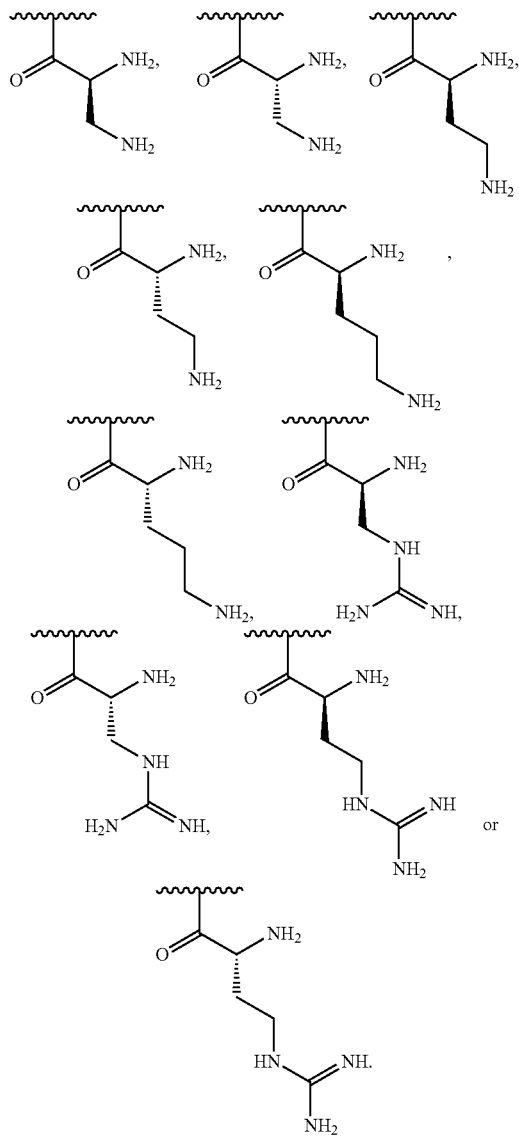

(D) Polyglucosamine-Acid Amine Compounds

In some embodiments, the present invention is directed to polyglucosamine-acid amine compounds, or their guanidylated counterparts. The acid amine is bound through a peptide (amide) bond via its carbonyl to the primary amine on the glucosamines of polyglucosamine:

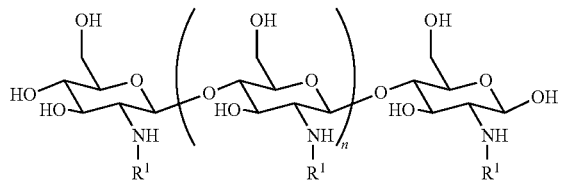

wherein each R¹ is independently selected from hydrogen, acetyl, and a group of the following formula:

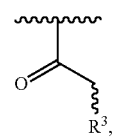

wherein R³ is selected from amino, guanidino, and C1-C6 alkyl substituted with an amino or a guanidino group, wherein at least 25% of R¹ substituents are H, at least 1% are acetyl, and at least 2% are a group of the formula shown above In some embodiments, R¹ is selected from one of the following:

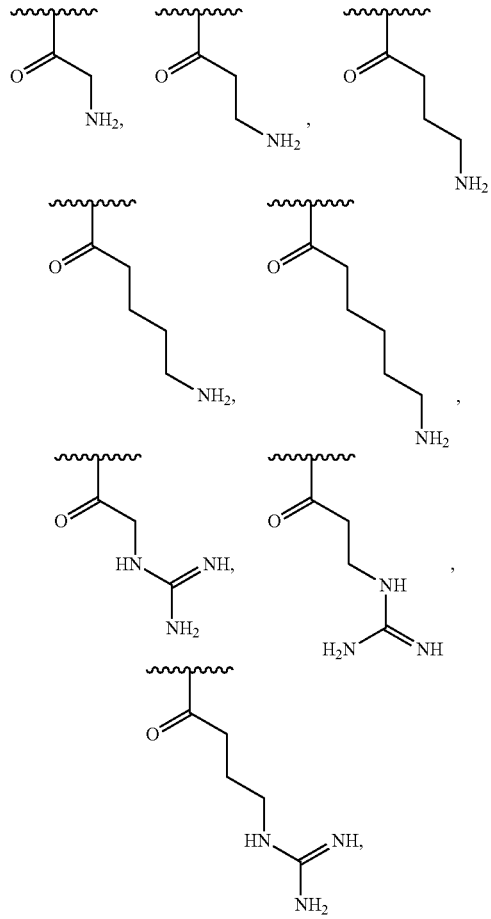

-continued

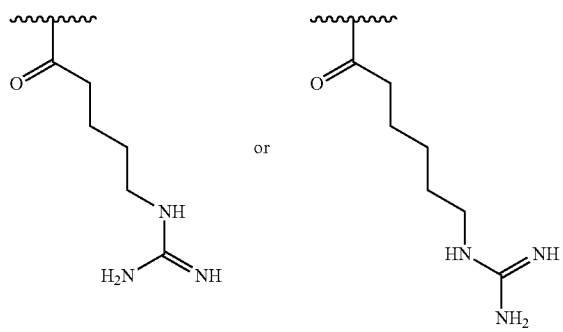

(F) Neutral Polyglucosamine-Guanadine Derivative Compounds

In some embodiments, the present invention is directed to polyglucosamine-guanidine compounds.

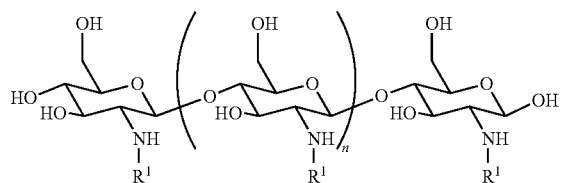

wherein each $R^1$ is independently selected from hydrogen, acetyl, and a group in which $R^1$, together with the nitrogen to which it is attached, forms a guanidine moiety; wherein at least 25% of $R^1$ substituents are H, at least 1% are acetyl, and at least 2% form a guanidine moiety together with the nitrogen to which it is attached.

(F) Neutral Polyglucosamine Derivative Compounds

In some embodiments, the present invention is directed to neutral polyglucosamine derivative compounds. Exemplary neutral polyglucosamine derivative compounds include those where one or more amine nitrogens of the polyglucosamine have been covalently attached to a neutral moiety such as a sugar:

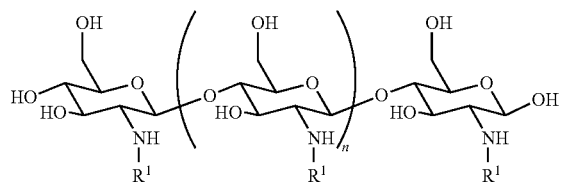

wherein each $R^1$ is independently selected from hydrogen, acetyl, and a sugar (e.g., a naturally occurring or modified sugar) or an a-hydroxy acid. Sugars can be monosaccharides, disaccharides or polysaccharides such as glucose, mannose, lactose, maltose, cellubiose, sucrose, amylose, glycogen, cellulose, gluconate, or pyruvate. Sugars can be covalently attached via a spacer or via the carboxylic acid, ketone or aldehyde group of the terminal sugar. Examples of oc4iydroxy acids include glycolic acid, lactic acid, and citric acid. In some preferred embodiments, the neutral polyglucosamine derivative is polyglucosamine-lactobionic acid compound or polyglucosamine-glycolic acid compound. Exemplary salts and coderivatives include those known in the art, for example, those described in US 2007/0281904, the contents of which is incorporated by reference in its entirety.

Combination Treatment

In some embodiments a soluble polyglucosamine or polyglucosamine derivative is administered to a subject in combination with another agent, such as an additional therapeutic agent. Additional therapeutic agents are described herein. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the combination treatment provides potentiation of one or more compound or agent being administered to the subject. Potentiation, as used herein, refers to an enhancement of one agent by another so that the combined effect is greater than the sum of the effects of each one alone. In some embodiments, a soluble polyglucosamine or derivatized polyglucosamine can be used in combination with an anti-bacterial agent to improve lung function. For example, a soluble polyglucosamine or derivatized polyglucosamine can be administered to a subject in combination with an anti-bacterial agent to improve lung function (e.g., to treat a lung disease or disorder as described herein). The soluble polyglucosamine or derivatized polyglucosamine can result in potentiation of an anti, bacterial agent, e.g., enhance the effect of the soluble polyglucosamine or derivatized polyglucosamine or an anti-bacterial agent. In some embodiments, the soluble polyglucosamine or derivatized polyglucosamine can result in potentiation of an anti-bacterial agent, so that the combination of the soluble polyglucosamine or derivatized polyglucosamine and the anti-bacterial agent can improve lung function (e.g., imparts an anti-bacterial effect that is) greater than either the soluble polyglucosamine or derivatized polyglucosamine alone, or the anti-bacterial agent alone. The combinations of a soluble polyglucosamine or derivatized polyglucosamine and an antibacterial agent can also result in a bactericidal effect that is greater than the sum of the effects of each agent when administered alone. In some embodiments, the administrations of a combination of agents and therapeutics are spaced sufficiently close together such that the activity (e.g., efficacy, effectiveness) of one or both agents is potentiated. The combinations of a soluble polyglucosamine or derivatized polyglucosamine and an antibacterial agent can also result in a synergistic bactericidal effect.

In some embodiments, the combination of a soluble polyglucosamine or derivatized polyglucosamine and a non-fermentable sugar (e.g., sorbitol or xylitol) can improve lung function greater than either the soluble polyglucosamine or derivatized polyglucosamine in the absence of the non-fermentable sugar, or the non-fermentable sugar in the absence of the soluble polyglucosamine or derivatized polyglucosamine. In some embodiments, the combination of a soluble polyglucosamine or derivatized polyglucosamine and a non-fermentable sugar (e.g., sorbitol or xylitol) can improve lung function greater than either the soluble polyglucosamine or derivatized polyglucosamine alone, or the non-fermentable sugar alone. In some embodiments, a non-fermentable sugar (e.g., sorbitol or xylitol) potentiates the biofilm remove activity of a compound as described herein, e.g., a soluble polyglucosamine or derivatized polyglucosamine (e.g., poly (acetyl, arginyl) glucosamine, or PAAG).

Antibacterials

The compositions and compounds described herein (e.g., soluble polyglucosamines or derivatized polyglucosamines) can be used in combination with one or more of antibiotics, to treat one or more diseases and conditions described herein. General classes of antibiotics include. e.g., aminoglycosides, bacitracin, beta-lactam antibiotics, cephalosporins, chloramphenicol glycopeptides, macrolides, lincosamides, penicillins, quinolones, rifampin, glycopeptide, tetracyclines, trimethoprim and sulfonamides. In some embodiments, the administrations of a combination of agents and therapeutics are spaced sufficiently close together such that a synergistic effect is achieved.

Exemplary antibiotics within the classes recited above are provided as follows. Exemplary aminoglycosides include Streptomycin, Neomycin, Framycetin, Parpmycin, Ribostamycin, Kanamycin, Amikacin, Dibekacin, Tobramycin, Hygromycin B, Spectinomycin. Gentamicin. Netilmicin, Sisomicin, Isepamicin, Verdamicin, Amikin, Garamycin, Kantrex, Netromycin, Nebcin, and Hmnatin, Exemplary carbacephems include Loracarbef (Lorabid), Exemplary carbapenems include Ertapenem, Invanz, Doripenem, Finibax, Imipenem/Cilastatin, Primaxin, Meropenem, and Merrem, Exemplary cephalosporins include Cefadroxil, Durisef, Cefazolin, Ancef, Cefalotin, Cefalothin, Keflin, Cefalexin, Keflex, Cefaclor, Ceclor, Cefamandole, Mandole, Cefoxitin, Mefoxin, Cefprozill, Cefzil, Cefuroxime, Ceftin, Zinnat, Cefixime, Suprax, Cefdinir, Omnicef, Cefditoren, Spectracef, Cefoperazone, Cefobid, Cefotaxime, Claforan, Cefpodoxime, Fortaz, Ceftibuten, Cedax, Ceftizoxime, Cefiriaxone, Rocephin, Cefepime, Maxipime, and Ceftrobriprole, Exemplary glycopeptides include Dalbavancin, Oritavancin, Teicoplanin, Vancomycin, and Vancocin, Exemplary macrolides include Azithromycin, Sithromax, Sunamed, Zitrocin, Clarithromycin, Biaxin, Dirithromycin, Erythromycin, Erythocin, Erythroped, Roxithromycin, Troleandomycin, Telithromycin, Ketek, and Spectinomycin, Exemplary monobactams include Aztreonam, Exemplary penicillins include Amoxicillin, Novamox, Aoxil, Ampicillin, Alocillin, Carbenicillin, Coxacillin, Diloxacillin, Flucloxacillin Floxapen, Mezlocillin, Methicillin, Nafcillin, Oxacillin, Penicillin, and Ticarcillin, Exemplary polypeptides include Bacitracin, Colistin, and Polymyxin B, Exemplary quiniolones include Ciproflaxin, Cipro, Ciproxin, Ciprobay, Enoxacin, Gatifloxacin, Tequin, Levofloxacin, Levaquin, Lomefloxacin, Moxifloxacin, Avelox, Norfloxacin, Noroxin, Ofloxacin, Ocuflox, Trovafloxacin, and Trovan, Exemplary sulfonamides include Mefenide, Prontosil (archaic), Sulfacetamide, Sulfamethizole, Sulfanilamide (archaic), Sulfasalazine, Sulfisoxazole, Trimethoprim, Trimethoprim-Sulfamethoxazole (co-trimoxazole), and Bactrim, Exemplary tetracyclines include Demeclocyline, Doxycycline, Vibramycin, Minocycline, Minocin, Oxytetracycline, Terracin, Tetracycline, and Sumycin, Other exemplary antibiotics include Salvarsan, Chloamphenicol, Chloromycetin, Clindamycin, Cleocin, Linomycin, Ethambutol, Fosfomycin, Fusidic Acid, Fucidin, Furazolidone, Isoniazid, Linezolid, Zyvox, Metronidazole, Flagyl, Mupirocin, Bactroban, Nitroiurantion, Macrodantin, Macrobid, Platensimycin, Pyrazinamide, Quinupristin:Dalfopristin (Syncerid), Rifampin (Rifampicin), and Tinidazole. An exemplary antibiotic also includes xylitol.

Anti-Inflammatory

The compositions and compounds described herein (e.g., soluble polyglucosamines and derivatized polyglucosamines) can be used in combination with (e.g., in series with, before, or after) one or more anti-inflammatory drugs, e.g., steroidal anti-inflammatory drugs and non-steroidal anti, inflammatory drugs (NSAIDs), to treat one or more diseases or conditions described herein. In some embodiments, the administrations of a combination of agents and therapeutics are spaced such that the activity (e.g., efficacy, effectiveness) of one or both agents is potentiated. In some embodiments, the administrations of a combination of agents and therapeutics are spaced sufficiently close together such that a synergistic effect is achieved.

Exemplary steroidal anti-inflammatory drugs include glucocorticoids (corticosteroids). e.g., Hydrocortisone (Cortisol), Cortisone acetate, Prednisone, Prednisolone, Methylprednisolone, Dexamethasone, Betamethasone, Triamcinolone, Beclometasone, Fludrocortisone acetate, Deoxycorticosterone acetate (DOC A), and Aldosterone, Exemplary non-steroidal anti-inflammatory drugs include Aspirin, Choline and magnesium salicylates, Choline salicylate, Celecoxib, Diclofenac potassium, Diclofenac sodium, Diclofenac sodium with Isoprostol, Diflunisal, Etodolac, Fenoprofen calcium, Flurbiprofen, Ibuprofen, Indomethacin, Ketoprofen, Magnesium salicylate, Meclofenamate sodium, Mefenamic acid, Meloxicam, Nabumetone, Naproxen, Naproxen sodium, Oxaprozin, Piroxicam, Rofecoxib, Salsalate, Sodium salicylate, Sulindac, Tolmetin sodium, and Valdecoxib, Exemplary non steroidal anti-inflammatory agents (e.g., peptides) include regulatory cytokines, such as interleukins. e.g., IL-1, IL-4, IL-6, IL-10, IL-11, and IL-13.

Mucolytic Agent (Expectorant)

The compositions and compounds described herein (e.g., soluble polyglucosamines and derivatized polyglucosamines) can be used in combination with (e.g., in series with, before, or after) one or more mucolytic agents, to treat one or more diseases and conditions described herein. A mucolytic agent or expectorant is an agent which dissolves thick mucus and is used to help relieve respiratory difficulties. It does so by hydrolyzing glycosaminoglycans, tending to break down/lower the viscosity of mucin-containing body secretions/components. The viscosity of mucous secretions in the lungs is dependent upon the concentrations of mucoprotein, the presence of disulfide bonds between these macromolecules and DNA.

An expectorant can reduce the thickness or viscosity of bronchial secretions and help bring up mucus and other material from the lungs, bronchi, and trachea. An example of as expectorant is guaifenesin which promotes drainage of mucus from the lungs by thinning the mucus and also lubricates the irritated respiratory tract. Other exemplary mucolytic agents or expectorants include Althea root. Antimony pentasulfide, Creosote, Guaiacolsulfonate, Guaifenesin, Ipecacuanha (Syrup of ipecac), Levoverbenone, Potassium iodide, Senega, TyloxapoL Acetylcysteine, Ambroxol, Bromhexine, Carbocisteine, Domiodol, Dornase alfa, Eprazinone, Erdosteine, Letosteine, Mesna, Neltenexine, Sobrerol, Stepronin, and Tiopronin.

Methods of Administration

The compounds and compositions described herein can be administered to a subject in a variety of ways. Exemplary methods of administration are described herein.

The compounds and compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. The methods and compositions of the described invention may be used in the form of drops or sprays (e.g., a nasal spray, aerosol spray, or pump spray) or other vehicles for inhalation or nasal administration (intranasal delivery). Aerosol spray preparations can be contained in a pressurized container with a suitable propellant such as a hydrocarbon propellant Pump spray dispensers can dispense a metered dose or a dose having a specific particle or droplet size. Any dispensing device can be arranged to dispense only a single dose, or a multiplicity of doses. More generally, compositions of the invention formulated for inhalation or intranasal administration, can also be provided as solutions, suspensions, or viscous compositions. In some embodiments, the compositions of the invention (e.g., compositions of compounds described herein), are provided as solution compositions. In some embodiments, the compositions of the described invention can be delivered by other instruments, e.g., including but not limited to, a nebulizer, an insufflators, an inhaler, or a puffer.

The compounds and compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compounds and compositions of this invention may also be administered rectally, for example in the form of suppositories or enema for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compounds and compositions of this invention is useful when the desired treatment involves areas or organs readily accessible by topical application. For application topically to the skin, the compounds and compositions should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the compounds and compositions can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compounds and compositions of this invention may also be topically applied to the lower intestinal tract by rectal suppository formulation or in a suitable enema formulation. Topically-transdermal patches are also included in this invention.

When the compounds and compositions described herein can include one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.02 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the compounds and compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Subject

The subject can be a human or an animal. Suitable animal subjects include: but are not limited to, pet, wild, zoo, laboratory, and farm animals. Suitable animal subjects include primates, mammals, rodents, and birds. Examples of said animals include, but not limited to, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, fowl, e.g., pheasant, quail (or other gamebirds), a waterfowl, ostriches, chickens, turkeys, ducks, and geese or free flying bird.

In some embodiments, the subject has a lung disease, e.g., a lung disease as described herein. In some embodiments, the subject has respiratory tract infections (e.g., airway infections, lung infections, pneumonia, and chronic sinusitis) or complications (e.g., infections or increased pulmonary mucosal viscosity) of cystic fibrosis, gastrointestinal infections (e.g. gastroenteritis).

In some embodiments, the subject has diseases or conditions characterized by the presence of one or more of the bacteria that cause resistant bacterial infection as described herein.

EXAMPLES

Unless otherwise indicated, PAAG as used in the Examples below is 18 to 30% functionalized, 20 to 150 kDa average molecular weight PAAG.

Example 1. PAAG Reduction of Biofilms Compared to Relevant Mucolytics

Protocol:

Three Methicillin-resistant *Staphylococcus aureas* (MRSA) clinical isolates were obtained from Providence Medical Center (Portland, Oregon) and had been obtained from respiratory tract/sputum (SA4, SA5, and SA6). *P. aeruginosa* strains SUS1116 and MR29 (clinical isolates from Jane Burns Lab Seattle Childrens Hospital, WA), and *Burkholderia cepacia* (ATCC 25416), were obtained from a −80 C freezer stock culture and propagated overnight in nutrient broth at 37° C. The optical density (OD) of each culture was measured at 600 nm, and each culture was normalized to 2 McFarland (0.451 OD), using tryptic soy broth (TSB). The cultures were diluted in TSB supplemented with 1% glucose to obtain a cell density of $2.0 \times 10^7$ cells/mL. Each culture was mixed well by inversion and passed on to a flat-bottomed 96-well plate by placing 200 µL into each well, corresponding to approximately $4.0 \times 10^6$ bacteria/well. The bacteria formed static biofilms at 37° C. for approximately 20 hours.

After incubation, the biofilms were washed twice allowing only adherent biofilm to remain on the plate. Each isolate was then treated for 1 hour in a 37° C. incubator with 200 µl of 600 µg/ml PAAG (22.4% functionalization, 36.9 kDa, 89.74 DDA, 1.63 PDI), 400 µg/ml PAAG, 200 µg/ml PAAG, 100 µg/ml PAAG, 50 µg/ml PAAG, 1 mg/ml Heparin, 7% NaCl, 3 µg/ml Dornase alfa, 300 mM mannitol, and water as a control. The plates were washed twice by submerging in a 2 L beaker filled with water, and left to air-dry under a laminar flow hood for approximately 1 hour. When dry, 50 µl of 99% ethanol was added to each well for 30 minutes to fix the biofilms. The ethanol was removed, and biofilms were washed once by submerging the plate in a 2 L beaker filled with water. Plates were left to dry under the hood for 30 minutes. When dry, 50 µl of 0.12% crystal violet was added to each well, and plates were incubated at room temperature for 1 hour. The dye was removed, and the biofilms were washed twice. Then, loot of 30% acetic acid was added to each well and incubated at room temperature for 1 hour. The OD of each well was measured at 595 nm in a multi well plate reader.

Results:

Consistently, concentrations of PAAG ranging from 400 to 600 µg/mL significantly reduced MRSA biofilms (FIGS. 1-3) within 1-hour treatment (p<0.002). Further, *P. aeruginosa* strain SUS116 showed a significant reduction (FIG. 1) at all the concentrations (50-600 µg/mL) tested (p<0.0001) and strain MR29 consistently showed a significant reduction (FIG. 4) between 600-100 µg/mL PAAG treatment after 1-hour (p<0.001). The *B. cepacia* strain also showed a significant reduction (FIG. 1) at all the concentrations of PAAG (600-50 µg/mL) tested (p<0.0001). None of the other relevant mucolytics showed a significant reduction in biofilms (FIGS. 1-4). Thus, these studies indicate that PAAG is a mucolytic that also acts to reduce bacterial biofilms of clinically relevant strains associated with lung disease and infections.

Example 2. PAAG and Polyols Synergistic Reduction q MRSA Biofilms

Protocol:

The clinical isolates (MRSA SA5, *P. aeruginosa* SUS116), and *B. cepacia* (ATCC 25416) were obtained from a −80 C freezer stock culture and propagated overnight in nutrient broth at 37° C. The OD of each culture was measured at 600 nm, and each culture was normalized to 2 McFarland (0.451 OD), using TSB. The cultures were diluted in TSB supplemented with 1% glucose to obtain a cell density of $2.0 \times 10^7$ cells/mL. Each culture was mixed by inversion and 200 µl, was placed on to a flat-bottomed 96-well, corresponding to approximately $4.0 \times 10^6$ bacteria/well. The bacteria formed static biofilms at 37° C. for approximately 20 hours.

After incubation, the biofilms were washed twice allowing only adherent biofilm to remain on the plate. Each isolate was then treated for 1 hour in a 37° C. incubator with 200 µl of 600 µg/ml PAAG (22.4% functionalization, 36.9 kDa, 89.74 DDA, 1.63 PDI), 4001 µg/ml PAAG, 2001 g/ml PAAG, 100 µg/ml PAAG, or 50 µg/ml PAAG alone, and in combination with 1%, 3%, or 5% sorbitol, and water as a control. The plates were washed, dried, then fixed prior to quantification via crystal violet stain retention where the OD 595 nm of each well was measured in a multi well plate reader.

Figure 5:
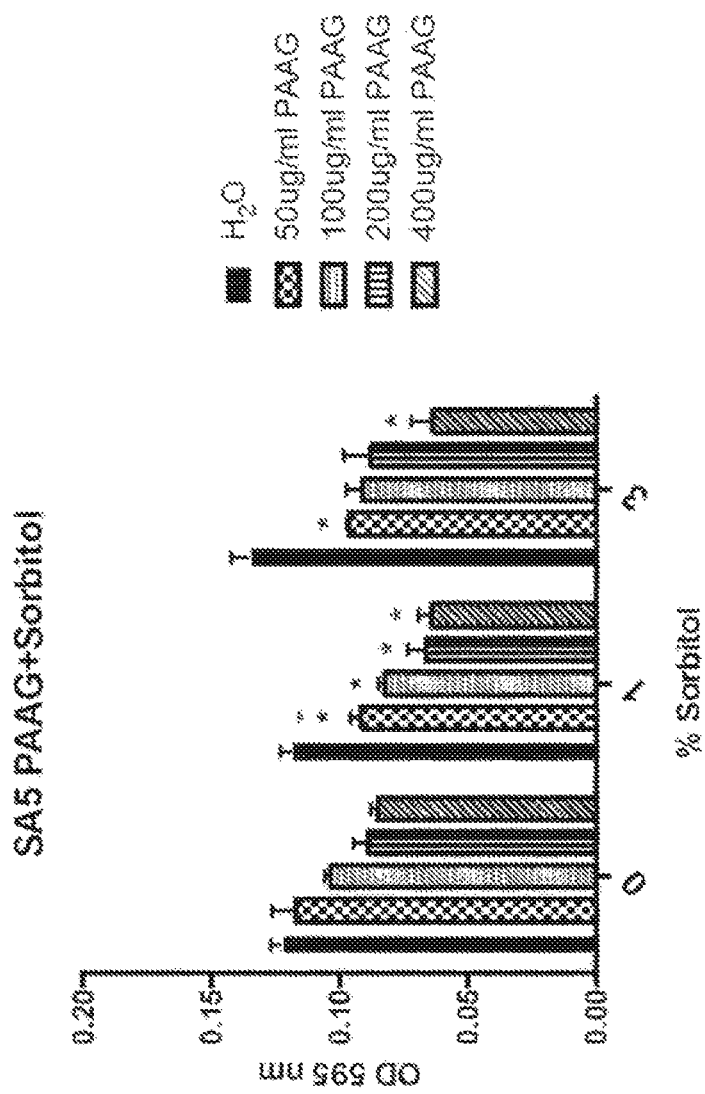
FIG. 5. Sorbitol potentiates biofilm removing activity of PAAG at 50-400 µg/mL final concentrations against MRSA (clinical strain SA5).
Figure 6:
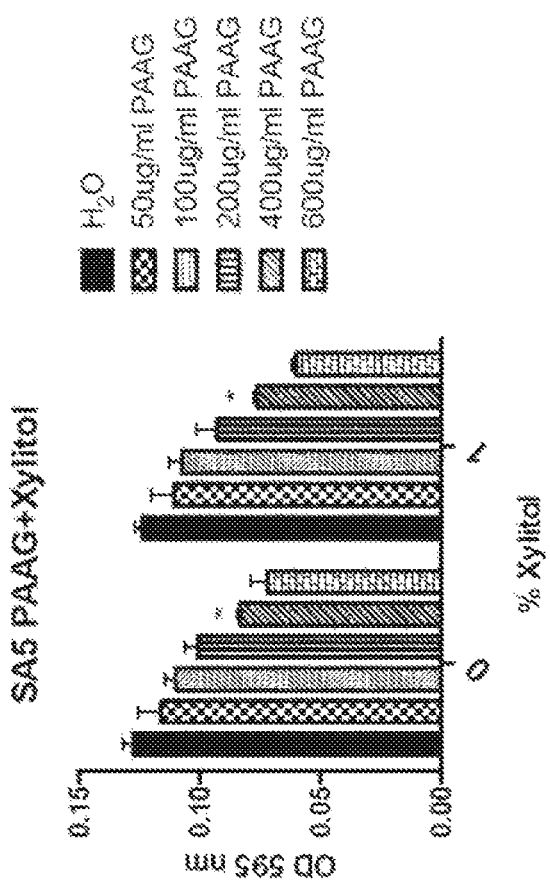
FIG. 6. Xylitol potentiates biofilm removing activity of PAAG at 50-600 µg/mL final concentrations against MRSA (clinical strain SA5).

Results:

The MRSA strain SA5 showed a significant increased biofilm removal in the presence of sorbitol (FIG. 5) and xylitol (FIG. 6). Specifically, 50 µg/mL of PAAG with either 1 or 3% sorbitol was significantly different than 50 µg/mL PAAG alone treated biofilms with p<0.01 and p<0.05, respectively. Also, 100, 200 or 400 µg/mL PAAG with 1% sorbitol removed significantly more biofilms than PAAG alone (p<0.05) and 400 µg/mL PAAG with 3% sorbitol showed a significant increase in biofilm reduction compared to 400 µg/mL PAAG alone (p<0.05). The addition of 1% xylitol to 400 µg/mL PAAG significantly reduced biofilms compared to PAAG alone (p<0.01). Thus, these studies indicate it may be possible to formulate PAAG with polyols to achieve greater reductions in biofilm biomass.

Example 3. PAAG Potentiates Antibiotics in the Reduction and Inhibition of MRSA and *P. aeruginosa* Biofilms Protocol:

Stationary biofilm assay was used to evaluate the ability of PAAG to potentiate antibiotics in the removal of pre-formed biofilms. The clinical isolates, MRSA SA5 and *P. aeruginosa* SUS116, were obtained from the −80 C freezer stock culture and propagated overnight in nutrient broth at 37° C. The OD of each culture was measured at 600 nm, and each culture was normalized to 2 McFarland (0.451 OD), using TSB. The cultures were diluted in TSB supplemented with 1% glucose to obtain a cell density of $2.0 \times 10^7$ cells/mL. Each culture was mixed by inversion and 200 µE was placed on to a flat-bottomed 96-well, corresponding to approximately $4.0 \times 10^6$ bacteria/well. The bacteria formed static biofilms at 37° C. for approximately 20 hours.

After incubation, the liquid culture in each well was removed, and then washed twice by adding 200 ul of water in each well and removed. This allowed only the adherent biofilms to remain on the plate. For each 96-well plate tested, a separate 96-well plate was used to mix PAAG (30.7% functionalization, 86.53 kDa, 87.92 DDA, 1.63 PDI) and each relevant antibiotic in a checkerboard assay, at twice the concentration to be tested. Then, 100 ul of water was added to each well of the pre-formed biofilms and 100 ul from each well of the mixed treatments was then dispensed onto the biofilm plate to half the concentration of each treatment to the desired value. For MRS A strain SA5, the PAAG concentrations tested were between 0-256 µg/ml and the vancomycin concentration tested was 1 µg/ml. For *P. aeruginosa* strain SUS116, the PAAG concentrations tested were between 0-256 µg/ml and the tobramycin concentrations tested was 1 µg/ml. After all treatments were in place, the biofilms were incubated in a static incubator at 37° C. for 1 hour. The plates were washed, dried, then fixed prior to quantification via crystal violet stain retention where the OD 595 nm of each well was measured in a multi well plate reader.

Figure 7:
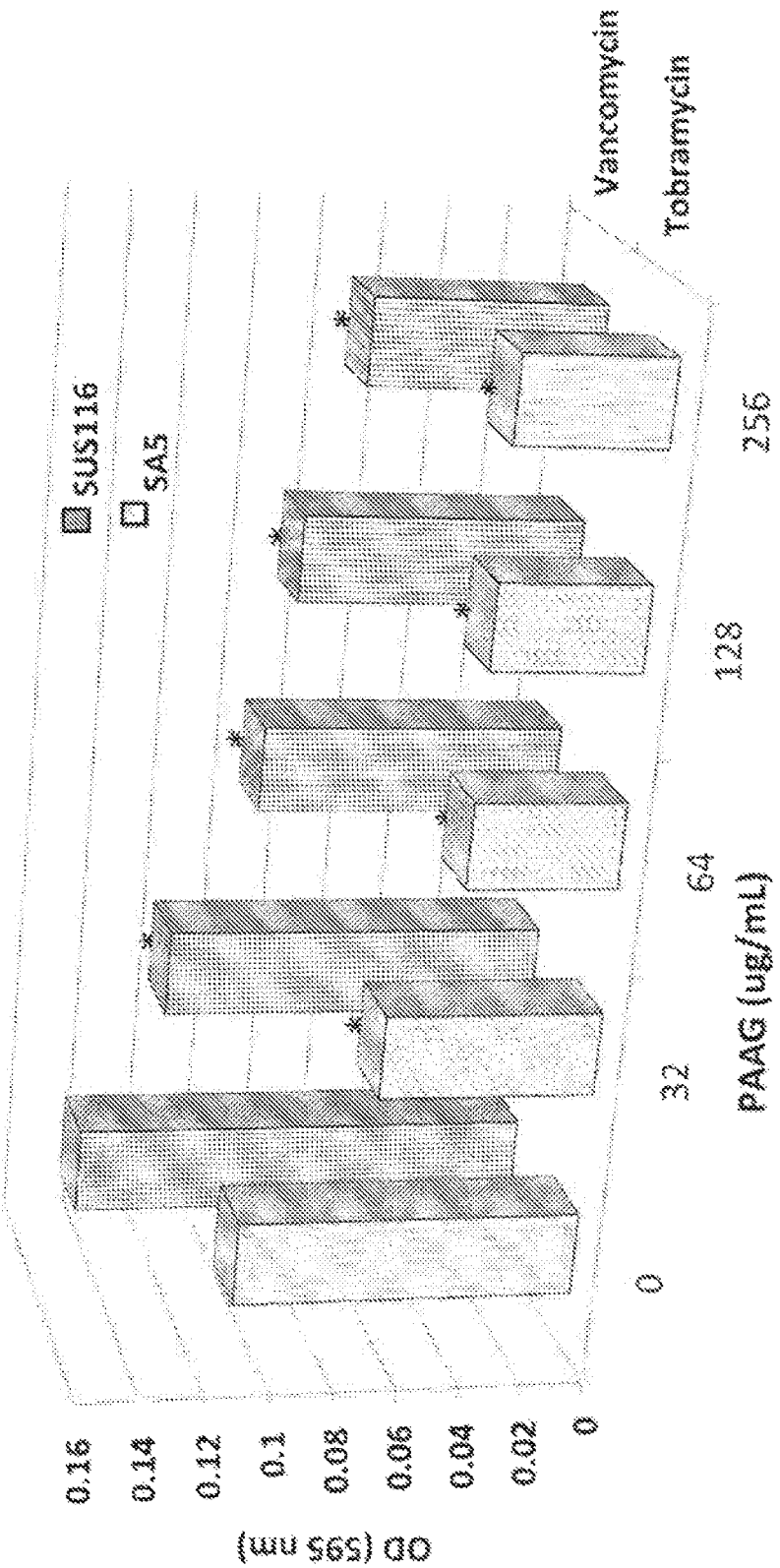
FIG. 7. Influence of tobramycin and vancomycin antibiotics on the biofilm removing activity of PAAG at 32-256 µg/mL final concentrations against P. aeruginosa (clinical strain SUS116), and MRSA (clinical strain SA5), respectively.

Results:

FIG. 7 shows a significant dose dependent antibiotic potentiation was observed when PAAG and tobramycin treated *P. aeruginosa* biofilms for 1 hour (p<0.05). Also, a significant dose dependent antibiotic potentiation was observed when PAAG and vancomycin were co-administered to MRSA biofilms for 1 hour (p<0.01). This study demonstrates that PAAG does not interfere with common antibiotics used to treat bacteria associated with respiratory infections and may potentiate the antibacterial activity of antibiotics.

Protocol:

MBEC™ checkerboard assay determined the synergistic activity of tobramycin and PAAG against *P. aeruginosa* (PA01) peg biofilms. Synergistic relationships between PAAG and tobramycin against *P. aeruginosa* biofilms were examined in vitro using the MBEC™ for High-throughput Screening (Innovotech, Edmonton, AB Canada). The biofilms were grown on a peg lid placed in trough with Mueller-Hinton (MH) broth media supplemented with 0.5% glucose for 24 hours. Serial two-fold dilutions of PAAG and tobramycin and controls were made in duplicate, in a 96-well format. Each biofilm plate was incubated in the 64 and 128 µg/ml PAAG (30.7%/o functionalization, 86.53 kDa, 87.92 DDA, 1.63 PDI) treatments for 3 hours. The biofilms were rinsed, and the pegs removed and placed into microfuge tubes in 200 µl of water. The tubes were sonicated and aliquots of recovered biofilms were diluted and plated onto nutrient agar to quantify growth. Synergy was determined as at least a 2-log reduction over the most active agent.

Figure 8:
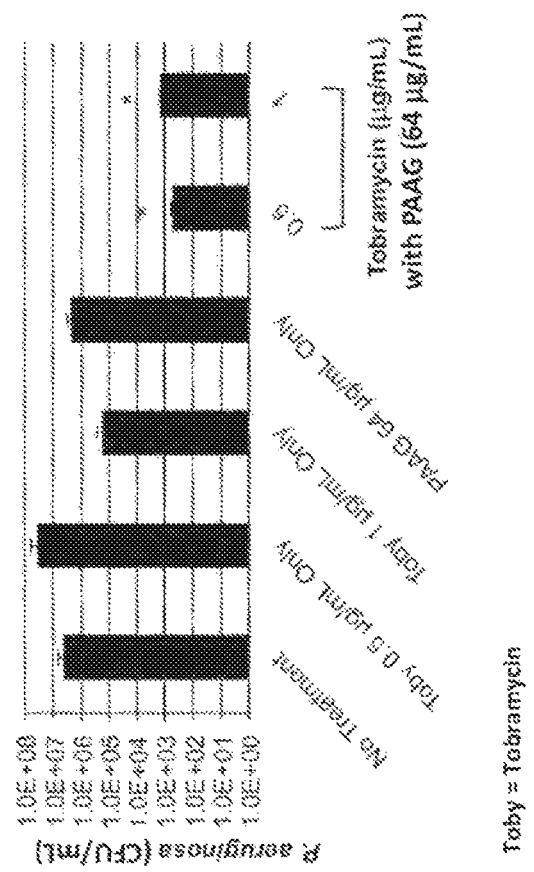
FIG. 8. Reduction in P. aeruginosa biofilms using 64 µg/mL PAAG and 0.5-1 µg/mL tobramycin is synergistic.
Figure 9:
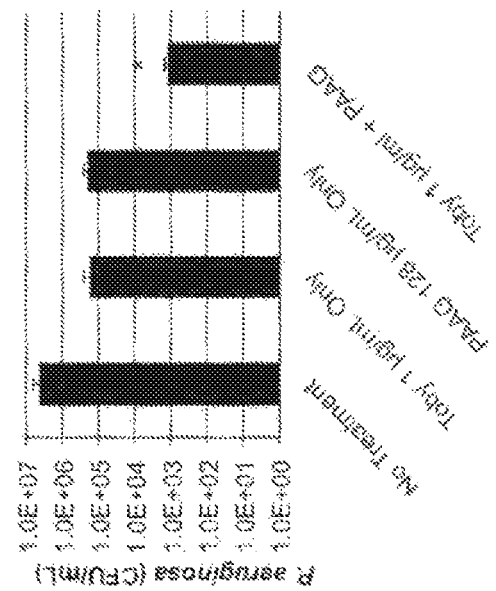
FIG. 9. Reduction in P. aeruginosa biofilms using 128 µg/mL PAAG and 1 µg/mL tobramycin is synergistic.

Results:

FIG. 8 shows 64 µg/mL PAAG is synergistic with 0.5 µg/mL and 1 µg/mL tobramycin and against *P. aeruginosa* biofilms by demonstrating a 2-log reduction beyond the most active agent. FIG. 9 shows PAAG 128 µg/mL is synergistic with tobramycin 1 µg/mL against *P. aeruginosa* biofilms (2-log reduction). The asterisk (*) indicates a 2-log reduction beyond most active agent.

Protocol:

The Minimal Biofilm Inhibitory Concentration (MBIC) assay was used to evaluate the ability of PAAG to potentiate antibiotics ability to inhibit biofilm formation. Each isolate was taken from the −80° C. freezer stock and grown for approximately 20 hours in LB Broth at 37° C. shaking water bath. The OD of each culture was measured at 600 nm, and each culture was normalized to 0.08 OD in Mueller-Hinton (MH) Broth supplemented with 0.4% glucose, (2× concentration to accommodate addition of treatments). The antibiotics and PAAG (22.4% functionalization, 36.9 kDa, 89.74 DDA, 1.63 PDI) were prepared similar to a checkerboard assay (2× concentration to accommodate addition of culture) in MH broth, in a sterile flat-bottomed 96-well plate. For MRSA strain SA5, the PAAG concentrations tested were 0-128 ug/ml. The vancomycin concentrations tested were 0-4 ug/ml. For *P. aeruginosa* strain SUS116, the PAAG concentrations tested were 0-128 ug/ml. The tobramycin concentrations tested were 0-4 ug/ml. Plates were incubated in a 37° C. incubator.

After incubation, the liquid culture in each well was removed, and then washed twice by adding 200 ul of PBS in each well and removed. This allowed only the adherent biofilms to remain on the plate. The plates were washed, dried, then fixed prior to quantification via crystal violet stain retention where the OD 595 nm of each well was measured in a multi well plate reader.

The fractional inhibitory concentration (FIC) was calculated as; FIC calculation:

$$FIC = \frac{MIC\ a\ \text{with}\ b}{MIC\ a\ \text{alone}} + \frac{MIC\ b\ \text{with}\ a}{MIC\ b\ \text{alone}}$$

and the FIC relationship was defined as; Synergy: FIC≤0.5; Additive: 0.5<FIC≤1.0; or Indifferent: FIC>1.0.

Figure 10:
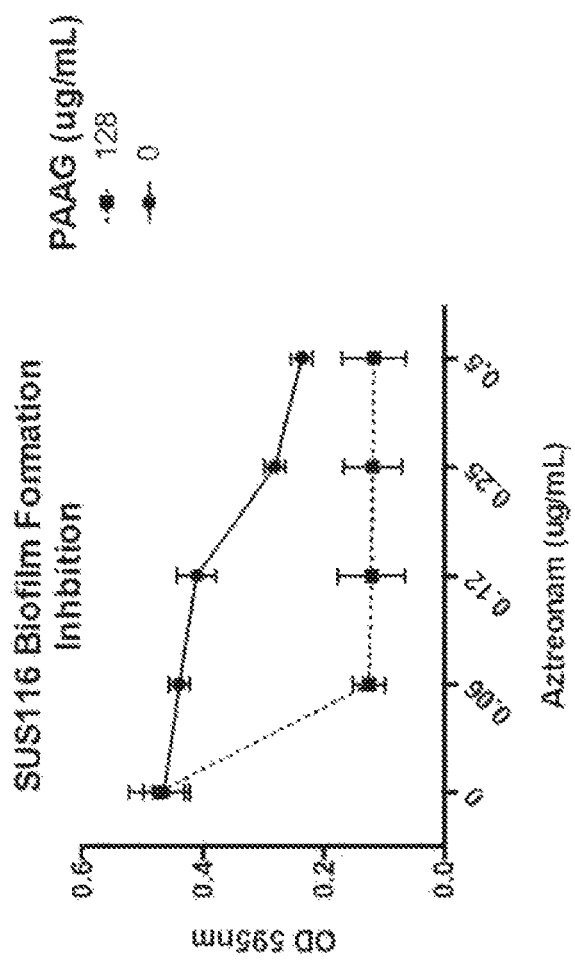
FIG. 10. PAAG P. aeruginosa (clinical strain SUS116) biofilm growth inhibition at 128 µg/mL final concentration is potentiated by aztreonam (0-0.5 µg/mL).
Figure 11:
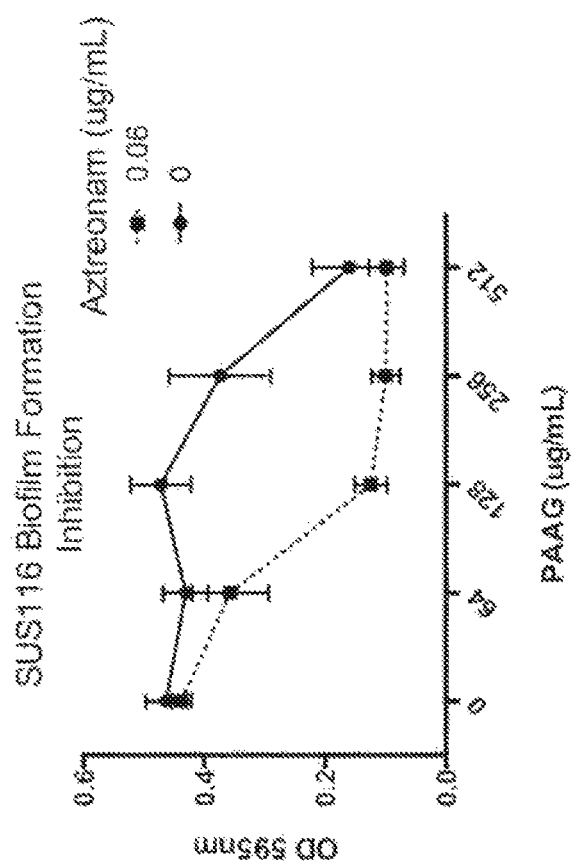
FIG. 11. Aztreonam P. aeruginosa (clinical strain SUS116) biofilm growth inhibition at 0.06 µg/mL is potentiated by 64-512 g/mL PAAG at final concentrations.
Figure 12:
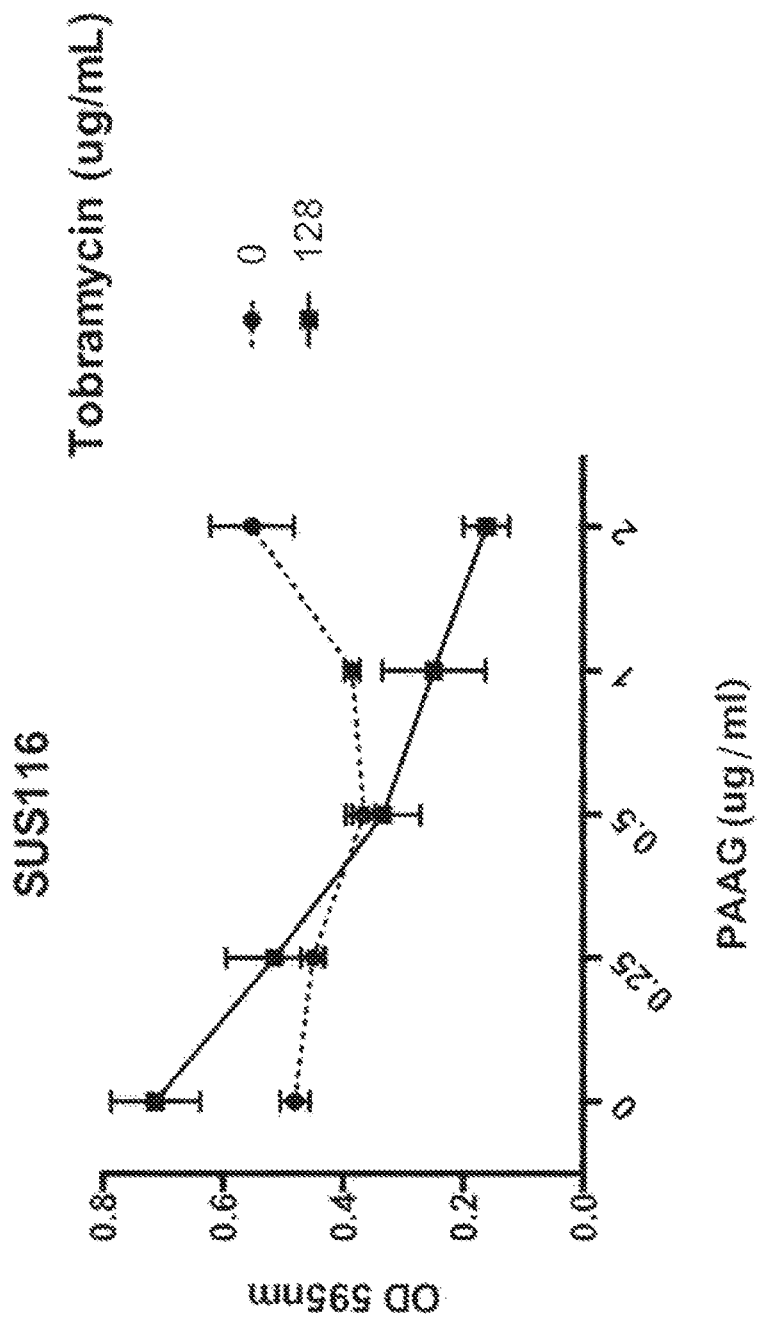
FIG. 12. PAAG P. aeruginosa (clinical strain SUS116) biofilm growth inhibition at 128 µg/mL final concentration is potentiated by tobramycin (0.25-2 µg/mL).
Figure 13:
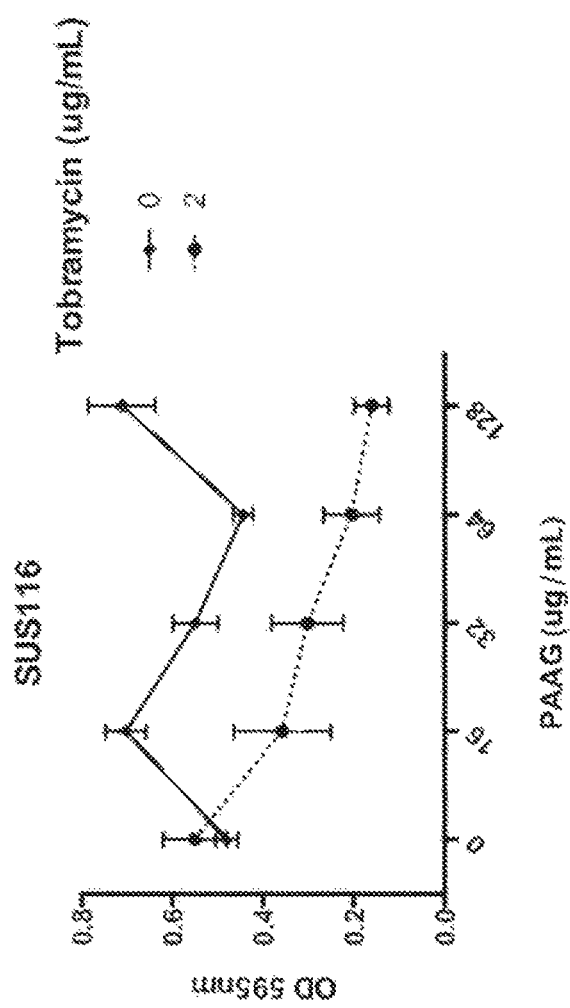
FIG. 13 Tobramycin P. aeruginosa (clinical strain SUS116) biofilm growth inhibition at 2 µg/mL is potentiated by 16-128 µg/mL PAAG at final concentrations.
Figure 14:
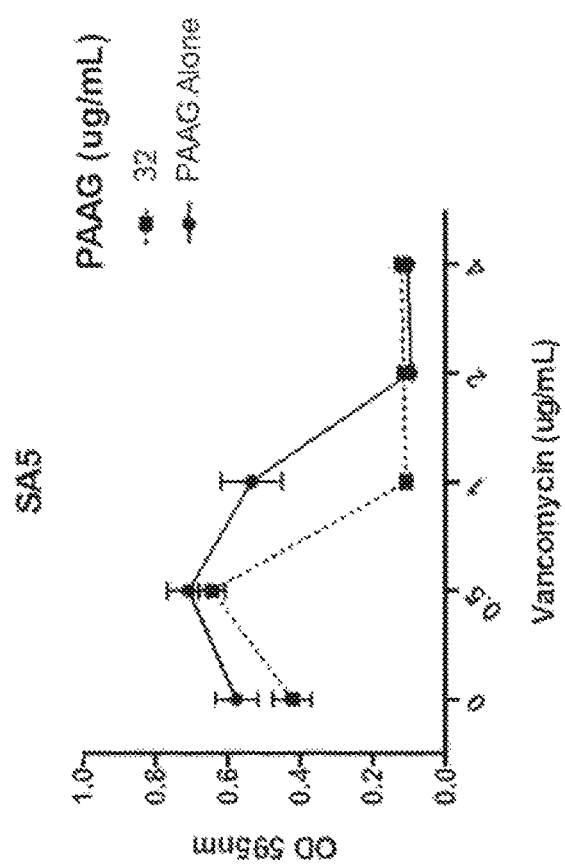
FIG. 14. PAAG MRSA (clinical strain SA5) biofilm growth inhibition at 32 µg/mL final concentration is potentiated by vancomycin (0.5-4 µg/mL).
Figure 15:
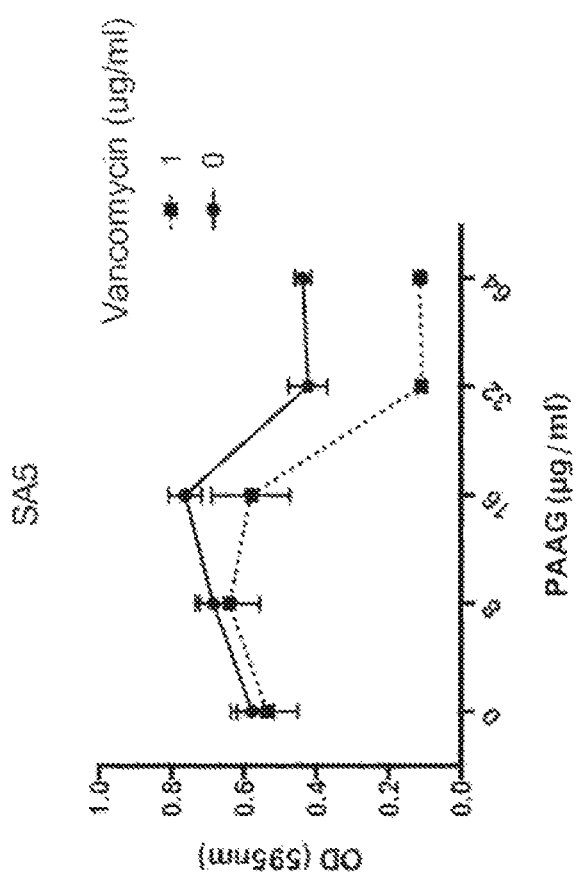
FIG. 15. Vancomycin MRSA (clinical strain SA5) biofilm growth inhibition at 1 µg/mL is potentiated by 8-64 µg/mL PAAG at final concentrations.

Results:

The MBIC assays showed PAAG and aztreonam were synergistic against *P. aeruginosa* (FIGS. 10-11, Table 1) as determined by the calculated fractional inhibitory concentration (FIC). An additive effect was observed between PAAG and tobramycin against *P. aeruginosa* (FIGS. 12-13, Table 2) and between PAAG and vancomycin against MRSA (FIGS. 14-15, Table 3).

TABLE 1

The FIC calculation of PAAG and aztreonam shows synergy against *P. aeruginosa* strain SUS116.

| | MBIC (µg/mL) | | | | | |
|---|---|---|---|---|---|---|
| *P. aeruginosa* Strain | PAAG | Tobramycin | PAAG (with Aztreonam) | Aztreonam (with PAAG) | FIC* | Relationship |
| SUS 116 | 512 | 2 | 12S | 0.06 | 0.57 | Synergistic |

*Fractional Inhibitory Concentration

TABLE 2

The FIC calculation of PAAG and tobramycin shows synergy against *P. aeruginosa* strain SUS116.

| | MBIC (Mg/mL) | | | | | |
|---|---|---|---|---|---|---|
| *P. aeruginosa* Strain | PAAG | Tobramycin | PAAG (with Toby) | Tobramycin (with PAAG) | FIC* | Relationship |
| SUS 116 | 512 | 6.25 | 12S | 2 | 0.57 | Additive |

*Fractional Inhibitory Concentration

TABLE 3

The FIC calculation of PAAG and vancomycin demonstrates synergy against MRSA strain SA5.

| | MBIC (Mg/mL) | | | | | |
|---|---|---|---|---|---|---|
| MRSA Strain | PAAG | Vancomycin | PAAG (with Vancomycin) | Vancomycin (with PAAG) | FIG* | Relationship |
| SA5 | 126 | 2 | 32 | 1 | 0.75 | Additive |

*Fractional Inhibitory Concentration

Example 4. PAAG and Antibiotics Synergistic Reduction of MRSA and *P. aeruginosa*, and *B. cepacia* Planktonic Bacteria Protocol:

Checkerboard and time kill bactericidal studies of mupirocin, methicillin-resistant *Staphylococcus aureus* strains 2-4C and 2-9A were completed as part of the synergy studies to evaluate potentiation of mupirocin (oxacillin) by PAAG (25% functionalized, 43 kDa). Synergistic relationships between PAAG and oxacillin were examined in vitro using the broth microdilution checkerboard assay in 96-well microtiter plates. Serial two-fold dilutions of PAAG and oxacillin were placed in each well with approximately $1 \times 10^5$ CFU/ml of *S. aureus*. Each plate was incubated 20 hours. The MIC was determined as the lowest concentration where no visible bacterial growth was observed. Concentration tested were $\frac{1}{32} \times$MIC to 4×MIC (0.5-64 µg/ml). Controls for bacterial growth and sterility were included. The FIC for each strain was calculated. The FIC is an interaction coefficient indicating whether the combined inhibitory/bacteristatic effect of drugs is synergistic (FIC of 0.5 or less), additive (FIC between 1 and 4), or antagonistic (FIC>4). The FIC is =A+B, where: A=(MIC of X with Y)/(MIC of drug X alone) and B=(MIC of Y with X)/(MIC of drug Y alone). The time-kill assay (vCFU) was performed using the microdilution technique. Approximately $1 \times 10^5$ CFU/ml of each bacteria tested was tested against mupriocin alone and in combination. Concentrations of PAAG tested were ½-⅛× MIC. The vCFU was determined after 24 hours treatment using the microtiter technique (8). Synergy was defined as a greater than 2-log reduction of the initial inoculum vCFU after 24-hours compared to the most active agent of the two agents tested in combination.

Results:

In this study, Mupirocin, Methicillin Resistant *Staphylococcus aureus* strains were tested against combinations of PAAG and oxacillin or mupirocin. The results of both studies showed synergy at multiple combinations of PAAG and antibiotic concentrations. Sensitization was observed with the mupirocin-resistant MRSA (Table 4). All strains were resistant to oxacillin in that the MIC >4 µg/ml oxacillin. Sensitization of these strains to oxacillin was demonstrated in that the addition of PAAG at 2 µg/ml (SA05), 8 µg/mil (MW-2, 2-1A, 2-9A), or 16 µg/ml (2-4C) was able to reduce the MIC of oxacillin to the susceptible (MIC>2 µg/ml) range (See bolded column OXA with PAAG Table 4). Mupirocin and PAAG were shown to have a synergistic relationship when used in combination against mupirocin-resistant MRSA strains 2-4C and 2-9A. Table 5 shows that when mupirocin (8 µg/ml) and PAAG (8 µg/ml) were used against mupirocin-resistant MRSA strain 2-4C, a 3.5 log reduction in the CFU was observed beyond that of the most active agent (PAAG). Table 5 also shows that when mupirocin (4 µg/ml) and PAAG (2 µg/ml) were used against mupirocin-resistant MRSA strain 2-9A, a 2.3 log reduction in the CFU was observed beyond that of the most active agent (PAAG).

TABLE 4

MIC and FIC values for the in vitro combination of PAAG and oxacillin against MRSA. Bold values denote sensitization as the resistance breakpoint for oxacillin is 2 μg/ml

| | MIC (μg/ml) | | | | | |
|---|---|---|---|---|---|---|
| Strain | PAAG | OXA | PAAG with OXA | OXA with PAAG | FIC* | Results |
| MW-2 | 32 | 4 | 8 | 1 | 0 5 | Synergistic |
| SAO5 | 32 | 4 | 2 | 1 | 0.3 | Synergistic |
| 2-1A | 32 | S | 8 | 1 | 0.5 | Synergistic |
| 2-4C | 64 | 16 | 16 | 2 | 0.4 | Synergistic |
| 2-9A | 64 | 8 | 8 | 0.5 | 0.2 | Synergistic |

*FIC was calculated as A + B, where: A = (MIC of X with Y)/(MIC of drag X alone) and B = (MIC of Y with X)/(MIC of drag Y alone). Values of 0.5 and below aie synergistic.

TABLE 5

Reduction of mupirocin-resistant MRSA strains 2-4C and 2-9A by PAAG and mupirocin alone and in combination after 24-hours. Synergy was defined as a greater than 2-log reduction of the initial inoculum vCFU beyond the most active agent. Bold values denote sensitization as the resistance breakpoint for mupirosin is 8 μg/ml.

| | Log10 reduction (CFU/ml) | | | |
|---|---|---|---|---|
| Strain | Mup (8 fig/ml) | PAAG (8 μg/ml) | Mup with PAAG | Relationship |
| 2-4C | 0 | 2.3 | 5.8 | Synergistic (3.5 reduction beyond PAAG |

TABLE 5-continued

Reduction of mupirocin-resistant MRSA strains 2-4C and 2-9A by PAAG and mupirocin alone and in combination after 24-hours. Synergy was defined as a greater than 2-log reduction of the initial inoculum vCFU beyond the most active agent. Bold values denote sensitization as the resistance breakpoint for mupirosin is 8 μg/ml.

| | Mup (4 μg/ml) | PAAG ˆg/ml) | Mup with PAAG | |
|---|---|---|---|---|
| 2-9A | 0 | 3.1 | 5.8 | Synergistic (2.3 reduction beyond PAAG |

Protocol:

Two independent checkerboard assays screened 64 unique combinations of antimicrobial concentrations in duplicate. For each study, approximately 1×10$^5$ bacteria/mL were treated with serial two-fold dilutions of PAAG (30.7% functionalization, 86.53 kDa, 87.92 DDA, 1.63 PDI) between 0-32 μg/InL and/or tobramycin between 0-4 μg/mL.

Bacteria were incubated at 37° C. for 20 hours. The MIC was determined as the lowest concentration with no visible bacterial growth observed.

Results:

Various *P. aeruginosa* clinical isolates were tested to determine the ability of PAAG to consistently exhibit antibiotic potentiation over a number of clinically relevant isolates. Table 6 shows that PAAG and tobramycin exhibit synergy in inhibiting growth of all tested strains, except MR29, against which PAAG and tobramycin have an additive effect. This study demonstrates that PAAG does not interfere with a common antibiotic used to treat bacteria associated with respiratory infections, and may potentiate antibiotics to treat clinically relevant strains of *P. aeruginosa* (Table 6).

TABLE 6

MIC and FIC values for the in vitro combination of PAAG and tobramycin against various clinical isolates of *P. aeruginosa*.

| | MIC (μg/mL) | | | | | |
|---|---|---|---|---|---|---|
| *P. aeruginosa* Strain | PAAG | Tobramycin | PAAG (with Toby) | Tobramycin (with PAAG) | FIC* | Relationship |
| SUS 116 | 125 | 1.25 | 4 | 0.13 | 0.1 | Synergistic |
| PA01 | 500 | 0.31 | 0.03 | 0.13 | 0.4 | Synergistic |
| AMT-32-4 | 62 | 0.31 | 0.25 | 0 13 | 0.4 | Synergistic |
| MR 51 | 1000 | 0.31 | 0.25 | 0.13 | 0.4 | Synergistic |
| MR29 | 1000 | 0.31 | 0.25 | 0.25 | 0.8 | Additive |

*Fractional Inhibitory Concentration

Protocol:

A checkerboard assay was used to screen 64 unique combinations of antimicrobial concentrations in triplicate. For each study, approximately 1×10$^6$ cells/mL were treated with PAAG (27% functionalization, 32 kDa; 31% functionalization, 54 kDa; and 25% functionalization, 40 kDa) between 0-64 μg/mL and/or tobramycin between 0-4 μg/mL. Bacteria were incubated at 37° C. for 20 hours. The fluorescent pigment pyocyanin produced by *P. aeruginosa* strain PA01 can be correlated with bacterial growth. The MIC values obtained with this protocol (fluorescence was measured 485 nm excitation, 535 nm emission) are the same as those obtained using optical density.

Results:

Three independent checkerboard assays were completed in triplicate using different lots of PAAG (27% functionalized, 32 kDa; 31% functionalized, 54 kDa; and 25% functionalization, 40 kDa) and tobramycin. The MIC of tobramycin is reduced 8 to 32-fold upon the addition of 4 μg/ml of PAAG (Table 7). All of the PAAG tested in Table 7 were shown to exhibit synergistic relationships with tobramycin as defined by the FIC (described above) because the value is less than 0.5. These analyses determined that co-administration of tobramycin and PAAG is synergistic against *P. aeruginosa* strain PA01. Specifically, PAAG lowers the MIC of tobramycin and works synergistically to eliminate *P. aeruginosa*. Mechanistically, PAAG might provide better drug access to the bacteria via disruption of the cell membrane or support enhanced interaction of antibiotics with the phosphoglycans on the cell surface. It is also suggests that the ability to potentiate antibacterial activity exists over a wide range of PAAG molecules with different % functionalizations and molecular weights.

TABLE 7

MIC and FIC values for the in vitro combination of various PAAG's and tobramycin against *P. aeruginosa* strain PA01.

| *P. aeruginosa* Strain PAQ1 | MIC (μg/mL) | | | | FIC* | Relationship |
|---|---|---|---|---|---|---|
| | PAAG | Tobramycin | PAAG (with Tobramycin) | Tobramycin (with PAAG) | | |
| PAAG[1] | 16 | 1 | 4 | 0.031 | <0.28 | Synergistic |
| PAAG[2] | 32 | 0.5 | 4 | 0.031 | <0.27 | Synergistic |
| PAAG[3] | 32 | 0.5 | 4 | 0.063 | <0.30 | Synergistic |

*Fractional Inhibitory Concentration
[1]27%, 32 kDa; [2]31%, 54 kDa; [3]25%, 40 kDa Example 6: PAAG Biofilm Antibacterial Activity Protocol:

Initial studies used the MBEC™ system to determine optimized PAAG (30.7% functionalization, 86.53 kDa, 87.92 DDA, 1.63 PDI) treatment time, administration, and dose for biofilm disruption of methicillin resistant *Staphylococcus aureus* (MRSA). Treatments showed the difference of multiple short-term rinses to 1-hour treatment against 24-hour MRSA biofilms.

Figure 16:
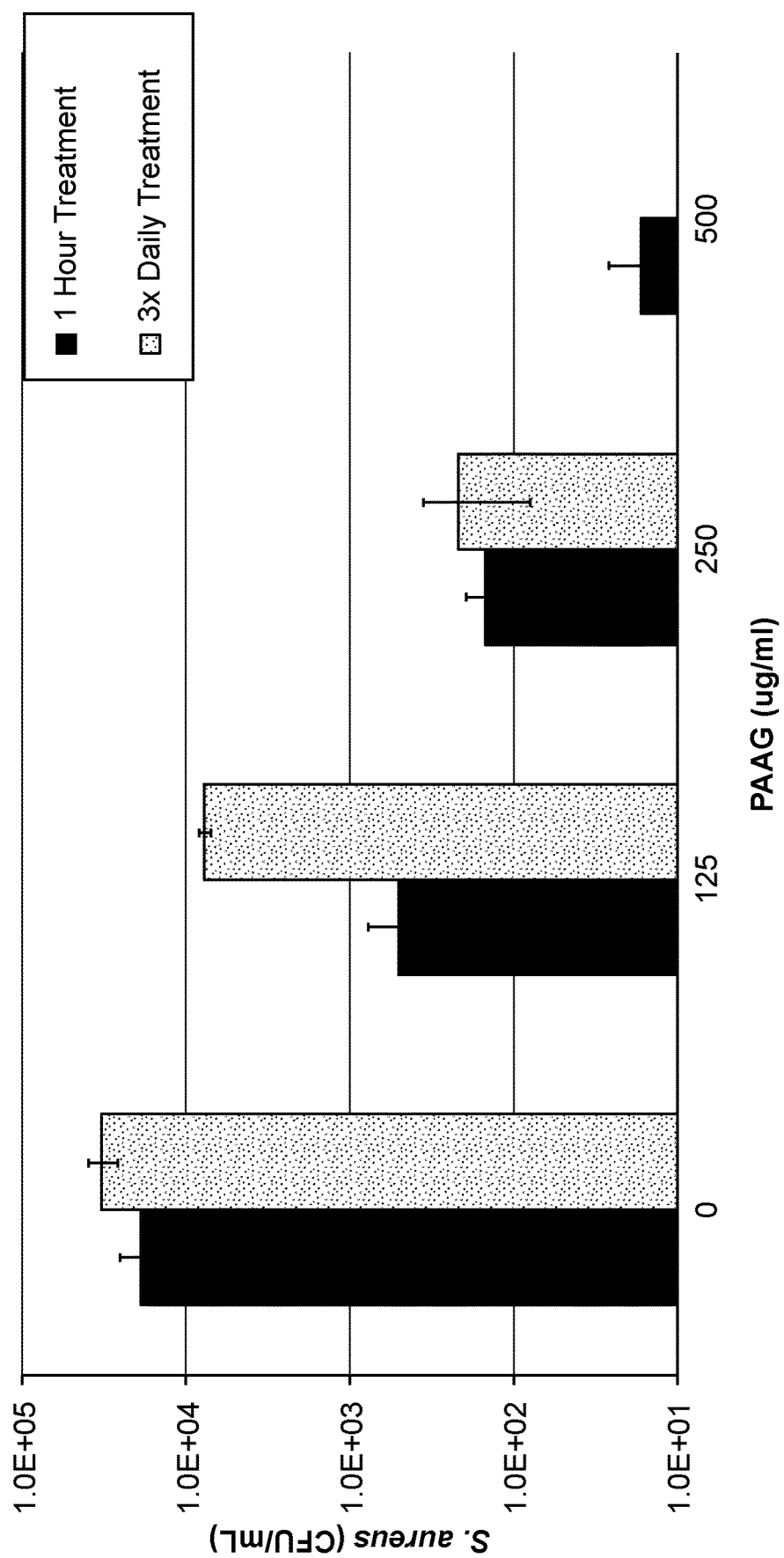
FIG. 16. Reduction in S. aureus biofilms using 125-500 µg/mL PAAG final concentrations varying in treatment length and daily treatment schedules.

Results:

PAAG was able to significantly reduce the viable bacteria associated with the biofilm. When PAAG was used to treat *S. aureus* a 2-minute rinse, three times a day was shown to be better or as effective as a single one-hour treatment with PAAG at 250 or 500 μg/mL (FIG. 16). These comparative studies demonstrate that a brief treatment, three times daily, was effective at reducing MRSA biofilms and may be a feasible dosing schedule for use in patients.

Protocol:

The biofilms were grown according to MBEC™ on a peg lid for 48 hours. The pegs were rinsed and placed into a 96-well plate with serial dilutions of the PAAG (25% functionalization, 43 kDa) or controls and exposed to PAAG for various times at room temperature. The biofilms were rinsed, and the pegs removed and placed into microfuge tubes in 200 μl of water. The tubes were sonicated and aliquots of recovered biofilms were diluted and plated onto nutrient agar to quantify growth.

Results:

PAAG was able to significantly reduce the viable bacteria associated with the biofilm. When PAAG was used to treat *P. aeruginosa* clinical isolates and *B. cepacia* for 6 hours with PAAG between 100-500 μg/mL (Table 8). These comparative studies demonstrate that PAAG was effective at reducing biofilms of clinical isolates associated with lung infections.

TABLE 8

The percent (%) biofilm reduction by PAAG after 6-hour treatment of various clinically relevant strains.

| Strain | PAAG (μg/mL) | | |
|---|---|---|---|
| | 100 | 200 | 400 (500") |
| *P. aeruginosa* PA01 | 86% | 9?% | 99% |
| *P. aeruginosa* MR 29 | 100% | 97% | 97% |

TABLE 8-continued

The percent (%) biofilm reduction by PAAG after 6-hour treatment of various clinically relevant strains.

| Strain | PAAG (μg/mL) | | |
|---|---|---|---|
| | 100 | 200 | 400 (500") |
| *P. aeruginosa* SUS116 | 92% | 91% | 100% |
| *S. cepacia* ATCC 25416 | 99% | 100% | 99%* |

*B. cepacia* was tested at 500 μg/mL, instead of 400 μg/mL

Example 7: PAAG Reduces Viscosity

Protocol:

Alginate models for biofilms were used to test if specific components of the biofilm were being affected (i.e. alginate). Homogeneous 1% sodium alginate solutions (35 mL each) were prepared in water. Viscosity was immediately measured on a Brookfield digital viscometer (Model DV-E) using spindle 62 at speed 30 rpm, after adding either 100 μg/mL PAAG (25% functionalization, 18 kDa, DDA 88, PDI 1.47), in 2 mL or an equivalent amount of water (control). Viscosity was also measured immediately, 1 hour following treatment.

Figure 17:
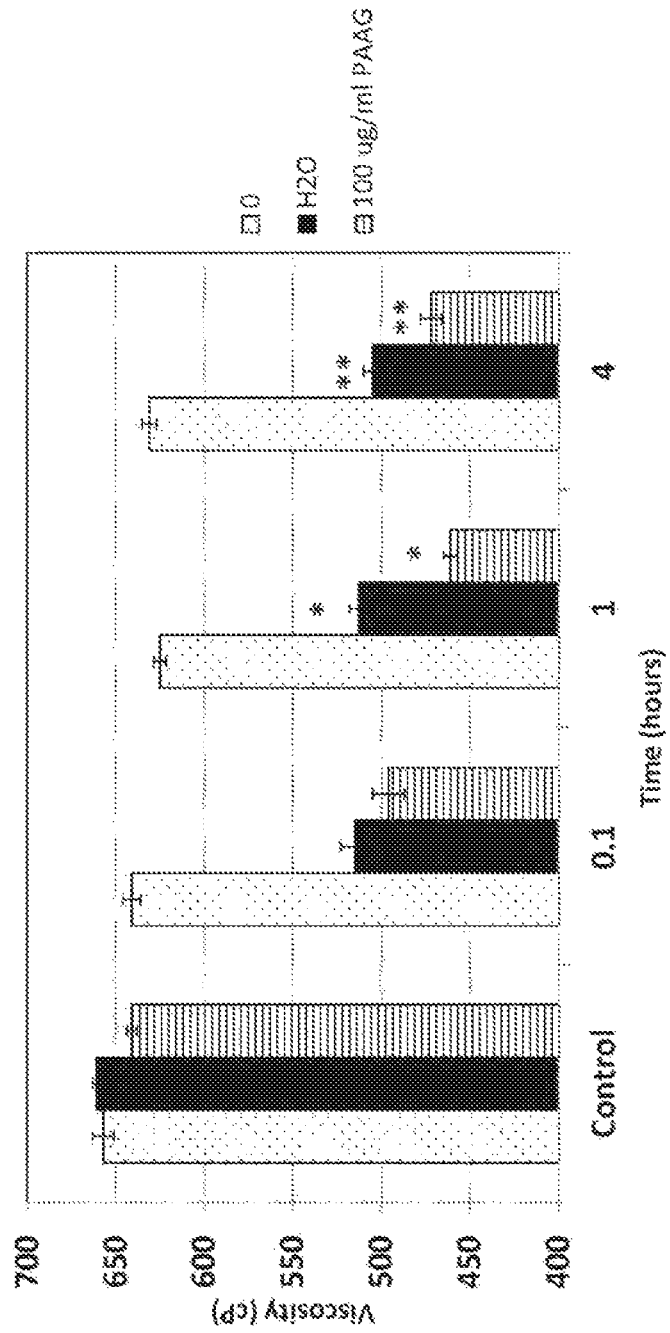
FIG. 17. PAAG at 100 µg/mL final concentration reduces viscosity of 1% alginate.

Results:

In the alginate model, PAAG was shown to reduce the viscosity of 1% alginate solution following treatment with 100 μg/ml compared to water. After 1 and 4 hours, PAAG had a significant (p=0.01) reduction in the viscosity of the sodium alginate solution (FIG. 17).

Protocol:

Fresh sputum ex vive from CF subjects hospitalized for pulmonary exacerbation was homogenized, divided into 200 μL aliquots, then treated with 100 μg/mL PAAG (70 kDa, 28% functionalized, 1.6 PDI) in a 37° C. water bath for 20 hrs or PBS control then evaluating by traditional viscometry across a range of strain forces. Sputum was then transferred to cone and plate rheometer for measurement of viscoelastic properties. Shear-dependent viscosity was measured with a TA Instruments Discovery Series HRII Rheometer. After a 10-minute conditioning period, a flow ramp procedure began with initial stress $1.0e^{-3}$ to 10 Pa for 600 seconds in log mode. Five points were observed per decade and over-sampling of controlled stress was checked. An oscillation frequency procedure immediately followed with 5% strain, a logarithmic sweep from 0.05 to 20 Hz frequency, 10 points observed per decade, continuous direct controlled strain, and 3 second conditioning time with 3 second sampling time data acquisition parameters. The elasticity values were recorded from the oscillation frequency procedure. A flow sweep procedure then made a logarithmic sweep from 0.02 to 1000 l/s shear rate, 5 points per decade were recorded, followed by a 5 second equilibration time and a 1 to second averaging time. The motor mode for controlled rate was set to automatic. The viscosity values were recorded from the flow sweep procedure.

Figure 18:
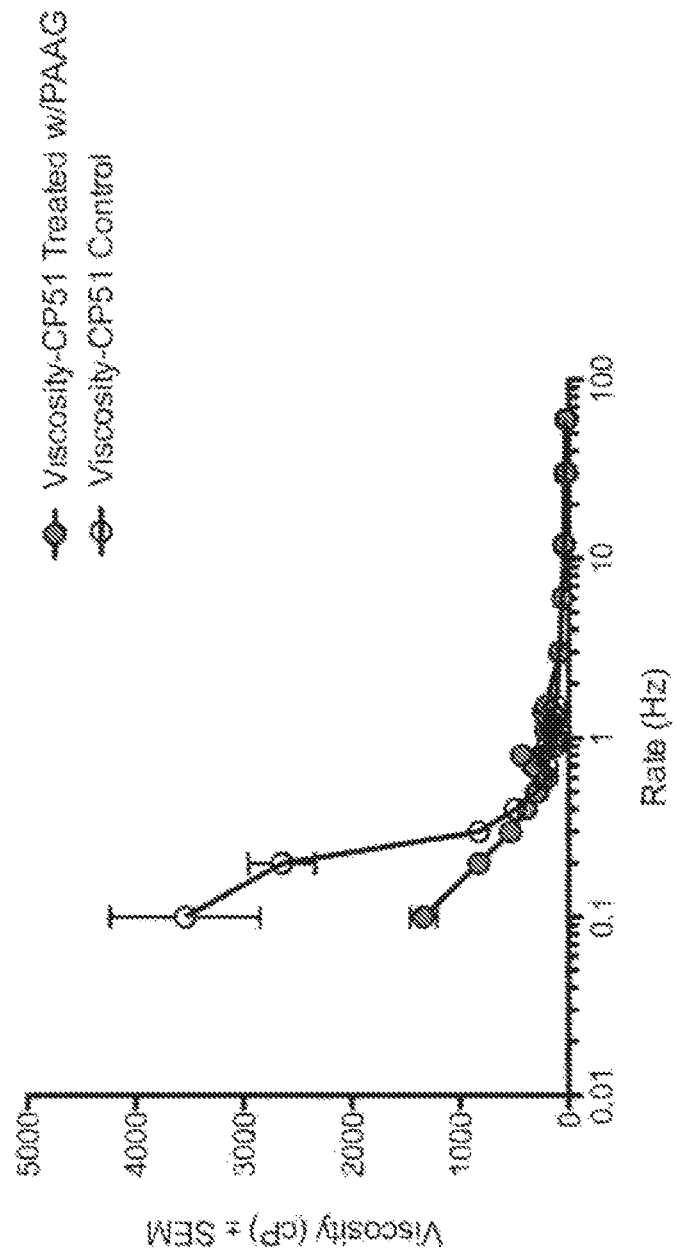
FIG. 18. Reduction of CF sputum viscosity by PAAG at 100 µg/mL final volume.
Figure 19:
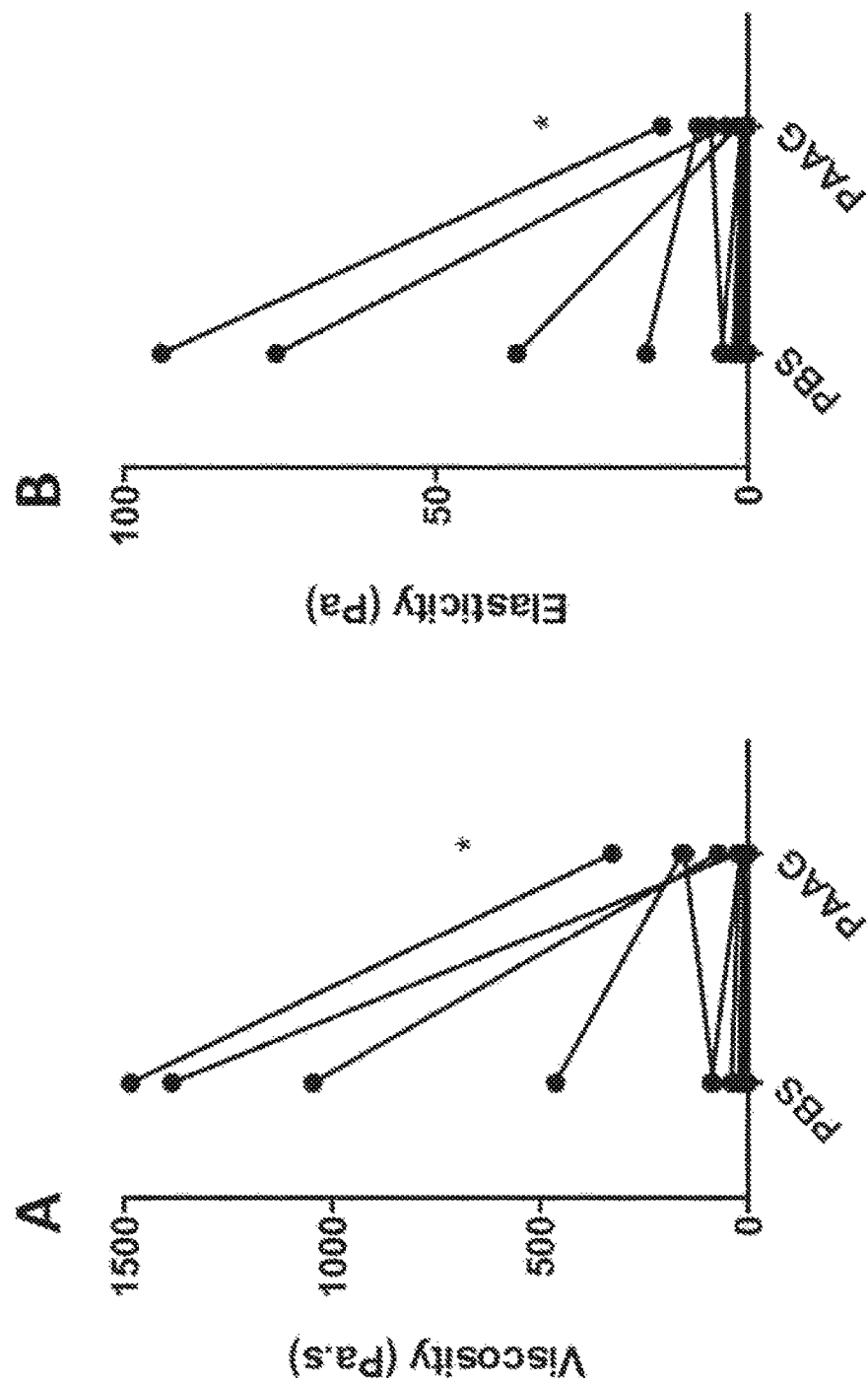
FIG. 19. Representative pOOT images of respiratory epithelia used to measure the effect of PAAG on airway surface liquid (ASL) thickness, ciliary beat frequency (CBF), and mucociliary transport (MCT).

Results:

Significantly reduced viscosity was observed at low strain forces, consistent with a therapeutic benefit of PAAG without the influence of high strain induced deformation (FIG. 18). Significantly lower viscosity (FIG. 19*a*) and elasticity (FIG. 19*b*) was observed in PAAG treated samples compared to PBS treated samples These data confirm the previously observed in vitro reduction in bacterial biofilm spent media and viscosity and increase in pourability in sputum.

Protocol:

Primary human bronchial epithelium (HBE) cells were derived from lung explants. First or second passage cells, which underwent expansion and attained confluency, were seeded onto 6.5 mm diameter permeable supports ($0.5\times10^6$ cells per filter, Corning Inc., Corning, New York) coated with NIH 3T3 fibroblast unconditioned media. Cells were grown in differentiating media for at least 6-8 weeks until terminally differentiated. In some experiments, HBE cells from a normal donor were cultured in media depleted of bicarbonate, with and without acetazolamide (100 μM). HBE cells derived from CF and non-CF donors were imaged for ASL depth following treatment with PAAG (70 kDa, 28% functionalized, 1.6 PDI).

HBE cells obtained from CF patients homozygous for F508del were washed in PBS for 15 minutes, treated with various concentrations of PAAG, and combined with 10 μL of 500 nm particles in a 1:120 dilution in PBS. The mucociliary transport of the cells was then observed by μOCT imaging techniques. The cells were then treated with benzalkonium chloride 0.01% media mixture for an hour to stop ciliary motion. The cells were washed in media for 15 minutes and then allowed to incubate at 37° for at least 3 hours. A fluorescent microscope and MetaMorph software were used to take videos of the fluorescent particles in the ASL layer of the cells. TRITC was used to image particles. Using the 20× objective lens and 50 ms of exposure time, four videos of different regions of interest in different quadrants in the filter were recorded.

Results: HBE cells derived from CF and non-CF donors were imaged for ASL depth. Representative μOCT images of CF HBE monolayers treated with PBS control (FIG. 20*a*) or PAAG (500 μg/ml ASL concentration, 24 hrs) (FIG. 20*b*) demonstrated clearly reduced reflectivity of the mucus layer following PAAG treatment, indicating reduced viscosity in situ without altering integrity of the cell monolayer. Scale=50μη. Fluorescent image of WT HBE monolayer treated with 250 μg/mL of PAAG-FITC shows PAAG intermingles within the mucus layer (FIG. 20*c*). The scale bar=10μηt. Quantitative data from μOCT video imaging-rate imaging showed increased mucociliary transport (FIG. 20*d*) and improved ciliary beat frequency (FIG. 20*e*) following PAAG treatment. *P<0.05, ****P<0.0001, N=4/condition. These data indicate that PAAG's ability to reduce viscosity and elasticity of mucus ex vivo and in relation to human epithelial cells will likely translate into clinically significant mucolytic activity.

Example 8: PAAG Reduces Intracellular Survival

Protocol:

The uptake of *Burkholderia cepacia* subspecies *cepacia* (ATCC 25416) and *Burkholderia cepacia* subspecies *cenocepacia* (clinical isolate, Seattle Hospital, WA) into differentiated human U937 macrophages (PMA 48 hours) was examined. The bacteria and macrophages were each rinsed twice with PBS and bacteria were inoculated onto the macrophages at a multiplicity of infection (MOI) of 1:10 following a 5-60 minute PAAG treatment (200 μg/mL) that was either rinsed away or not before inoculation. Also, one treatment examined pre-incubating the bacteria with PAAG (30.7% functionalization, 86.53 kDa, 87.92 DDA, 1.63 PDI) 60 minutes prior to inoculation. The cells were then incubated with 5% CO at 37° C. for 30 minutes before a 45 minute 100 μg/mL gentamicin treatment to kill extracellular bacteria. Intracellular bacteria were enumerated by plate count after lysing ceils with 1% Triton X.

Results:

Figure 21:
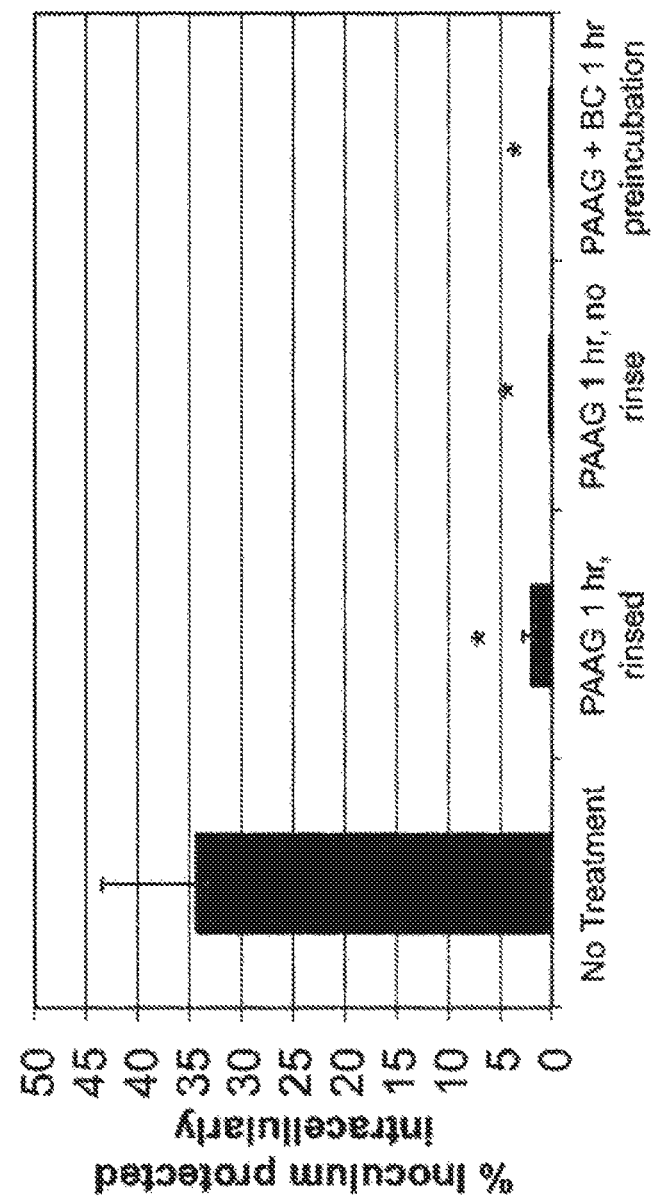
FIG. 21. The gentamicin protection assay shows 1 hour pretreatment of bacteria or macrophages with PAAG at 200 µg/mL final concentration reduces intracellular uptake of Burkholderia cepacia in U937 human macrophages.
Figure 23:
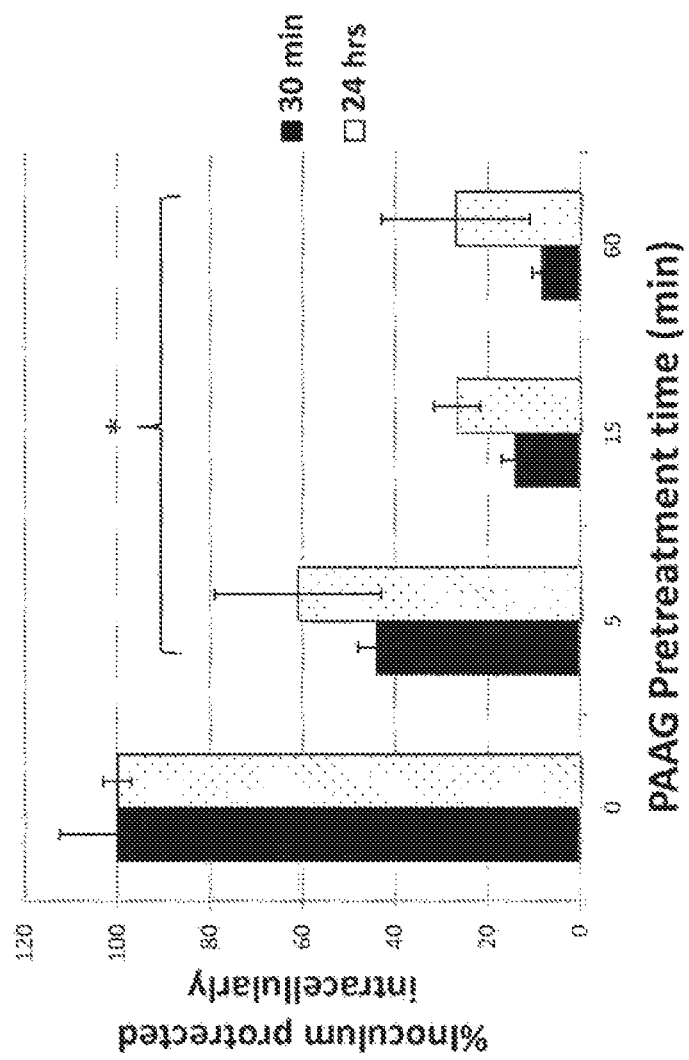
FIG. 23. The gentamicin protection assay shows 5-60 minutes pretreatment of macrophages with PAAG at 200 µg/mL final concentration reduces intracellular survival of Burkholderia cepacia in U937 human macrophages.
Figure 24:
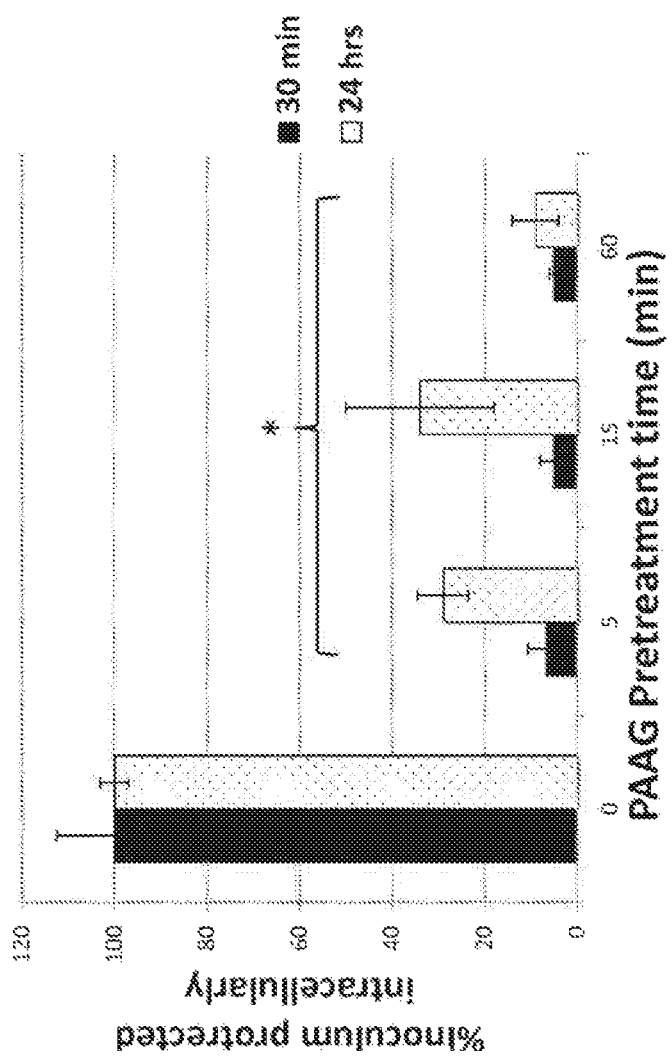
FIG. 24. The gentamicin protection assay shows 5-60 minutes pretreatment of macrophages with PAAG at 200 µg/mL final concentration reduces intracellular survival of Burkholderia cepacia strain Cenocepacia in U937 human macrophages.
Figure 25:
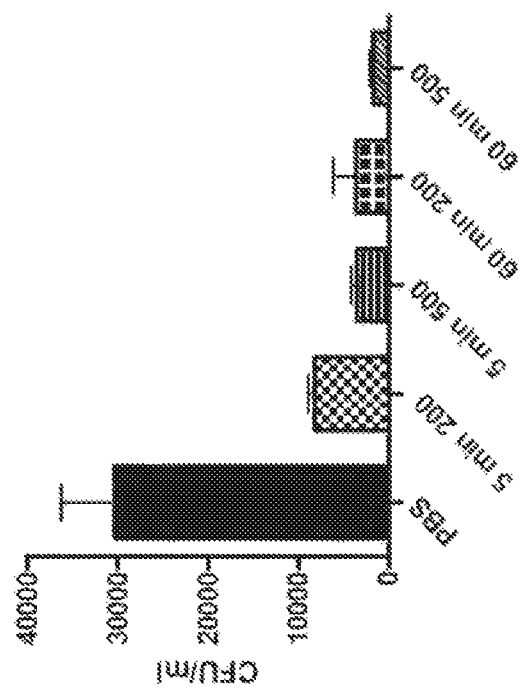
FIG. 25. PAAG treatment in PBS at either 200 or 500 µg/mL final concentration for 5-60 minutes reduces MRSA attachment to nasal epithelial cells.
Figure 26:
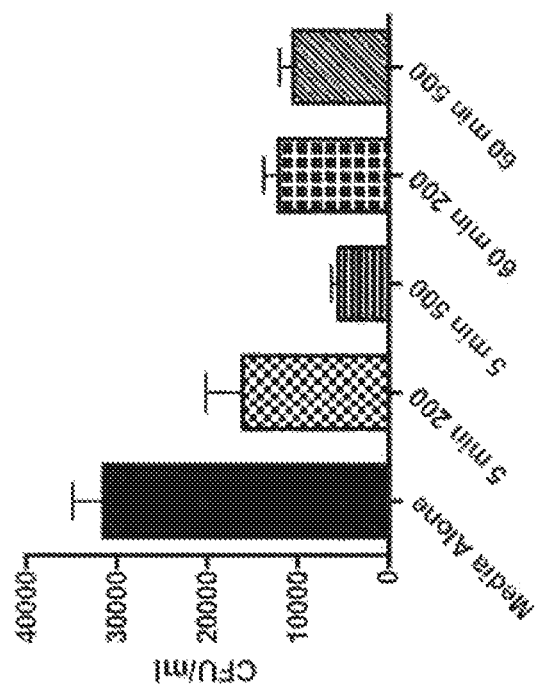
FIG. 26. PAAG treatment in tissue culture media at either 200 or 500 µg/mL final concentration for 5-60 minutes reduces MRSA attachment to nasal epithelial cells.
Figure 27:
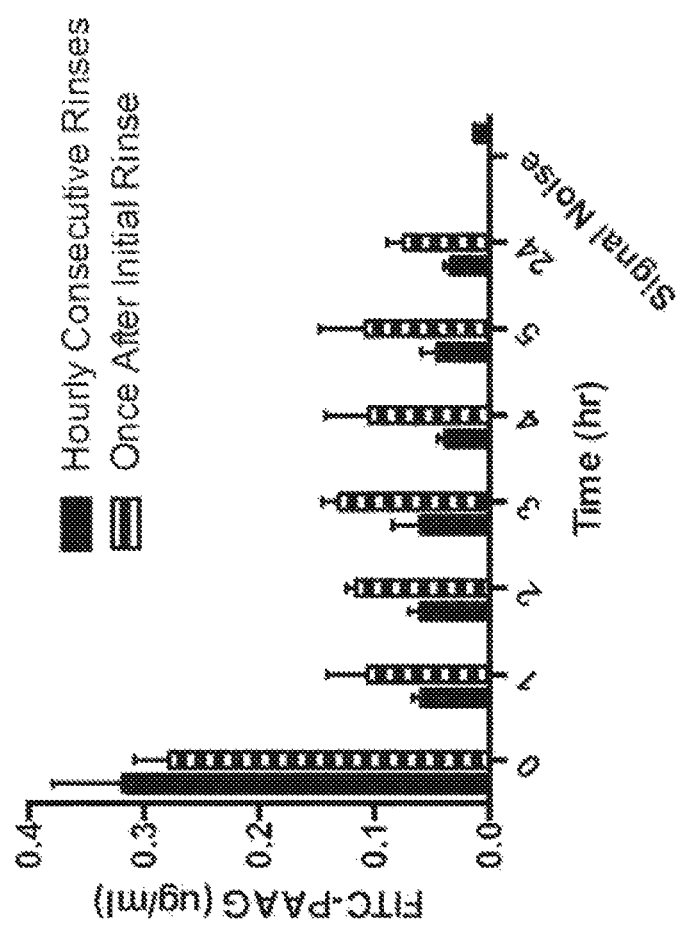
FIG. 27. Mucoadhesivity of FITC-labeled PAAG at 200 µg/mL final concentration to human lung epithelial cells over 24 hours.

*Burkholderia* is a significant problem in the ability of the bacteria to subvert the host immune response and escape elimination by surviving intracellularly within host immune cells, specifically macrophages. FIG. 21 shows a protection assay that measured the percent (%) intracellular *Burkholderia* within human U937 macrophages inoculated with *B. cepacia* was significantly reduced following various pretreatments with 200 μg/ml PAAG (*$p<0.0^3$). FIG. 22 shows a protection assay that measured the percent (%) intracellular *Burkholderia* within human U937 macrophages inoculated with *B. cenocepacia* following various pretreatments with 200 μg/ml PAAG (*p<0.03). This study shows that either pre-treatment of macrophages or the bacteria with PAAG is able to reduce macrophage uptake of *Burkholderia*, including a clinically relevant isolate.

Protocol:

The survival of *Burkholderia* strains into differentiated human U937 macrophages (PMA 48 hours) was examined. The bacteria and macrophages were each rinsed twice with PBS and bacteria were inoculated onto the macrophages at a multiplicity of infection (MOI) of 1:10 following a 5-60 minute PAAG 30.7% functionalization, 86.53 kDa, 87.92 DDA, 1.63 PDI) treatment (200 μg/ml) that was either rinsed away or not before inoculation. Also, one treatment examined pre-incubating the bacteria with PAAG 60 minutes prior to inoculation. The cells were then incubated with 5% CO at 37° C. for 30 minutes before a 45 minute 100 μg/mL gentamicin treatment to kill extracellular bacteria, intracellular bacteria were enumerated by plate count after lysing cells with 1. Triton X.

Results:

*Burkholderia* is a significant problem in the ability of the bacteria to subvert the host immune response and escape elimination by surviving intracellular!}—within host immune cells, specifically macrophages, FIG. 23 shows a protection assay to determine the percent (%) intracellular *B. cepacia* in human U937 macrophages after 30 minutes and 24 hours following a 5, 10, or 60 minute pretreatment with 50 µg/mL PAAG relative to untreated control. All PAAG treated cells showed significant reduction in intracellular bacteria (* indicates p<0.02). FIG. 24 show a protection assay to determine the percent (%) intracellular *B. cenocepacia* in human U937 macrophages after 30 minutes and 24 hours following a 5, 10, or 60 minute pretreatment with 200 µg/mL PAAG relative to untreated control. All PAAG treated cells showed significant reduction in intracellular bacteria (* indicates p<0.02). This study shows that pretreatment of macrophages with PAAG is able to significantly reduce macrophage uptake of *Burkholderia*, including a clinically relevant isolate in a time dependent manner.

Example 9: PAAG Reduces MRSA Attachment to Epithelial Cells

Protocol:

The ability of *S. aureus* (MW2) to adhere to RPMI 2560 nasal epithelium cells was assessed to determine the feasibility of PAAG to prevent and remove bacteria growth in the nasal cavity. By binding to the surface of mammalian cells that represent the interface between gut lumen and mucosa. PAAG reduces the ability of bacteria to adhere, colonize, and initiate biofilm formation. The RPMI 2650 cell line (American Type Culture Collection) was seeded in 24-well cell culture plates at $2.5\times10^5$ cells per well. Cells were grown in Eagle's Minimal Essential Medium (EMEM) containing 10% fetal calf serum, 2 mM L-glutamine without antibiotics for 24 hours at 37° C. in atmosphere containing 5% $CO_2$. Confluent monolayer was washed once with DPBS and replaced with EMEM without serum 2 hours prior to start of experiment. Cells were pretreated for 5 minutes or 1 hour with either 200 μg/ml or 500 μg/ml of PAAG (30.7% functionalization, 86.53 kDa, 87.92 DDA, 1.63 PDI) in either PBS or EMEM without serum or antibiotics. After the pretreatment of PAAG, each well was rinsed once with DPBS and replaced with EMEM without serum or antibiotics. The day prior to experiment, an overnight culture was initiated for *S. aureus* MW2, subsequently the overnight culture optical density was measured at the time of inoculation to provide an MOI of 1:100. Bacteria was given 1 hour from the start of the inoculation to adhere to epithelium monolayer, non-adherent cells were washed away with 2× rinses of DPBS to prevent nonspecific binding. Epithelium monolayer was lysed with 0.1% Triton X-100. Bacteria were quantified by plating serial dilutions of the lysate. All quantitative adherence assays were performed in triplicate.

Results:

At higher concentrations and longer treatment times, PAAG significantly prevented the attachment of MW2 onto nasal epithelium cells. PAAG dissolved in either (EMEM) media (FIG. 25) or PBS (FIG. 26) showed significantly decreased attachment, although PAAG dissolved in PBS was more effective. The increased amount of buffers, nutrients and proteins in EMEM seem to reduce the activity of PAAG but is still effective at blocking binding of bacteria to the epithelial cells. This may suggest PAAG will bind to debris in the nasal cavity to facilitate removal and that activity at the surface and in the nasal cavity could be maintained with higher doses.

Protocol:

PAAG, like other polycationic polyglucosamines is also strongly mucoadhesive providing some residency time during treatment. An adhesion assay was done where A549 human lung epithelial cells were pre-treated with 200 μg/mL FITC/PAAG (26% functionalization, 34 kDa, 87.88 DDA, 1.3 PDI) for 30 minutes. Cells were either rinsed hourly (for rigorous rinsing) or rinsed only once after initial rinse at hours 1-5 and 24, prior to measuring the level of fluorescence.

Results:

The mucoadhesion of PAAG to Human lung epithelial cells was examined. When the more rigorous rinsing was applied the level of fluorescence measured at 3-hours versus 24-hour rinsing was not significantly different however, it maintained a 30-fold increase over background FITC/PAAG control (FIG. 27). The less rigorous rinsing showed no significant difference between 1-hour versus 24-hour rinse however, it maintained a 44-fold increase over background FITC/PAAG control (FIG. 27). These data support the idea that PAAG associates strongly with cell surfaces.

Example 10: PAAG Modulates Inflammatory Cytokine Production

Background:

Research into multiple sources of induced damage to tissues suggests that there are common downstream biological pathways that arise from physical, chemical, radiative or pathogenic mediators. The healing is limited by the downstream activation of inflammatory pathways, stimulated by an initial release of reactive oxygen species. This inflammatory activation leads to further tissue damage that limits healing, and in some cases, results in chronic inflammation and substantial scarring. Recent studies suggest that the mechanisms of mucosal, tissue and epithelial damage after initiation are mediated by some of the most primitive innate immune responses, such as those mediated by the toll-like receptors (TLR's) and Nod-like receptors (NLR's). The fundamental mediators of inflammation are linked through a common pathway that can be induced by the pathogen associated molecular pattern molecules (PAMP's), damage associated molecular patterns molecules (DAMP's) and chemical and radiation associated molecular pattern molecules (CRAMP's). The molecules likely actuate the process through interaction with TLR's and are responsible for the activation of common pathways associated with inflammation, damage and inability to heal.

Protocol:

The THP-1 human monocytic cell line was derived from one-year old male with acute lymphocytic leukemia. The cells are grown in suspension culture and can be differentiated to more macrophage-like cells using calcitriol, a vitamin D analog, or the phorbol ester PMA (phorbol 12-myristate 13-acetate). When PMA is used the cells become adherent and the literature suggests that cells are more differentiated than when treated with calcitriol. THP-1 cells were differentiated in the presence of PMA for 48 hours before being pretreated with PAAG (25% functionalization, 18 kDa) for 1 hour then stimulated by the addition of LPS, an endotoxin that results in the expression of the pro inflammatory cytokine TNFa.

In a similar study, human U937 macrophages were seeded at $10^7$ cells/ml and activated with PMA for 24 hours. The supernatant was exchanged and after 24 hours the macrophages were treated with media alone or 200 ppm PAAG (25% functionalization, 18 kDa) for 1 hour. The media was exchanged and the macrophages were stimulated with either bacterial DNA (5 hours) or LPS (4 hours). The IL-8 produced by the macrophage was measured by ELISA at 4 and 24 hours.

Figure 28:
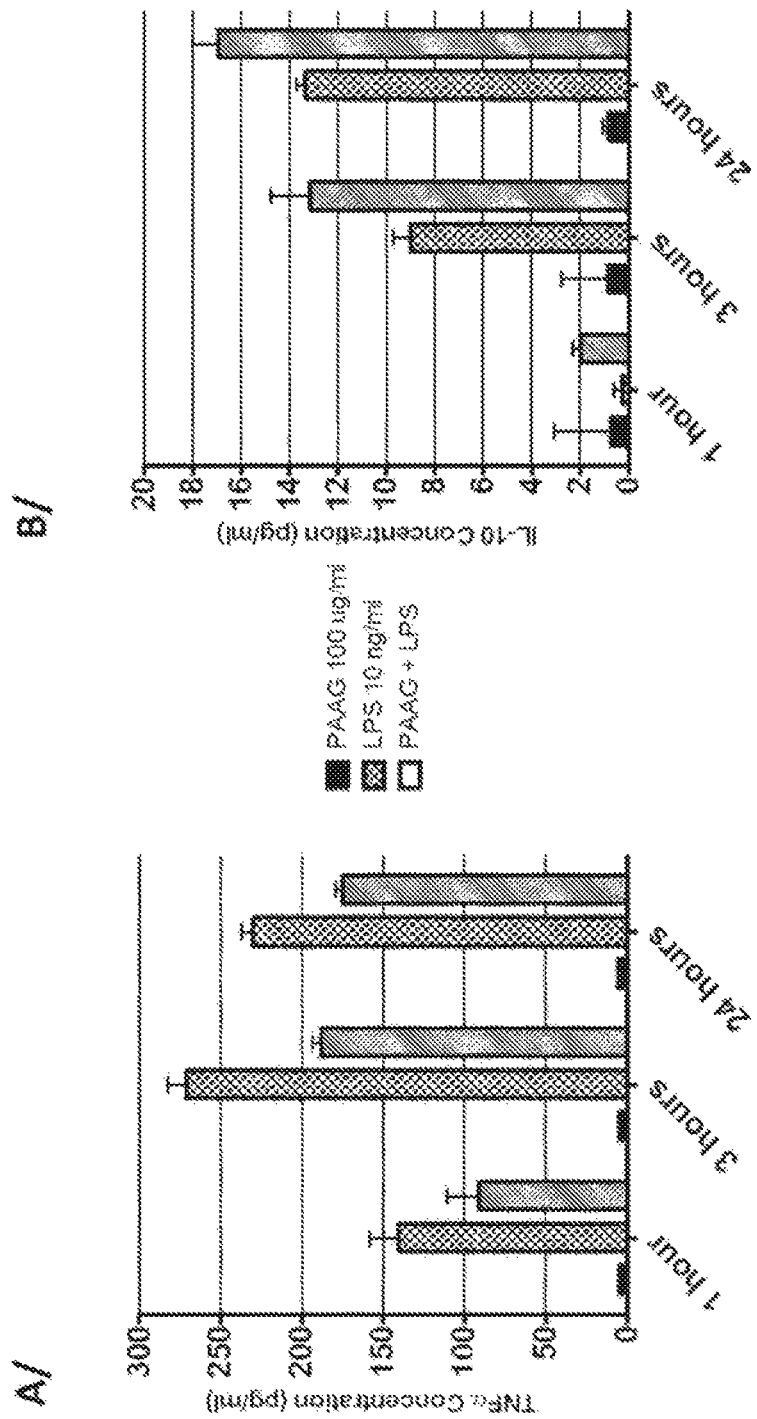
FIG. 28. Pretreatment of human macrophages with PAAG at 100 µg/mL final concentration reduces LPS stimulated TNF-α (A) and IL-10 (B) secretion over 24 hours.

Results:

In the presence of PAAG, the expression of TNFa in THP-1 human monocyte cell line is reduced compared to cells treated with LPS alone (FIG. 28, A). We also examined the expression of an anti inflammatory cytokine. IL-10, and found that its expression is increased in the presence of PAAG (FIG. 28, B). These data suggest that PAAG can affect the balance of cytokine production from activated macrophages. One of the mechanisms of PAAG in mitigating GI damage maybe through the protection of the epithelial cells from bacterial stimulation or modulation of the innate immune response. In non-adherent immune cells, THP-1 human monocyte cell line, PAAG added after endotoxin (LPS) stimulation reduces the inflammatory TNF-α response relative to the response initiated by LPS alone without treatment also PAAG is observed to increase the relative response of an anti-inflammatory cytokine. IL-10 (FIG. 28). Although the modulation of cytokine production is subtle (i.e., not completely blocking or stimulatory), it suggests a role of PAAG in shifting the response of the cell towards homeostasis.

Protocol:

The myeloid cell line (U937) was grown in RPMI 1640 supplemented with 10% (v/v) fetal bovine serum and 2 mm L-glutamine. Cells were seeded at $6 \times 10^5$ cells per well in 24 well plates in RPMI 1640 additionally supplemented with 0.1 µg PMA for 48 hours to activate U937 cells to be macrophage like. Cell media was replaced with media without fetal bovine serum and PMA for at least 2 hours. The duration of pretreatment of 200 µg/ml PAAG (30.7% functionalization, 86.53 kDa, 87.92 DDA, 1.63 PDI) was one hour before being rinsed twice with D-PBS. Cells were then subjected to media containing MW2 DNA for activation (except media control). MW2 DNA was isolated from a grown culture using a Qiagen DNA extraction kit. Supernatants were extracted and stored after 5 and 24 hours from the time of DNA stimulation. An IL-8 ELISA was performed according to the BioLegend protocol.

Figure 29:
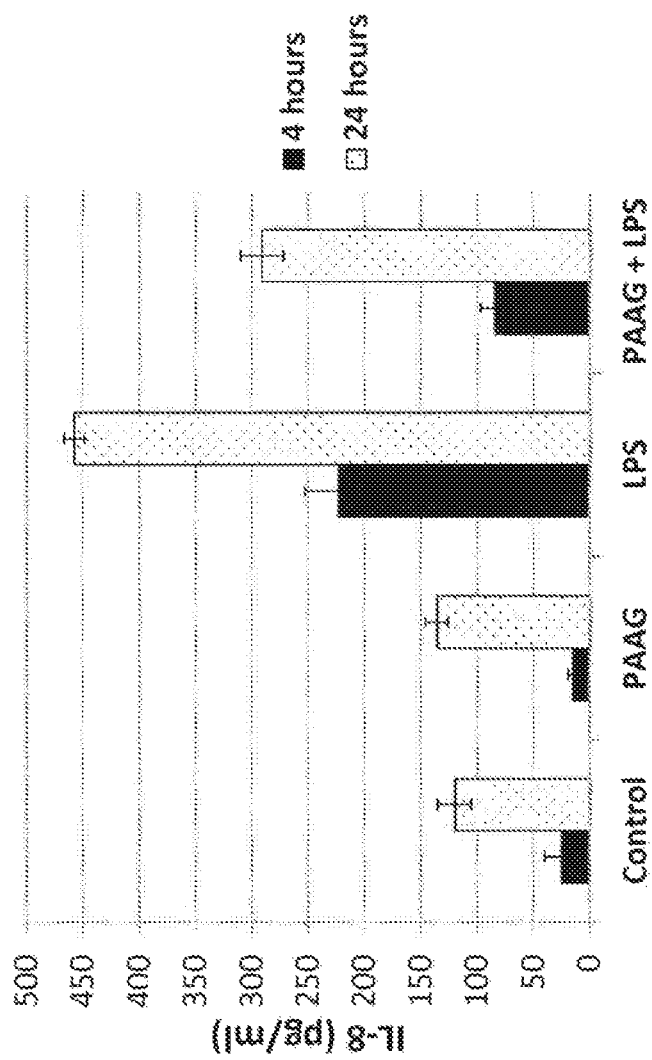
FIG. 29. Pretreatment of human macrophages with PAAG at 200 µg/mL final concentration reduces LPS stimulated IL-8 secretion at 4 and 24 hours.
Figure 30:
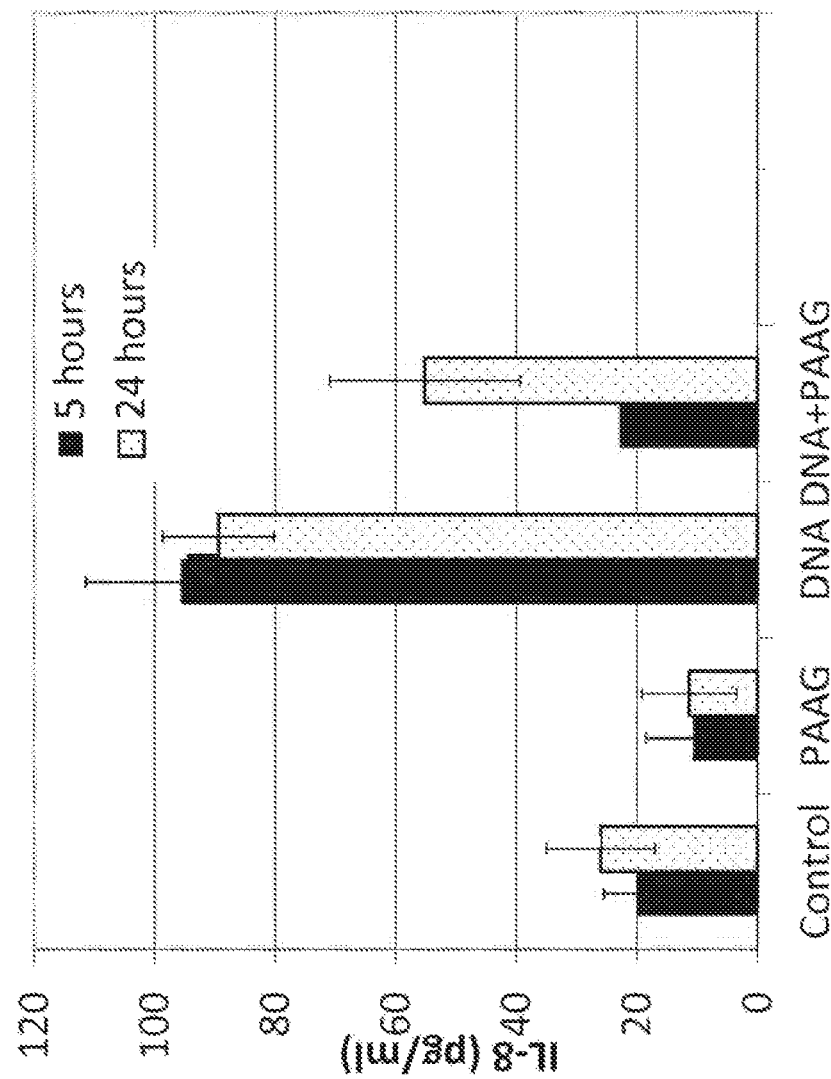
FIG. 30. Pretreatment of human macrophages with PAAG at 200 µg/mL final concentration reduces bacterial DNA stimulated IL-8 secretion at 5 and 24 hours.

Results:

Macrophages pre-treated with 200 ug/ml PAAG for 1-hour secreted significantly less IL-8 ($p<0.00^2$) after 4 and 24 hours compared to LPS treatment alone (FIG. 29). Human U937 macrophages pre-treated with 200 ug/ml (30.7% functionalization, 86.53 kDa, 87.92 DDA, 1.63 PDI) for 1-hour showed significant decrease in IL-8 secretion within 5 hours and a moderate decrease in 24 hours versus cells not treated with PAAG stimulated by MW2 DNA (FIG. 30). This study shows the ability of PAAG to modulate the immune response by reducing the amount of IL-8 produced by macrophages, pivotal in the amplification of a proinflammatory immune response.

Protocol:

Activated macrophages were exposed to various treatment combinations of PAAG, Lactoferrin. and LPS. The human myeloid cell line (U937) was propagated in RPMI 1640 supplemented with 10% (v/v) fetal bovine serum and 2 mm L-glutamine. Cells were seeded at $6 \times 10^5$ cells per well in 24 well plates in RPMI 1640 additionally supplemented with 0.1 ug PMA for 48 hours to activate U937 cells to be macrophage-like. Cell media was replaced with media without fetal bovine serum and PMA for at least 2 hours. The duration of pretreatments of Lactoferrin (100 ng/ml), and PAAG (30.7% functionalization, 86.53 kDa, 87.92 DDA, 1.63 PDI) at 200 ug/ml was one hour before being rinsed twice with D-PBS. Cells were then subjected to media containing LPS (10 ng/ml) for IL-8 stimulation. Supernatants were extracted and stored after 4 hours from the time of LPS stimulation. An IL-8 ELISA was performed according to the BioLegend protocol to measure IL-8 production.

Figure 31:
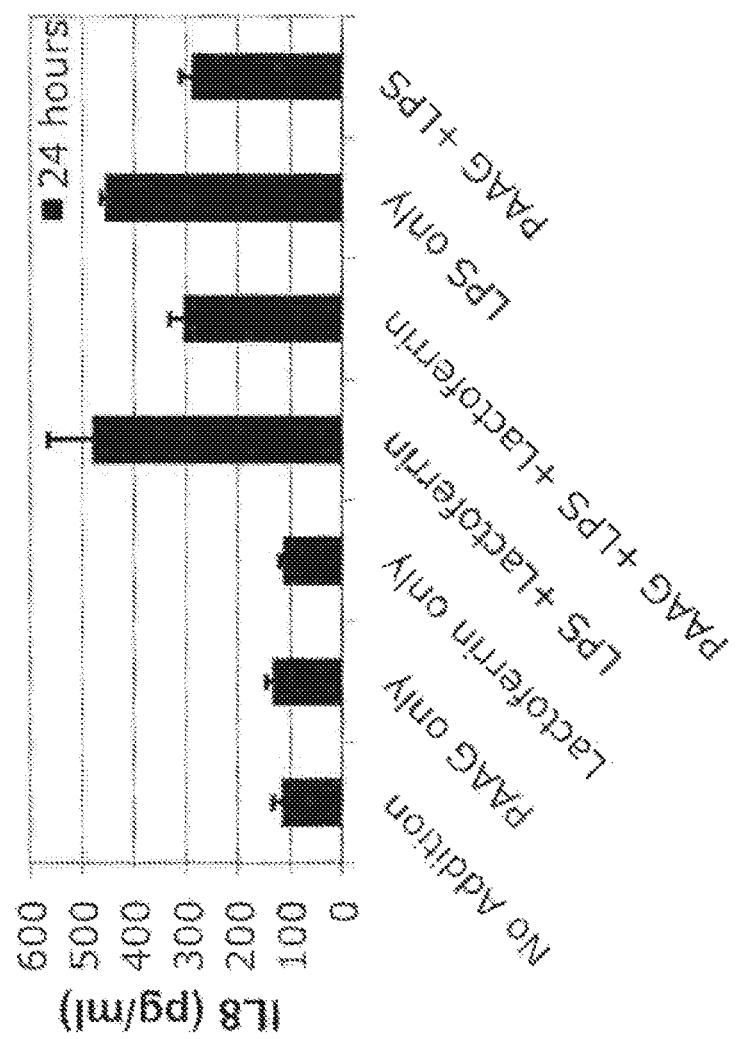
FIG. 31. Pretreatment of human macrophages with PAAG at 200 µg/mL final concentration reduces more LPS stimulated IL-8 secretion after 24 hours compared to lactoferrin treatment FIG. 32. Pretreatment of human epithelial cells with PAAG at 200 µg/mL final concentration for 1 hour reduces bacterial stimulated IL-8 secretion after 24 hours.

Results:

Macrophages subjected 200 µg/ml PAAG or 100 ng/ml lactoferrin pretreatment for 1 hour prior to stimulation with LPS treatment showed the same magnitude of IL-8 secretion suppression as lactoferrin at 24 hours (FIG. 31).

Protocol:

The effect of PAAG (30.7% functionalization, 86.53 kDa, 87.92 DDA, 1.63 PDI) on the modulation of bacteria inflammatory mediators in vitro was examined PAAG also protects immune cells such as macrophages and monocytes from activation by bacteria. Macrophages (U937) and epithelial cells (A431) were used as to examine PAAG's ability to reduce IL-8 secretion in the presence of bacteria. After 1-hour pretreatment with 200 µg/ml PAAG or vehicle, the macrophages were rinsed and incubation with bacteria. After 24 hours, ELISA measured the cell supernatant IL-8 concentration.

Figure 32:
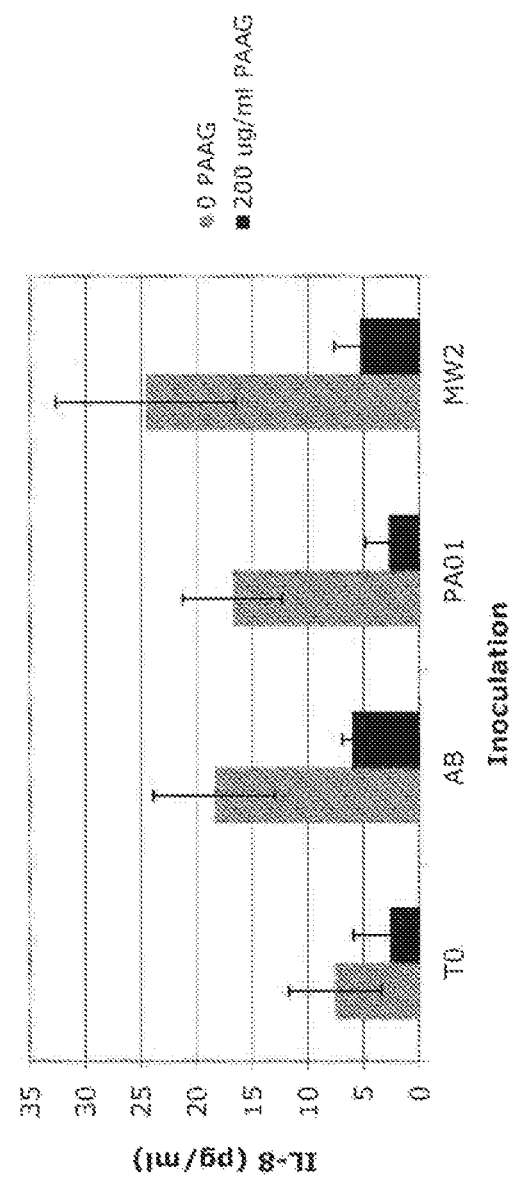
Figure 33:
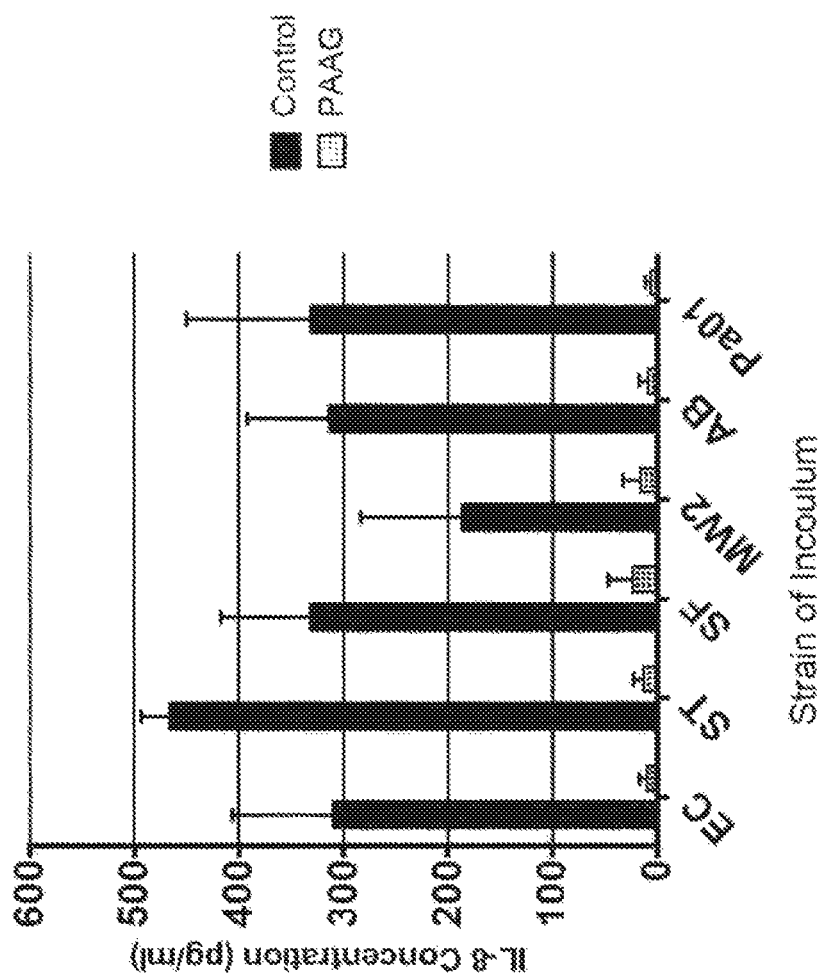
FIG. 33. Pretreatment of human macrophages with PAAG at 200 µg/mL final concentration for 1 hour reduces bacterial stimulated IL-8 secretion after 24 hours.

Results:

An ELISA examined the supernatant for IL-8 after 24-hours and is shown in FIGS. 32-33. Pre-treating with PAAG prior to exposure to bacteria significantly reduced the IL-8 secretion from epithelial cells (FIG. 32) as well as macrophages (FIG. 33). Since IL-8 is a strong neutrophil chemokine, the results suggest that the downstream immune response in vivo will be reduced and that neutrophils will be less stimulated.

Example 11: Cation/Osmolyte Influences on PAAG Biological Activity Against Planktonic and Biofilm Bacterial Protocol:

The antibacterial activity of 100 µg/mL PAAG against panktonic MRSA (strain MW-2) in the presence of increasing concentrations of NaCl was analyzed after 24 hours treatment. The bacteria were treated with 0, 50, 150, or 250 mM of either NaCl alone or followed by treatment with 100 µg/mL PAAG (25% functionalization, 28 kDa).

Figure 34:
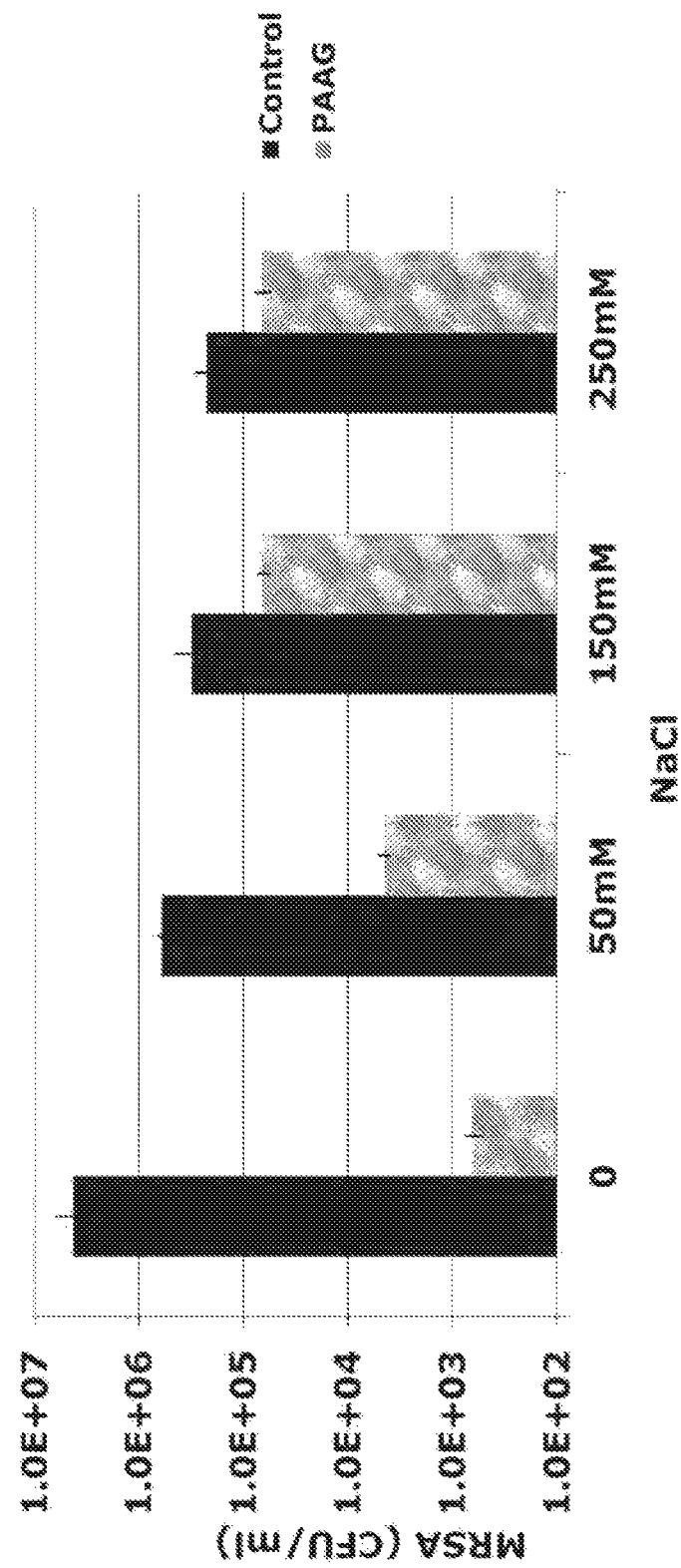
FIG. 34. Influence of increasing NaCl concentrations on PAAG activity against MRSA.

Results:

The assay shows that NaCl protects MRSA (strain MW-2) from 100 µg/mL PAAG antimicrobial activity. As the concentration of NaCl increases more bacteria are recoverable after 100 µg/mL PAAG treatment (FIG. 34). This suggests PAAG antimicrobial activity is reduced in a dose dependent manner in the presence of NaCl.

Protocol:

The antibacterial activity of 100 µg/mL PAAG against panktonic MRSA (strain MW-2) in the presence of increasing concentrations of $CaCl_2$ was analyzed after 24 hours treatment. The bacteria were treated with 0, 50, 150, or 250 mM of either $CaCl_2$ alone or followed by treatment with PAAG (25% functionalization, 28 kDa).

Figure 35:
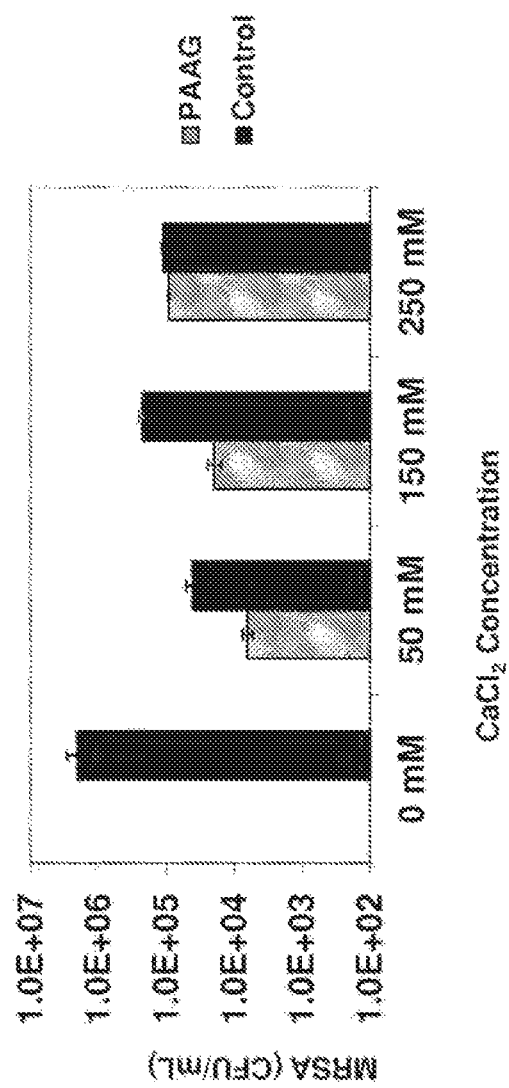
FIG. 35. Influence of increasing $CaCl_2$ concentrations on PAAG activity against MRSA.

Results: As the concentration of $CaCl_2$ increases more bacteria are recoverable after 100 µg/mL PAAG treatment compared to control (FIG. 35). This suggests PAAG antimicrobial activity is reduced in a dose dependent manner in the presence of $CaCl_2$.

Protocol:

The antibacterial activity of 100 µg/mL PAAG against panktonic *P. aeruginosa* (strain PAOI) in the presence of increasing concentrations of $MgCl_2$ was analyzed after 24 hours treatment. The bacteria were treated with 0, 50, 150, or 250 mM of either $MgCl_2$ alone or followed by treatment with 100 µg/mL PAAG (25% functionalization, 28 kDa).

Figure 36:
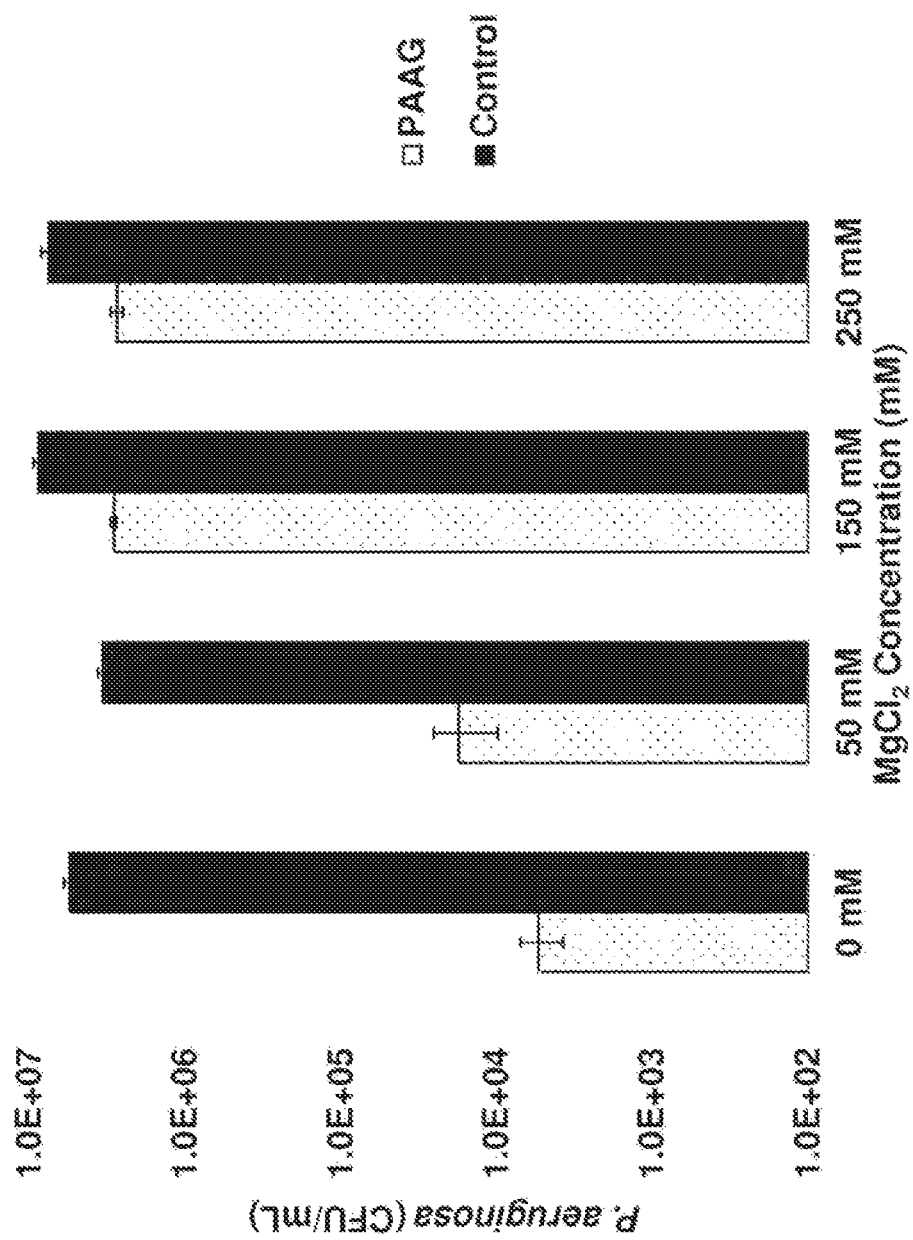
FIG. 36. Influence of increasing $MgCl_2$ concentrations on PAAG activity against P. aeruginosa.

Results:

The assay shows that MgCl$_2$ protects *P. aeruginosa* (strain PAOI) from the antimicrobial affects of PAAG in a dose dependent manner (FIG. 36). At a concentration of 150 mM the antimicrobial activity of PAAG is reduced to untreated levels.

Protocol:

The antibacterial activity of 100 μg/mL PAAG against panktonic MRSA (Strain MW-2) in the presence of increasing concentrations of osmolyes (Trehalose) was analyzed after 24 hours treatment. Trehalose is a natural osmolyte and retains water and may help stabilize cells after cell wall damage. The bacteria were treated with 0, 50, 150, or 250 mM of either osmolyte alone or followed by treatment with 100 μg/mL PAAG (25% functionalization, 28 kDa).

Figure 37:
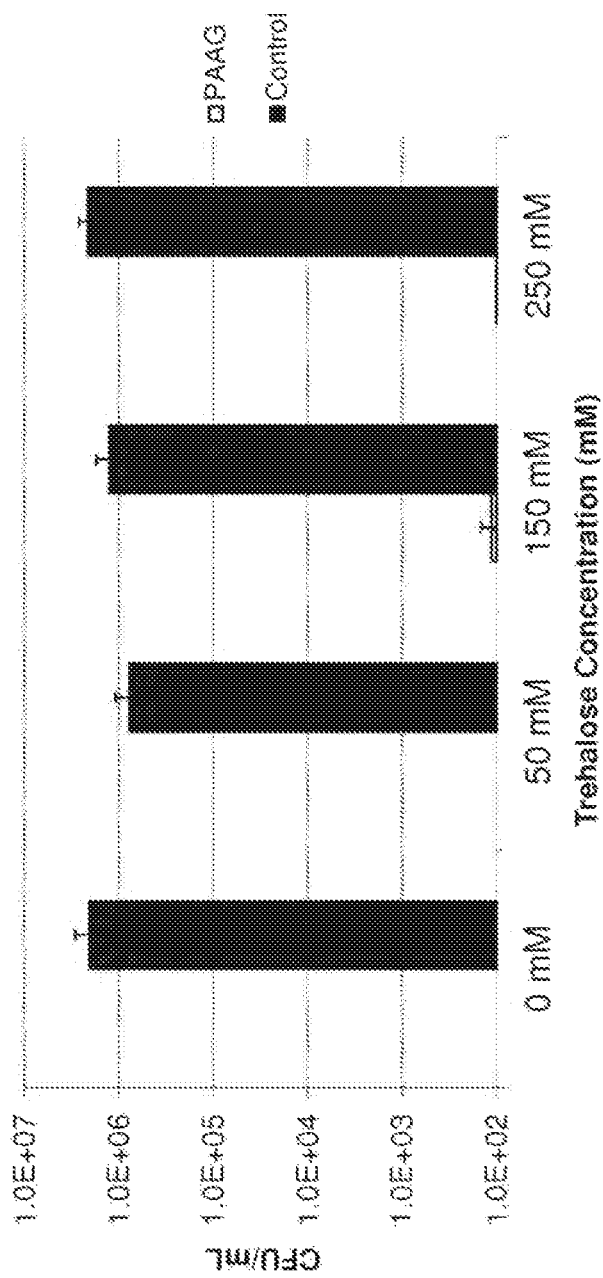
FIG. 37. Influence of increasing Trehalose concentrations on PAAG activity against P. aeruginosa.

Results:

The assay shows that the osmolyte trehalose does not protect *P. aeruginosa* (strain PAOQ) from the effects of PAAG (FIG. 37). Regardless of the amount of trehalose present PAAG was able to maintain antimicrobial activity.

Protocol:

Stationary biofilms of *P. aeruginosa* SUS116 were grown in TSB with 1% glucose overnight at 37° C. in 96-well plates. The plates were washed once with sterile water then the PAAG (28% functionalization, 70 kDa, 1.6 PDI, 88% DDA) treatments were applied for 1-4 hours. Treatments included: 50-400 ug/ml PAAG with and without 150 mM Calcium Chloride (4-hour treatment only), 200-1600 ug/ml PAAG with and without 400) mM Calcium Chloride (I and 4-hour treatments). Biofilms were washed one time with sterile water, dried then fixed with 95% ethanol. Crystal violet (0.4%) was used to dye the biofilm for 1 hour then removed and washed twice with water. Acetic acid was applied to the dyed biofilms to elute the retained dye then collected and the OD was read to determine the amount of biofilm remaining in the well.

Figure 38:
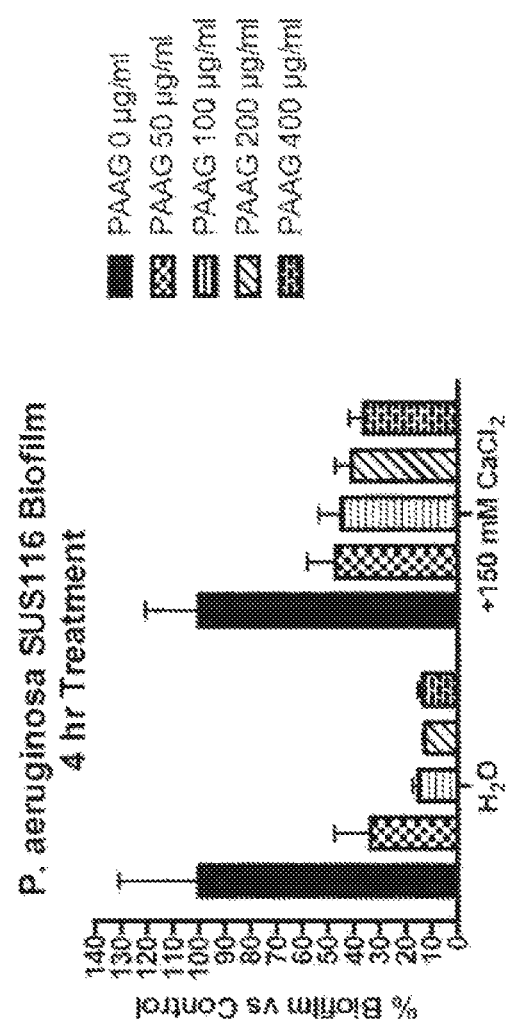
FIG. 38 Stationary biofilm removal of P. aeruginosa strain SUS116 following 4-hour treatment+/−150 mM $Ca^{++}$ FIG. 39 Stationary biofilm removal of P. aeruginosa strain SUS116 following 1-hour treatment+/−400 mM $Ca^{++}$ FIG. 40 Stationary biofilm removal of P. aeruginosa strain SUS116 following 4-hour treatment+/−400 mM $Ca^{++}$ FIG. 41 PAAG inhibits the growth of P. aeruginosa strain MR51 biofilms on skin (A431) epithelial cells.

Results:

PAAG's mechanism if action is the displacement of cations from the mucus or biofilms. Because this is an entropically driven system, an increase in external cation concentration would reduce the effect of PAAG in the short time periods, but over time, PAAG would eventually displace the ions to form the more stable complex When *P. aeruginosa* strain SUS116 biofilms were treated with PAAG in 150 mM calcium chloride for 4 hours, less biofilms were removed at all PAAG concentrations tested however, a significant amount of biofilm was removed (40-50%) and a modest dose response was observed (FIG. 38).

Figure 39:
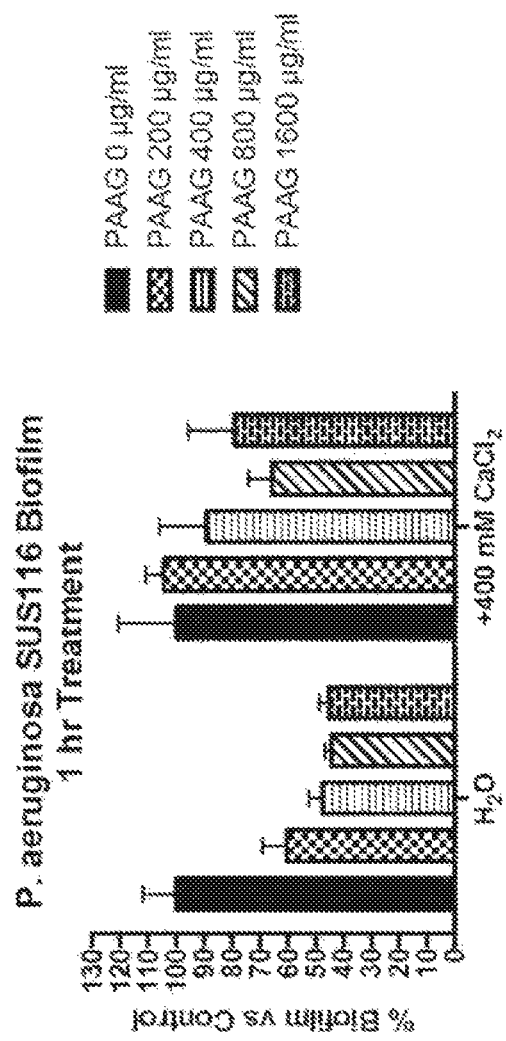
Figure 40:
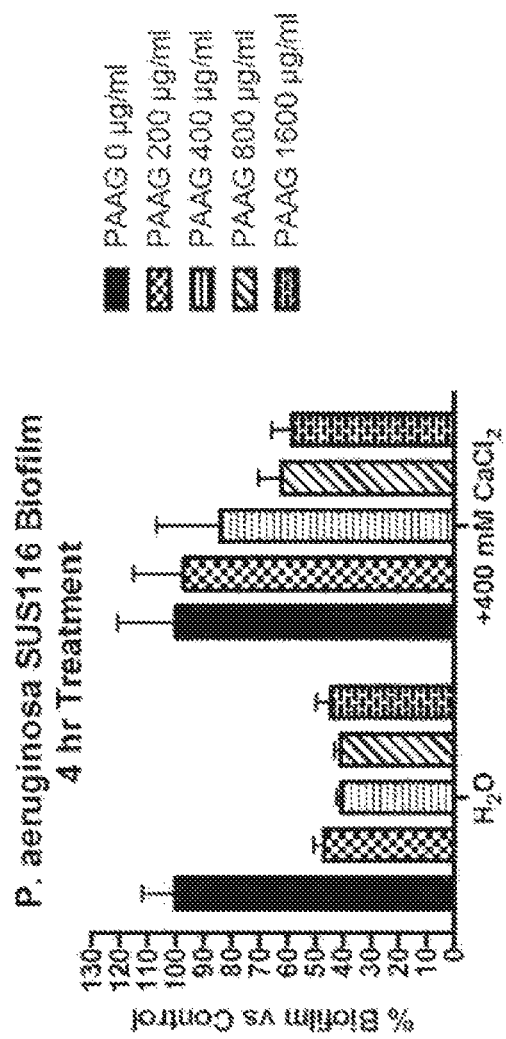

The calcium concentration was exaggerated (400 mM) and PAAG treatment increased (200-1600 ug/mL) to test extreme conditions. After 1-hour treatment *P. aeruginosa* strain SUS116 did not show an appreciable dose response in the presence of 400 mM calcium chloride (FIG. 39). After 4-hour treatment a dose response was demonstrated showing that given enough time, PAAG overcomes the influence of high cation (Calcium) concentrations to maintain biofilm removing activity (FIG. 40).

Figure 41:
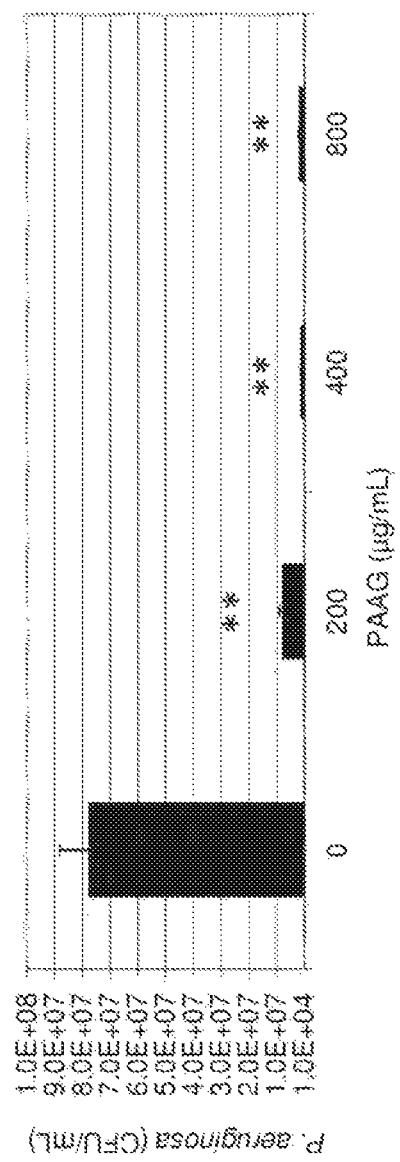

Example 12: PAAG Inhibits Biofilm Growth and Removes Biofilms from Epithelial Cell Surfaces Results:

PAAG ranging from 200 to 800 ug/mL significantly (p<0.01) reduced *P. aeruginosa* biofilms development on skin epithelial cells (A431) over 5-hour treatment period (FIG. 41). The epithelial cells treated with PAAG had 2-logs less bacteria associated with the cell surface than untreated cells. This demonstrated the ability of PAAG to adhere at the interface between biofilm and epithelial cells to prevent bacterial biofilms from developing on the cell surface.

Protocol:

Static co-culture biofilm assays were performed using *P. aeruginosa* to compare biofilm reduction/removal by PAAG. Strains of *P. aeruginosa* consisted of a multi-drug resistant and/or mucoid phenotype clinical isolates obtained from Seattle Children's Hospital and *P. aeruginosa* strain from ATCC (15692) was also tested. Human epithelial cells derived from the airway (A549) were grown in 24-well tissue culture treated plates, the bacterial were allowed to adhere for 1 hour then washed and adherent bacteria were allowed to grow biofilms in media supplemented with 0.4% arginine for 5 hours. Following biofilm growth the cells were treated with PAAG (28% functionalization, 70 kDa, 1.6 PDI, 88% DDA) for 16 hours to determine the ability of PAAG to remove biofilms from the cell surface. Following treatment the cells were washed and bacterial were quantified using viable plate counts.

Figure 42:
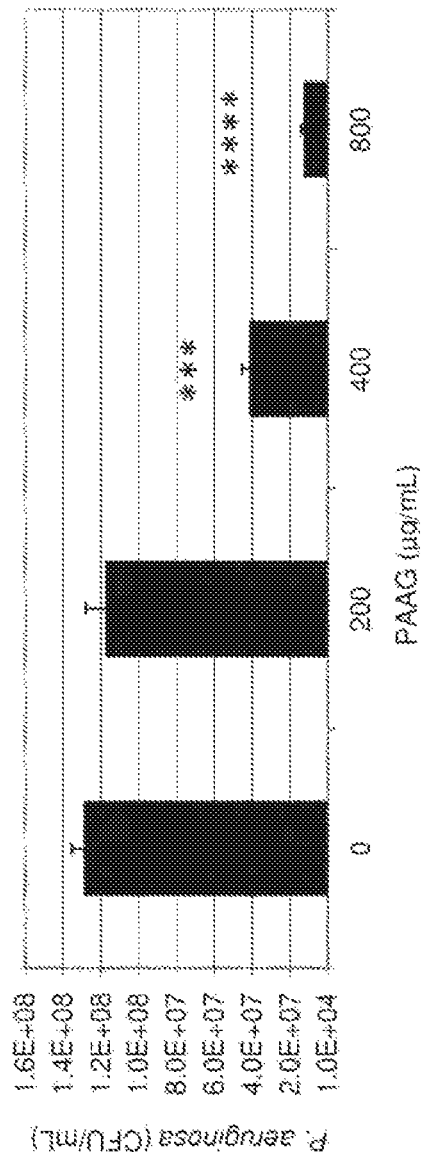
FIG. 42. PAAG inhibits the growth of P. aeruginosa strain SUS116 biofilms on skin (A431) epithelial cells.

Results:

Treatments with 400-800 ug/mL PAAG significantly (p<0.001) reduced pre-formed *P. aeruginosa* biofilms in a dose dependent manner after 16-hour treatment (FIG. 42). The epithelial cells treated with PAAG had 1-log less bacteria associated with the cell surface than control. This demonstrated the ability of PAAG to work at the interface between biofilm and epithelial cells to remove preformed bacterial biofilms and debris.

Protocol:

Static co-culture biofilm assays were performed using 4 *Pseudomonas aeruginosa* strains isolated from cystic fibrosis patients or infections to compare biofilm prevention by PAAG. Strains of *P. aeruginosa* consisted of a multi-drug resistant and/or mucoid phenotype clinical isolates obtained from Seattle Children's Hospital. Human epithelial cells derived from the airway (A549) were grown in 24-well tissue culture treated plates, the bacterial were allowed to adhere for 1 hour then treated with PAAG (28% functionalization, 70 kDa, 1.6 PDI, 88% DDA) for 5 hours to determine the ability of PAAG to inhibit biofilm formation on the cell surface. Following treatment the cells were washed and bacterial were quantified using viable plate counts.

Figure 43:
FIG. 43 PAAG inhibits the growth of P. aeruginosa strain MR51 biofilms on lung (A549) epithelial cells.
Figure 44:
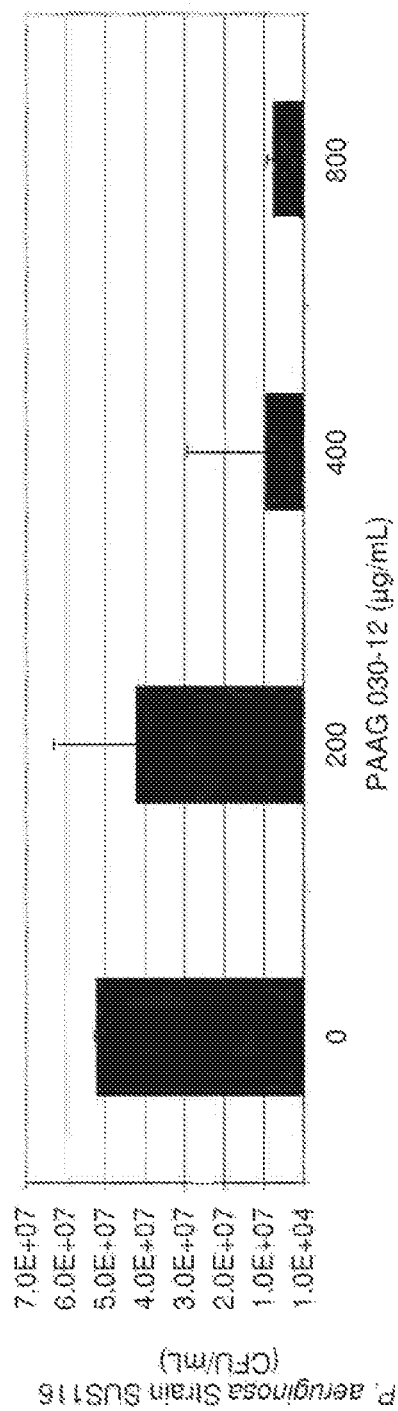
FIG. 44. PAAG inhibits the growth of P. aeruginosa strain SUS116 biofilms on lung (A549) epithelial cells.
Figure 45:
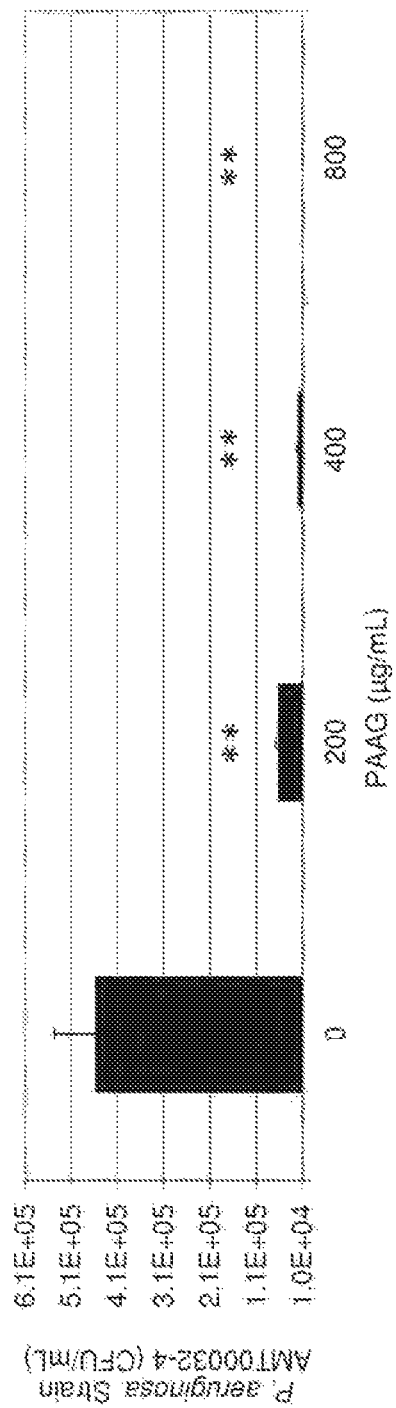
FIG. 45. PAAG inhibits the growth of P. aeruginosa strain AMT0032-4 biofilms on lung (A549) epithelial cells.

Results:

Treatment with PAAG ranging from 200 to 400 ug/mL significantly (p<0.01) reduced *P. aeruginosa* Strain MR51 biofilms development on lung epithelial cells (A549) over 5-hour treatment period (FIG. 43). The epithelial cells treated with PAAG had 1-log less bacteria associated with the cell surface, a 91% reduction, compared to untreated cells. Treatment with 800 ug/mL PAAG significantly (p>0.05) prevented the development of *P. aeruginosa* strain SUS116 biofilms from forming on the epithelial cell surface showing 85% reduction compared to untreated cells (FIG. 44). Treatment with PAAG ranging from 200 to 800 ug/mL significantly (p<0.01) reduced *P. aeruginosa* Strain AMT00032-4 biofilms development on lung epithelial cells over 5-hour treatment period (FIG. 45). The epithelial cells treated with PAAG had a 98% reduction, compared to untreated cells. This demonstrated the ability of PAAG to work at the interface between biofilm and epithelial cells to prevent clinically relevant bacterial biofilms from developing on the cell surface.

The invention claimed is:

1. A method for treating or preventing Acute Respiratory Distress Syndrome (ARDS) in a subject, the method comprising administering to the subject by inhalation an effective amount of a composition comprising a neutral osmol agent and a poly (acetyl, arginyl) glucosamine (PAAG) comprising the following formula (I):

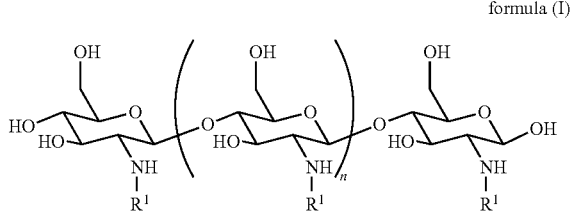

formula (I)

wherein:
n is an integer between 20 and 6000; and
each $R^1$ is independently selected for each occurrence from hydrogen, acetyl,

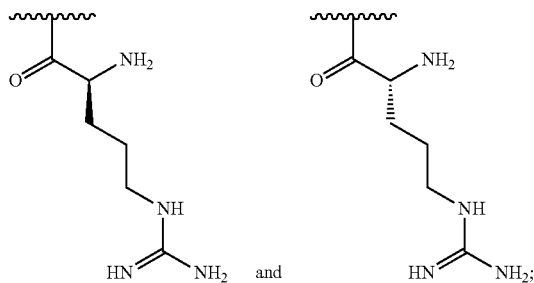 [SMILES: *C(=O)[C@@H](N)CCCNC(=N)N ; *C(=O)[C@H](N)CCCNC(=N)N]

and wherein at least 25% of $R^1$ substituents are H, at least 1% of $R^1$ substituents are acetyl, and at least 2% of $R^1$ substituents are

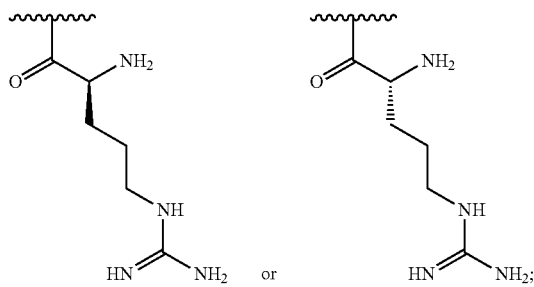 [SMILES: *C(=O)[C@@H](N)CCCNC(=N)N ; *C(=O)[C@H](N)CCCNC(=N)N]

or wherein the osmolality of the composition is between 150-550 mOsmol/kg; and
wherein the neutral osmol agent is selected from the group consisting of glycerol, sorbitol, mannitol, xylitol, erythritol, and trehalose.

2. The method of claim 1, wherein the subject has pneumonia.

3. The method of claim 1, wherein the subject has cystic fibrosis (CF), chronic pulmonary disorder (COPD), primary ciliary dyskinesia, or non-CF bronchiectasis.

4. The method of claim 1, wherein the method reduces bacterial or biofilm cohesion.

5. The method of claim 1, wherein the method increases mucociliary clearance.

6. The method of claim 1, wherein the concentration of PAAG that is administered to the subject is from about 50 µg/mL to about 600 µg/mL.

7. The method of claim 1, wherein the concentration of PAAG that is administered to the subject is about 250 µg/mL.

8. The method of claim 1, wherein the average molecular weight of the PAAG is from about 70 to about 120 kDa.

9. The method of claim 1, wherein the polydispersity index of the PAAG is from 1.0 to 2.5.

10. The method of claim 1, wherein the PAAG is arginine-functionalized at least 18%.

11. The method of claim 1, wherein the PAAG is arginine-functionalized at between 20%-30%.

12. The method of claim 1, wherein the PAAG is greater than 18% arginine-functionalized.

13. The method of claim 1, wherein the PAAG is present in the composition at between 0.1-2 mg/ml.

14. The method of claim 1, the method further comprising administering a nebulizer solution composition configured for inhaled administration.

15. The method of claim 1, wherein the composition is administered in an amount sufficient to provide about 0.2 mg to about 3 mg of PAAG to the subject.

16. The method of claim 1, the method further comprising administering an antibacterial agent.

17. The method of claim 1, wherein the neutral osmol agent is glycerol.

18. The method of claim 17, wherein the glycerol is present in the composition at between 1.2-1.6% v/v.

19. The method of claim 1, wherein the neutral osmol agent is trehalose.

* * * * *